US008431522B2

(12) United States Patent
Costa et al.

(10) Patent No.: US 8,431,522 B2
(45) Date of Patent: *Apr. 30, 2013

(54) METHODS OF INHIBITING TUMOR CELL PROLIFERATION

(75) Inventors: Robert Costa, Oak Park, IL (US); Pradip Raychaudhuri, Oak Park, IL (US); Xinhe Wang, Chicago, IL (US); Vladimir Kalinichenko, Clarendon Hills, IL (US); Michael Major, Chicago, IL (US); I-Ching Wang, Cincinnati, OH (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 225 days.

This patent is subject to a terminal disclaimer.

(21) Appl. No.: 12/871,560

(22) Filed: Aug. 30, 2010

(65) Prior Publication Data

US 2011/0065650 A1     Mar. 17, 2011

Related U.S. Application Data

(62) Division of application No. 11/150,756, filed on Jun. 10, 2005, now Pat. No. 7,799,896, which is a division of application No. 10/809,144, filed on Mar. 25, 2004, now Pat. No. 7,635, 673.

(60) Provisional application No. 60/457,257, filed on Mar. 25, 2003, provisional application No. 60/474,075, filed on May 29, 2003, provisional application No. 60/513,809, filed on Oct. 23, 2003, provisional application No. 60/540,691, filed on Jan. 30, 2004, provisional application No. 60/549,211, filed on Mar. 2, 2004.

(51) Int. Cl.
    *A61K 35/12*     (2006.01)
    *A01N 61/00*     (2006.01)

(52) U.S. Cl.
    USPC ......................... 514/1.1; 424/277.1

(58) Field of Classification Search ........................ None
See application file for complete search history.

(56) References Cited

U.S. PATENT DOCUMENTS

| | | | |
|---|---|---|---|
| 4,064,013 | A | 12/1977 | Meyers et al. |
| 5,089,475 | A | 2/1992 | Wilmore |
| 5,723,313 | A | 3/1998 | Sherr et al. |
| 5,849,686 | A | 12/1998 | Kuberasampath et al. |
| 5,855,920 | A | 1/1999 | Chein |
| 6,172,194 | B1 | 1/2001 | Sherr et al. |
| 6,407,062 | B1* | 6/2002 | Sherr et al. ............ 514/19.3 |
| 6,613,750 | B2 | 9/2003 | DePinho |
| 6,734,167 | B2 | 5/2004 | O'Hare et al. |
| 7,635,673 | B2 | 12/2009 | Costa et al. |
| 7,799,896 | B2 | 9/2010 | Costa et al. |
| 2002/0155988 | A1 | 10/2002 | O'Hare et al. |
| 2002/0156023 | A1 | 10/2002 | Walling et al. |
| 2002/0193325 | A1 | 12/2002 | DePinho |
| 2006/0183130 | A1* | 8/2006 | Hann ........................ 435/6 |
| 2007/0031844 | A1 | 2/2007 | Khvorova et al. |
| 2008/0152618 | A1 | 6/2008 | Gartel et al. |
| 2009/0075376 | A1 | 3/2009 | Costa et al. |
| 2010/0056441 | A1 | 3/2010 | Costa et al. |
| 2010/0098663 | A2 | 4/2010 | Costa et al. |

FOREIGN PATENT DOCUMENTS

| | | |
|---|---|---|
| WO | 01/60374 | 8/2001 |
| WO | 02/26236 | 4/2002 |
| WO | 02/083140 | 10/2002 |
| WO | 02/092013 | 11/2002 |
| WO | 2004/018676 A2 | 3/2004 |
| WO | 2004/019761 A2 | 3/2004 |
| WO | 2004/100977 A1 | 11/2004 |
| WO | 2005/054870 A2 | 6/2005 |
| WO | 2006/009575 A1 | 1/2006 |
| WO | 2006009575 A1 | 1/2006 |
| WO | 2007/109609 A2 | 9/2007 |
| WO | 2008/095112 A2 | 8/2008 |

OTHER PUBLICATIONS

Wender et al, PNAS, 97:13003-13008, 2000.*
Potente, Michael, et al., "11, 12-Epoxyeicosatrienoic Acid-Induced Inhibition FOXO Factors Promotes Endothelial Proliferation by Down-Regulating p27Kip1," The Journal of Biological Chemistry, 2003, vol. 278, No. 32, pp. 29619-29625.
Echeverri, Chris, et al., "siRNA Design: Its All in the Algorithm," Ambion Technotes, May 2004, vol. 11, No. 3, from the World Wide Web, <http://www.ambion.com/techlib/tn/113/14.html>.
Brown, David, "RNAi as a Tool for Mammalian Gene Analysis: Applications of siRNAs," Ambion Technotes, Oct. 2003, vol. 10, No. 5, from the World Wide Web, <http://www.ambion.com/techlib/tn/105/14.html>.
Milhavet, Ollivier, et al., "RNA Interference in Biology and Medicine," Pharmacological Reviews, 2003, vol. 55, No. 4, pp. 629-648.
Katoh, Masuko, "Human FOX Gene Family (Review)," International Journal of Oncology, 2004, vol. 25, No. 5, pp. 1495-1500.
Rye, P.D., et al., "Interfering with Cancer: A Brief Outline of Advances in RNA Interference in Oncology," Tumour Biology: The Journal of the International Society for Oncodevelopmental Biology and Medicine, 2004, vol. 25, No. 5-6, pp. 329-336.
U.S. Appl. No. 11/571,030 (U.S. Counterpart of WO2006/009575).
Wang, I-Ching, et al., "Forkhead Box M1 Regulates the Transcriptional Network of Genes Essential for Mitotic Progression and Genes Encoding the SCF (Skp2-Cks1) Ubiquitin Ligase," Molecular and Cellular Biology, Dec. 2005, vol. 25, No. 24, pp. 10875-10894.

(Continued)

*Primary Examiner* — Lei Yao
(74) *Attorney, Agent, or Firm* — McDonnell Boehnen Hulbert & Berghoff LLP

(57) ABSTRACT

The invention provides methods for inhibiting tumor cell proliferation by inhibiting FoxM1B activity, expression, or nuclear localization in a tumor cell. The invention also provides methods for preventing tumor progression in an animal comprising inhibiting FoxM1B activity, expression, or nuclear localization. Furthermore, the invention provides methods for inhibiting tumor cell growth in an animal comprising inhibiting FoxM1B activity, expression, or nuclear localization in tumor cells in the animal.

24 Claims, 19 Drawing Sheets

OTHER PUBLICATIONS

Pilarsky, Christian, et al., "Identification and Validation of Commonly Overexpressed Genes in Solid Tumors by Comparison of Microarray Data," Neoplasia, 2004, vol. 6, No. 6, pp. 744-750.

Chandran, Uma, R., et al., "Gene Expression of Profiles of Prostate Cancer Reveal Involvement of Multiple Molecular Pathways in the Metastatic Process," BMC Cancer, 2007, 7:64, from the World Wide Web <http://www.biomedcentral.com/1471-2407/7/64>.

Douard, Richard, et al., "Sonic Hedgehog-Dependent Proliferation in a Series of Patients with Colorectal Cancer," Surgery, 2006, pp. 665-670.

Kim, IL-Man, et al., "The Forkhead Box m1 Transcription Factor Stimulates the Proliferation of Tumor Cells During Development of Lung Cancer," Cancer Res., 2006, vol. 66, No. 4, pp. 2153-2161.

Gusarova, Galina, A., et al., "A Cell-Penetrating ARF Peptide Inhibitor of FoxM1 in Mouse Hepatocellular Carcinoma Treatment," The Journal of Clinical Investigation, 2007, vol. 117, No. 1, pp. 99-111.

Wang, I-C, et al., "Transgenic Expression of the Forkhead Box M1 Transcription Factor Induces Formation of Lung Tumors," Oncogene, 2008, pp. 1-13.

Wang, X., et al., "Increased Levels of Forkhead box M1B Transcription Factor in Transgenic Mouse Hepatocytes Prevent Age-Related Proliferation Defects in Regenerating Liver," PNAS, Sep. 25, 2001, vol. 98, No. 20, pp. 11468-11473.

Wang, et al., "Earlier Expression of the Transcription Factor HFH-11B Diminishes Induction of p21CIPI/WAF1 Levels and Accelerates Mouse Hepatocyte Entry Into S-Phase Following Carbon Tetrachloride Liver Injury," Hepatology, 2001, vol. 33, No. 6, pp. 1-11.

Ly, Danith H., et al., "Mitotic Misregulation and Human Aging," Science, 2000, vol. 287, pp. 2486-2492.

Asakawa, K., et al., "Human Growth Hormone Stimulates Liver Regeneration in Rats," J. Endocrinol. Invest, 1989, vol. 12, pp. 343-347.

Charrier, Martal, J., et al., Retraction "Growth Horomones. 1. Polymorphism (minireview)," Reprod. Nutr. Dev., 1988, 28(4A), pp. 857-887.

Luscher-Firzlaff, Juliane M., et al., "Interaction of the Fork Head Domain Transcription Factor MPP2 with the Human Papilloma Virus 16 E7 Protein: Enhancement of Transformation and Transactivation," Oncogene, 1999, vol. 18, pp. 5620-5630.

Barle, Hans, et al., "Depression of Liver Protein Synthesis During Surgery is Prevented by Growth Hormone," American Physiological Society, 1999, 276 (4 Pt 1) pp. E620-E627.

Krupczak-Hollis et al., "Growth Hormone Stimulates Proliferation of Old-Aged Regenerating Liver Through Forkhead Box m1b" Hepatology 38(6): 1552-62 (Dec. 2003).

Wang et al.' "The Forkhead Box mi b transcription factor is essential for hepatocyte DNA replication and mitosis during mouse liver regeneration" PNAS 99(26): 16881-6 (Dec. 24, 2002).

Korver et al., "The Human TRIDENTIHFG-1 IIFKHL 16 Gene: Structure, Localization, and Promoter Characterization" Genomics 46:435-442 (1997).

Korver et al., "The winged-helix transcription factor Trident is expressed in cycling cells" Nucleic Acids Research 25(9): 1715-19 (1997).

Yao et a/., Molecular Analysis of a Novel Winged Helix Protein, WIN The Journal of Biological Chemistry 272(32): 19827-36 (Aug. 8, 1997).

Ye et al., "Hepatocyte Nuclear Factor 3lfork head Homolog 11 Is Expressed in Proliferating Epithelial and Mesechymal Cells of Embryonic and Adult Tissues" Molecular and Cellular Biology 17(3): 1626-41 (1997).

Ye et al., "Premature Expression of the Winged Helix Transcription Factor HFH-116 in Regenerating Mouse Liver Accelerates Hepatocyte Entry into S. Phase" Molecular and Cellular Biology 19(13): 8570-80 (1999).

Supriatno et al, "Overexpression of p27 induces growth arrest and apoptosis in an oral cancer cell line" Oral Oncology 38(7): 730-736 (2002).

The et al "FOXMI is a Downstream Target of Glil in Basal Cell carcinomas" Cancer Research 62(16): 4773-4780 (2002).

Kalinichenko VV et al., "Foxm1b transcription factor is Essential for Development of Hepatocellular Carcinomas and is Negatively Regulated by the p19/Arf Tumor Suppressor" Genes & Development 18: 830-850 (2004).

Laoukili et al., "FoxM1 Is Required for Execution of the Mitotic Programme and Chromosome Stability", Nature Cell Biology, Feb. 2005, 7(2):126-136; Supp. pp. 1-4.

Costa, "FoxM1 Dances With Mitosis", Nature Cell Biology, Feb. 2005, 7(2):108-110.

Wonsey et al., "Loss of the Forkhead Transcription Factor FoxM1 Causes Centrosome Amplification and mitotic Catastrophe", Cancer Research, Jun. 15, 2005, 65(12): 5181-5189.

Okabe et al., "Genome-wide Analysis of Gene Expression in Human Hepatocellular Carcinomas Using cDNA Microarray: Identification of Genes Involved in viral Carcinogenesis and Tumor Progression", Cancer Research, Mar. 1, 2001, 61:2129-2137.

Lee et al., "Classification and Prediction of Survival in Hepatocellular Carcinoma by Gene Expression Profiling", Hepatology, Sep. 2004, 40(3):667-676.

Obama et al., "Genome-Wide Analysis of Gene Expression in Human Intrahepatic Cholangiocarcinoma", Hepatology, Jun. 2005, 41(6):1339-1348.

Van Den Boom et al., "Characterization of Gene Expression Profiles Associated with Glioma Progression Using Oligonucleotide-Based Microarray Analysis and Real-Time Reverse Transcription-Polymerase Chain Reaction", American Journal of Pathology, Sep. 2003, 163(3):1033-1043.

Kalin et al., "Increased Levels of the FoxM1 Transcription Factor Accelerate Development and Progression of Prostate Carcinomas in both TRAMP and LADY Transgenic Mice". Cancer Research, Feb. 1, 2006; 66(3):1712-1720.

Radhakrishnan et al., "Constitutive Expression of E2F-1 Leads to P21-Dependent Cell Cycle Arrest in S Phase of the Cell Cycle", Oncogene, 2004, 23:4173-4176.

Radhakrishnan et al., "The PPAR-Y Agonist Pioglitazone Post-Transcriptionally Induces p21 in PC3 Prostate Cancer But Not in Other Cells Lines", Cell Cycle, 2005, 4(4):582-584.

Radhakrishnan et al., "Multiple Alternate p21 Transcripts are Regulated by p53 in Human Cells", Oncogene, 2006, 25:1812-1815.

Conzen et al., "Induction of Cell Cycle Progression and Acceleration of Apoptosis Are Two Separable Functions of c-Myc: Transrepression Correlates with Acceleration of Apoptosis". Molecular and Cellular Biology, Aug. 2000, 20 (16):6008-6018.

Lentzen et al. "Structural Basis for Contrasting Activities of Ribosome Binding Thiazole Antibiotics". Chemistry & Biology, Aug. 2003, 10:769-778.

Radhakrishnan et al., "A Novel Transcriptional Inhibitor Induces Apoptosis in Tumor Cells and Exhibits Antiangiogenic Activity". Cancer Research, Mar. 15, 2006, 66(6):3264-3270.

Weinstein, "Addiction to Oncogenes—the Achilles Heal of Cancer", Science, Jul. 5, 2002, 297:63-64.

Hagg et al. "A Novel High-through-Put Assay for Screening of Pro-Apoptotic Drugs", Investigational New Drugs, 2002, 20:253-259.

Erdal et al., "Induction of Lysosomal Membrane Permeabilization by Compounds That Activate p53 Independent Apoptosis", PNAS, Jan. 4, 2005, 102(1):192-197.

Monga et al., "Developmental Therapeutics Program at the NCI: Molecular Target and Drug Discovery Process", Leukemia, 2002, 16:520-526.

Nicolaou et al., "Discovery of a Biologically Active Thiostrepton Fragment", J. Am. Chem. Soc., 2005, 127(43): 15042-15044.

Radhakrishnan et al., "Identification of a Chemical Inhibitor of the Oncogenic Transcription Factor Forkhead Box M1", Cancer Research, Oct. 1, 2006, 66(19):9731-9735.

Madureira et al., "The Forkhead Box M1 Protein Regulates the Transcription of the Estrogen Receptor Alpha in Breast Cancer Cells", Journal of Biological Chemistry, Sep. 1, 2006, 281(35):25167-25176.

Smith et al., "The TNF Receptor Superfamily of Cellular and Viral Proteins: Activation, Costimulation, and Death", Cell, Mar. 25, 1994, 76:959-962.

Ashkenazi et al., "Apoptosis Control by Death and Decoy Receptors", Cell Biology, 1999, 11:255-260.

Ashkenazi et al., "Death Receptors: Signaling and Modulation", Science, Aug. 28, 1998, 281(5381):1305-1308.

Schulze-Osthoff et al., "Apoptosis Signaling by Death Receptors", Eur. J. Biochem., 1998, 254:439-459.

Van Antwerp et al., "Inhibition of TNF-Induced Apoptosis by NF-kB", Trends in Cell Biology, Mar. 1998, 8:107-111.

Nagata et al., "The fas death factor", Science, Mar. 10, 1995, 267(5203):1449.

Griffith et al., "TRAIL: A Molecule with Multiple Receptors and Control Mechanisms", Current Opinion in Immunology, 1998, 10:559-563.

Yeh et al., "FADD: Essential for Embryo Development and Signaling from Some, but Not All Inducers of Apoptosis", Science, Mar. 20, 1998, 279(5358):1954-1957.

Muzio et al., "FLICE, A Novel FADD-Homologous ICE/CED-3-Like Protease, Is Recruited to the CD95 (Fax/APO-1) Death-Inducing Signaling Complex", Cell, Jun. 14, 1996, 85:817-827.

Hsu et al., "TRADD-TRAF2 and TRADD-FADD Interactions Define Two Distinct TNF Receptor 1 Signal Transduction Pathways", Cell, Jan. 26, 1996, 84:299-308.

Boldin et al., "Involvement of MACH, a Novel MORT1/FADD-Interactiing Protease, in Fax/APO-1-and TNF Receptor-Induced Cell Death", Cell, Jun. 14, 1996, 85:803-815.

Major et al., 2004, Molecular Cell Biology, vol. 24, pp. 2649-2661.

Major et al., "Forkhead Box MIB Transccriptional Activity Requires Binding of Cdk-Cyclin Complexes for Phosphorylation-Dependent Recruitment of p3001CBP Coactivators" Molecular and Cellular Biology 24(7): 2649-61 (Apr. 2004).

Wender et al., PNAS, vol. 97, pp. 13003-13008, 2000.

Curti, Brendan, D., "Physical Barriers to Drug Delivery in Tumors," Critical Reviews in Oncology/Hematology, 1993, 14:29-39.

Dermer, Gerald B., "Another Anniversary for the War on Cancer," Bio/Technology, 1994, 12:320.

Freshney, Ian R., "Culture of Animals Cells, A Manual of Basic Technique," Alan R. Liss, Inc., 1983, pp. 3-4.

Gura, "Systems for Identifying New Drugs are Often Faulty," Science, 1997, 278:1041-1042.

Jain, Rakesh K., "Barriers to Drug Delivery in Solid Tumors," Scientific American, 1994, 271:58-65.

Johnson, OluFunmi L, et al., "Peptide and Protein Drug Delivery," In Encyclopedia of Controlled Drug Delivery, vol. 2, 1999, pp. 816-833.

Kalinichenko, Vladimir V., et al., "Foxm1b Transcription Factor is Essential for Development of Hepatocellular Carcinomas and is Negatively Regulated by the p19ARF Tumor Suppressor," Genes & Development, 2004, 18:830-850.

Lees, Jean-Francois, et al, "Alteration of P19ARF in Rodent Hepatoma Cell Lines but not in Human Primary Liver Cancer," Cancer Genet Cytogenet, 2000, 117:118-124.

Zips, Daniel, et al., "New Anticancer Agents: In Vitro and In Vivo Evaluation," In Vivo, 2005, 19:1-7.

Kalinichenko et al., Genes and Devel, vol. 18 p. 830-850, 2004.

Sequence search result A, cited by the Office on Nov. 27, 2007 in U.S. Appl. No. 11/150,756.

UniProt database accession No. Q9Z1E7, May 1999, sequence search result B, cited by the Office on Nov. 27, 2007 in U.S. Appl. No. 11/150,756.

Weber et al., Mol. Cel. Bio, vol. 20m p. 2517-2528, 2000.

Wang et al. "Increased Hepatic Forkhead Box MI B (FoxM1 B) Levels in Old-aged Mice Stimulated Liver Regarneration through Diminished p27Kip" Journal of Biological Chemistry 277(46): 44310-16 (Nov. 15, 2002).

Tanya V. Kalin et al., "Increased Levels of the FoxM1 Transcription Factor Accelerate Development and Progression of Prostate Carcinomas in both TRAMP and LADY Transgenic Mice", Cancer Research; 66: (3), Feb. 1, 2006.

Tonya Kalinichenko, Poster presented at American Associate of Cancer Research meeting in Seattle, Washington from Oct. 16-20, 2004.

* cited by examiner

Figure 1A

```
ggagcccgga gcccgccttc ggagctacgg cctaacggcg gcggcgactg cagtctggag 60
ggtccacact tgtgattctc aatggagagt gaaaacgcag attcataatg aaaactagcc 120
ccgtcggcc actgattctc aaaagacgga ggctgcccct tcctgttcaa aatgccccaa 180
gtgaaacatc agaggaggaa cctaagagat cccctgccca acaggagtct aatcaagcag 240
aggcctccaa ggaagtggca gagtccaact cttgcaagtt tccagctggg atcaagatta 300
ttaaccaccc caccatgccc aacacgcaag tagtggccat cccaacaat gctaatattc 360
acagcatcat cacagcactg actgccaagg gaaaagagag tggcagtagt gggcccaaca 420
aattcatcct catcagctgt ggggagccc caactcagcc tccaggactc cggcctcaaa 480
cccaaaccag ctatgatgcc aaaaggacag aagtgaccct ggagaccttg ggaccaaaac 540
ctgcagctag ggatgtgaat cttcctagac cacctggagc cctttgcgag cagaaacggg 600
agacctgtgc agatggtgag gcagcaggct gcactatcaa caatagccta tccaacatcc 660
agtggcttcg aaagatgagt tctgatggac tgggctcccg cagcatcaag caagagatgg 720
aggaaaagga gaattgtcac ctggagcagc gacaggttaa ggttgaggag ccttcgagac 780
catcagcgtc ctggcagaac tctgtgtctg agcggccacc ctactcttac atggccatga 840
tacaattcgc catcaacagc actgagagga agcgcatgac tttgaaagac atctatacgt 900
ggattgagga ccactttccc tactttaagc acattgccaa gccaggctgg aagaactcca 960
tccgccacaa ccttttccct gcacgacatgt tgtccggga gacgtctgcc aatggcaagg 1020
tctccttctg gaccattcac cccagtgcca accgctactt gacattggac caggtgttta 1080
agcagcagaa acgaccgaat ccagagctcc gccggaacat gaccatcaaa ccgaactcc 1140
ccctgggcgc acggcggaag atgaagccac tgctaccacg ggtcagctca tacctggtac 1200
ctatccagtt ccggtgaac cagtcactgg tgttgcagcc ctcggtgaag gtgccattgc 1260
ccctggcggc ttccctcatg agctcagagc ttgcccgcca tagcaagcga gtccgcattg 1320
ccccaaggt gctgctagct gaggagggga tagctcctct ttcttctgca ggaccaggga 1380
aagaggagaa actcctgttt ggagaagggt tttctccttt gcttccagtt cagactatca 1440
```

Figure 1B

```
aggaggaaga aatccagcct ggggaggaaa tgccacactt agcgagaccc atcaaagtgg 1500
agagccctcc cttggaagag tggccctccc cggccccatc tttcaaagag gaatcatctc 1560
actcctggga ggattcgtcc caatctccca ccccaagacc caagaagtcc tacagtgggc 1620
ttaggtcccc aacccggtgt gtctcggaaa tgcttgtgat tcaacacagg gagaggaggg 1680
agaggagccg gtctcggagg aaacagcatc tactgcctcc ctgtgtggat gagccggagc 1740
tgctcttctc agagggccc agtacttccc gctgggccgc agagctcccg ttcccagcag 1800
actcctctga ccctgcctcc cagctcagct actcccagga agtgggagga cctttaaga 1860
cacccattaa ggaaacgctg cccatctcct ccaccccgag caaatctgtc ctccccagaa 1920
ccctgaatc ctggaggctc acgccccag ccaaagtagg gggactggat ttcagcccag 1980
tacaaacctc ccagggtgcc tctgaccct tgcctgaccc cctggggctg atggatctca 2040
gcaccactcc cttgcaaagt gctcccccc ttgaatcacc gcaaaggctc ctcagttcag 2100
aacccttaga cctcatctcc gtcccttttg gcaactcttc tccctcagat atagacgtcc 2160
ccaagccagg ctccccggag ccacaggttt ctggccttgc agccaatcgt tctctgacag 2220
aaggcctggt cctggacaca atgaatgaca gcctcagcaa gatcctgctg gacatcagct 2280
ttcctggcct ggacgaggac ccactgggcc ctgacaacat caactggtcc cagtttattc 2340
ctgagctaca gtagagccct gcccttgccc ctgtgctcaa gctgtccacc atcccgggca 2400
ctccaaggct cagtgcaccc caagcctctg agtgaggaca gcaggcaggg actgttctgc 2460
tcctcatagc tccctgctgc ctgattatgc aaaagtagca gtcacaccct agccactgct 2520
gggaccttgt gttccccaag agtatctgat tcctctgctg tccctgccag gagctgaagg 2580
gtgggaacaa caaaggcaat ggtgaaaaga gattaggaac ccccagcct gtttccattc 2640
tctgcccagc agtctcttac cttccctgat ctttgcaggg tggtccgtgt aaatagtata 2700
aattctccaa attatcctct aattataaat gtaagct                     2737
```

Figure 1C

```
MKTSPRRPLI LKRRRLPLPV QNAPSETSEE EPKRSPAQQE SNQAEASKEV AESNSCKFPA    60
GIKIINHPTM PNTQVVAIPN NANIHSIITA LTAKGKESGS SGPNKFILIS CGGAPTQPPG   120
LRPQTQTSYD AKRTEVTLET LGPKPAARDV NLPRPPGALC EQKRETCADG EAAGCTINNS   180
LSNIQWLRKM SSDGLGSRSI KQEMEEKENC HLEQRQVKVE EPSRPSASWQ NSVSERPPYS   240
YMAMIQFAIN STERKRMTLK DIYTWIEDHF PYFKHIAKPG WKNSIRHNLS LHDMFVRETS   300
ANGKVSFWTI HPSANRYLTL DQVFKQQKRP NPELRRNMTI KTELPLGARR KMKPLLPRVS   360
SYLVPIQFPV NQSLVLQPSV KVPLPLAASL MSSELARHSK RVRIAPKVLL AEEGIAPLSS   420
AGPGKEEKLL FGEGFSPLLP VQTIKEEEIQ PGEEMPHLAR PIKVESPPLE EWPSPAPSFK   480
EESSHSWEDS SQSPTPRPKK SYSGLRSPTR CVSEMLVIQH RERPERSRSR RKQHLLPPCV   540
DEPELLFSEG PSTSRWAAEL PFPADSSDPA SQLSYSQEVG GPFKTPIKET LPISSTPSKS   600
VLPRTPESWR LTPPAKVGGL DFSPVQTSQG ASDPLPDPLG LMDLSTTPLQ SAPPLESPQR   660
LLSSEPLDLI SVPFGNSSPS DIDVPKPGSP EPQVSGLAAN RSLTEGLVLD TMNDSLSKIL   720
LDISFPGLDE DPLGPDNINW SQFIPELQ                                     748
```

GFP-FoxM1B

SEQUENCE LISTING

```
<160> NUMBER OF SEQ ID NOS: 14

<210> SEQ ID NO 1
<211> LENGTH: 2737
<212> TYPE: DNA
<213> ORGANISM: Homo sapiens

<400> SEQUENCE: 1
ggagcccgga gcccgccttc ggagctacgg cctaacggcg gcggcgactg cagtctggag      60
ggtccacact tgtgattctc aatggagagt gaaaacgcag attcataatg aaaactagcc     120
cccgtcggcc actgattctc aaaagacgga ggctgcccct tcctgttcaa aatgccccaa     180
gtgaaacatc agaggaggaa cctaagagat cccctgccca acaggagtct aatcaagcag     240
aggcctccaa ggaagtggca gagtccaact cttgcaagtt tccagctggg atcaagatta     300
ttaaccaccc caccatgccc aacacgcaag tagtggccat ccccaacaat gctaatattc     360
acagcatcat cacagcactg actgccaagg gaaaagagag tggcagtagt gggcccaaca     420
aattcatcct catcagctgt gggggagccc caactcagcc tccaggactc cggcctcaaa     480
cccaaaccag ctatgatgcc aaaaggacag aagtgaccct ggagaccttg ggaccaaaac     540
ctgcagctag ggatgtgaat cttcctagac cacctggagc cctttgcgag cagaaacggg     600
agacctgtgc agatggtgag gcagcaggct gcactatcaa caatagccta tccaacatcc     660
```

-continued

```
agtggcttcg aaagatgagt tctgatggac tgggctcccg cagcatcaag caagagatgg    720
aggaaaagga gaattgtcac ctggagcagc gacaggttaa ggttgaggag ccttcgagac    780
catcagcgtc ctggcagaac tctgtgtctg agcggccacc ctactcttac atggccatga    840
tacaattcgc catcaacagc actgagagga agcgcatgac tttgaaagac atctatacgt    900
ggattgagga ccactttccc tactttaagc acattgccaa gccaggctgg aagaactcca    960
tccgccacaa cctttccctg cacgacatgt tgtccggga gacgtctgcc aatggcaagg    1020
tctccttctg gaccattcac cccagtgcca accgctactt gacattggac caggtgttta    1080
agcagcagaa acgaccgaat ccagagctcc gccggaacat gaccatcaaa accgaactcc    1140
ccctgggcgc acggcggaag atgaagccac tgctaccacg ggtcagctca tacctggtac    1200
ctatccagtt cccggtgaac cagtcactgg tgttgcagcc ctcggtgaag gtgccattgc    1260
ccctggcggc ttccctcatg agctcagagc ttgcccgcca tagcaagcga gtccgcattg    1320
cccccaaggt gctgctagct gaggagggga tagctcctct ttcttctgca ggaccaggga    1380
aagaggagaa actcctgttt ggagaagggt tttctccttt gcttccagtt cagactatca    1440
aggaggaaga aatccagcct ggggaggaaa tgccacactt agcgagaccc atcaaagtgg    1500
agagccctcc cttggaagag tggccctccc ggccccatc tttcaaagag gaatcatctc    1560
actcctggga ggattcgtcc caatctccca ccccaagacc caagaagtcc acagtgggc    1620 ttaggtcccc aacccggtgt gtctcggaaa tgcttgtgat caacacagg gagaggaggg    1680 agaggagccg gtctcggagg aaacagcatc tactgcctcc ctgtgtggat gagccggagc    1740
tgctcttctc agaggggccc agtacttccc gctgggccgc agagctcccg ttcccagcag    1800
actcctctga ccctgcctcc cagctcagct actcccagga agtgggagga cctttaaga    1860 cacccattaa ggaaacgctg cccatctcct ccaccccgag caaatctgtc ctccccagaa    1920
cccctgaatc ctggaggctc acgccccag ccaaagtagg gggactggat ttcagcccag    1980
tacaaacctc ccagggtgcc tctgacccct tgcctgaccc cctgggctg atggatctca    2040 gcaccactcc cttgcaaagt gctccccccc ttgaatcacc gcaaaggctc ctcagttcag    2100
aacccttaga cctcatctcc gtccccttg gcaactcttc tccctcagat atagacgtcc    2160
ccaagccagg ctccccggag ccacaggttt ctggccttgc agccaatcgt tctctgacag    2220
aaggcctggt cctggacaca atgaatgaca gcctcagcaa gatcctgctg gacatcagct    2280
ttcctggcct ggacgaggac ccactgggcc ctgacaacat caactggtcc cagtttattc    2340
ctgagctaca gtagagccct gcccttgccc ctgtgctcaa gctgtccacc atcccgggca    2400
ctccaaggct cagtgcaccc caagcctctg agtgaggaca gcaggcaggg actgttctgc    2460
tcctcatagc tccctgctgc ctgattatgc aaaagtagca gtcacaccct agccactgct    2520 gggacccttgt gttccccaag agtatctgat tcctctgctg tccctgccag gagctgaagg    2580
gtgggaacaa caaaggcaat ggtgaaaaga gattaggaac cccccagcct gtttccattc    2640
tctgcccagc agtctcttac cttccctgat cttgcaggg tggtccgtgt aaatagtata    2700
aattctccaa attatcctct aattataaat gtaagct                             2737
```

<210> SEQ ID NO 2
<211> LENGTH: 748
<212> TYPE: PRT
<213> ORGANISM: Homo sapiens

<400> SEQUENCE: 2

Met Lys Thr Ser Pro Arg Arg Pro Leu Ile Leu Lys Arg Arg Arg Leu

-continued

```
1               5                   10                  15
Pro Leu Pro Val Gln Asn Ala Pro Ser Glu Thr Ser Glu Glu Pro
            20                  25                  30

Lys Arg Ser Pro Ala Gln Gln Glu Ser Asn Gln Ala Glu Ala Ser Lys
            35                  40                  45

Glu Val Ala Glu Ser Asn Ser Cys Lys Phe Pro Ala Gly Ile Lys Ile
            50                  55                  60

Ile Asn His Pro Thr Met Pro Asn Thr Gln Val Val Ala Ile Pro Asn
65                  70                  75                  80

Asn Ala Asn Ile His Ser Ile Ile Thr Ala Leu Thr Ala Lys Gly Lys
                    85                  90                  95

Glu Ser Gly Ser Gly Pro Asn Lys Phe Ile Leu Ile Ser Cys Gly
                100                 105                 110

Gly Ala Pro Thr Gln Pro Pro Gly Leu Arg Pro Gln Thr Gln Thr Ser
            115                 120                 125

Tyr Asp Ala Lys Arg Thr Glu Val Thr Leu Glu Thr Leu Gly Pro Lys
            130                 135                 140

Pro Ala Ala Arg Asp Val Asn Leu Pro Arg Pro Pro Gly Ala Leu Cys
145                 150                 155                 160

Glu Gln Lys Arg Glu Thr Cys Ala Asp Gly Glu Ala Ala Gly Cys Thr
                165                 170                 175

Ile Asn Asn Ser Leu Ser Asn Ile Gln Trp Leu Arg Lys Met Ser Ser
                180                 185                 190

Asp Gly Leu Gly Ser Arg Ser Ile Lys Gln Glu Met Glu Glu Lys Glu
                195                 200                 205

Asn Cys His Leu Glu Gln Arg Gln Val Lys Val Glu Glu Pro Ser Arg
                210                 215                 220

Pro Ser Ala Ser Trp Gln Asn Ser Val Ser Glu Arg Pro Pro Tyr Ser
225                 230                 235                 240

Tyr Met Ala Met Ile Gln Phe Ala Ile Asn Ser Thr Glu Arg Lys Arg
                245                 250                 255

Met Thr Leu Lys Asp Ile Tyr Thr Trp Ile Glu Asp His Phe Pro Tyr
                260                 265                 270

Phe Lys His Ile Ala Lys Pro Gly Trp Lys Asn Ser Ile Arg His Asn
                275                 280                 285

Leu Ser Leu His Asp Met Phe Val Arg Glu Thr Ser Ala Asn Gly Lys
            290                 295                 300

Val Ser Phe Trp Thr Ile His Pro Ser Ala Asn Arg Tyr Leu Thr Leu
305                 310                 315                 320

Asp Gln Val Phe Lys Gln Gln Lys Arg Pro Asn Pro Glu Leu Arg Arg
                325                 330                 335

Asn Met Thr Ile Lys Thr Glu Leu Pro Leu Gly Ala Arg Arg Lys Met
            340                 345                 350

Lys Pro Leu Leu Pro Arg Val Ser Ser Tyr Leu Val Pro Ile Gln Phe
            355                 360                 365

Pro Val Asn Gln Ser Leu Val Leu Gln Pro Ser Val Lys Val Pro Leu
370                 375                 380

Pro Leu Ala Ala Ser Leu Met Ser Ser Glu Leu Ala Arg His Ser Lys
385                 390                 395                 400

Arg Val Arg Ile Ala Pro Lys Val Leu Leu Ala Glu Glu Gly Ile Ala
                405                 410                 415

Pro Leu Ser Ser Ala Gly Pro Gly Lys Glu Glu Lys Leu Leu Phe Gly
            420                 425                 430
```

```
Glu Gly Phe Ser Pro Leu Leu Pro Val Gln Thr Ile Lys Glu Glu
        435                 440                 445

Ile Gln Pro Gly Glu Met Pro His Leu Ala Arg Pro Ile Lys Val
450                 455                 460

Glu Ser Pro Pro Leu Glu Glu Trp Pro Ser Pro Ala Pro Ser Phe Lys
465                 470                 475                 480

Glu Glu Ser Ser His Ser Trp Glu Asp Ser Ser Gln Ser Pro Thr Pro
                485                 490                 495

Arg Pro Lys Lys Ser Tyr Ser Gly Leu Arg Ser Pro Thr Arg Cys Val
                500                 505                 510

Ser Glu Met Leu Val Ile Gln His Arg Glu Arg Glu Arg Ser Arg
515                 520                 525

Ser Arg Arg Lys Gln His Leu Leu Pro Pro Cys Val Asp Glu Pro Glu
530                 535                 540

Leu Leu Phe Ser Glu Gly Pro Ser Thr Ser Arg Trp Ala Ala Glu Leu
545                 550                 555                 560

Pro Phe Pro Ala Asp Ser Ser Asp Pro Ala Ser Gln Leu Ser Tyr Ser
                565                 570                 575

Gln Glu Val Gly Gly Pro Phe Lys Thr Pro Ile Lys Glu Thr Leu Pro
                580                 585                 590

Ile Ser Ser Thr Pro Ser Lys Ser Val Leu Pro Arg Thr Pro Glu Ser
                595                 600                 605

Trp Arg Leu Thr Pro Pro Ala Lys Val Gly Gly Leu Asp Phe Ser Pro
610                 615                 620

Val Gln Thr Ser Gln Gly Ala Ser Asp Pro Leu Pro Asp Pro Leu Gly
625                 630                 635                 640

Leu Met Asp Leu Ser Thr Thr Pro Leu Gln Ser Ala Pro Pro Leu Glu
                645                 650                 655

Ser Pro Gln Arg Leu Leu Ser Ser Glu Pro Leu Asp Leu Ile Ser Val
                660                 665                 670

Pro Phe Gly Asn Ser Ser Pro Ser Asp Ile Asp Val Pro Lys Pro Gly
                675                 680                 685

Ser Pro Glu Pro Gln Val Ser Gly Leu Ala Ala Asn Arg Ser Leu Thr
                690                 695                 700

Glu Gly Leu Val Leu Asp Thr Met Asn Asp Ser Leu Ser Lys Ile Leu
705                 710                 715                 720

Leu Asp Ile Ser Phe Pro Gly Leu Asp Glu Asp Pro Leu Gly Pro Asp
                725                 730                 735

Asn Ile Asn Trp Ser Gln Phe Ile Pro Glu Leu Gln
                740                 745
```

<210> SEQ ID NO 3
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa is any amino acid
<220> FEATURE:
<221> NAME/KEY: misc_feature
<222> LOCATION: (4)..(5)
<223> OTHER INFORMATION: Xaa is any amino acid

<400> SEQUENCE: 3

```
Leu Xaa Leu Xaa Xaa Leu
1               5
```

<210> SEQ ID NO 4
<211> LENGTH: 66
<212> TYPE: DNA
<213> ORGANISM: Artificial Sequence
<220> FEATURE:
<223> OTHER INFORMATION: Synthetic; EcoR1 T-epitope tagged FoxM1B primer

<400> SEQUENCE: 4
gcggaattca ccatggctag catgactggt ggacagcaaa tgggttggca gaactctgtg    60
tctgag                                                              66

<210> SEQ ID NO 5
<211> LENGTH: 18
<212> TYPE: DNA
<213> ORGANISM: Artificial Sequence
<220> FEATURE:
<223> OTHER INFORMATION: Synthetic; antisense primer for CMV expression
      vector SV-40 poly A region

<400> SEQUENCE: 5
gtttgtccaa ttatgtca                                                 18

<210> SEQ ID NO 6
<211> LENGTH: 12
<212> TYPE: DNA
<213> ORGANISM: Artificial Sequence
<220> FEATURE:
<223> OTHER INFORMATION: FoxM1B/FoxA binding site

<400> SEQUENCE: 6
tttgtttgtt tg                                                       12

<210> SEQ ID NO 7
<211> LENGTH: 6
<212> TYPE: RNA
<213> ORGANISM: Artificial Sequence
<220> FEATURE:
<223> OTHER INFORMATION: Synthetic; transcription termination signal

<400> SEQUENCE: 7 aauaaa                                                              6

<210> SEQ ID NO 8
<211> LENGTH: 81
<212> TYPE: PRT
<213> ORGANISM: Homo sapiens

<400> SEQUENCE: 8

Pro Phe Lys Thr Pro Ile Lys Glu Thr Leu Pro Ile Ser Ser Thr Pro
1               5                   10                  15

Ser Lys Ser Val Leu Pro Arg Thr Pro Glu Ser Trp Arg Leu Thr Pro
            20                  25                  30

Pro Ala Lys Val Gly Gly Leu Asp Phe Ser Pro Val Gln Thr Ser Gln
        35                  40                  45

Gly Ala Ser Asp Pro Leu Pro Asp Pro Leu Gly Leu Met Asp Leu Ser
    50                  55                  60

Thr Thr Pro Leu Gln Ser Ala Pro Pro Leu Glu Ser Pro Gln Arg Leu
65                  70                  75                  80

Leu

<210> SEQ ID NO 9
<211> LENGTH: 28

```
<212> TYPE: PRT
<213> ORGANISM: Artificial Sequence
<220> FEATURE:
<223> OTHER INFORMATION: Synthetic; LXLXXL motif from FoxM1B amino acid
      residue 635 to 662
<220> FEATURE:
<221> NAME/KEY: misc_feature
<222> LOCATION: (2)..(4)
<223> OTHER INFORMATION: Xaa is any amino acid
<220> FEATURE:
<221> NAME/KEY: misc_feature
<222> LOCATION: (6)..(6)
<223> OTHER INFORMATION: Xaa is any amino acid
<220> FEATURE:
<221> NAME/KEY: misc_feature
<222> LOCATION: (8)..(9)
<223> OTHER INFORMATION: Xaa is any amino acid
<220> FEATURE:
<221> NAME/KEY: misc_feature
<222> LOCATION: (11)..(14)
<223> OTHER INFORMATION: Xaa is any amino acid
<220> FEATURE:
<221> NAME/KEY: misc_feature
<222> LOCATION: (16)..(20)
<223> OTHER INFORMATION: Xaa is any amino acid
<220> FEATURE:
<221> NAME/KEY: misc_feature
<222> LOCATION: (22)..(26)
<223> OTHER INFORMATION: Xaa is any amino acid

<400> SEQUENCE: 9

Leu Xaa Xaa Xaa Leu Xaa Leu Xaa Xaa Leu Xaa Xaa Xaa Xaa Leu Xaa
1               5                   10                  15

Xaa Xaa Xaa Xaa Leu Xaa Xaa Xaa Xaa Xaa Leu Leu
            20                  25

<210> SEQ ID NO 10
<211> LENGTH: 28
<212> TYPE: PRT
<213> ORGANISM: Mus musculus
<220> FEATURE:
<221> NAME/KEY: misc_feature
<222> LOCATION: (1)..(9)
<223> OTHER INFORMATION: Xaa is D-Arginine

<400> SEQUENCE: 10

Xaa Xaa Xaa Xaa Xaa Xaa Xaa Xaa Xaa Lys Phe Val Arg Ser Arg Arg
1               5                   10                  15

Pro Arg Thr Ala Ser Cys Ala Leu Ala Phe Val Asn
            20                  25

<210> SEQ ID NO 11
<211> LENGTH: 19
<212> TYPE: PRT
<213> ORGANISM: Mus Musculus

<400> SEQUENCE: 11

Lys Phe Val Arg Ser Arg Arg Pro Arg Thr Ala Ser Cys Ala Leu Ala
1               5                   10                  15

Phe Val Asn

<210> SEQ ID NO 12
<211> LENGTH: 30
<212> TYPE: PRT
<213> ORGANISM: Mus musculus

<400> SEQUENCE: 12

Lys Phe Val Arg Ser Arg Arg Pro Arg Thr Ala Ser Cys Ala Leu Ala
1               5                   10                  15
```

-continued

```
Phe Val Asn Met Leu Leu Arg Leu Glu Arg Ile Leu Arg Arg
             20                  25                  30

<210> SEQ ID NO 13
<211> LENGTH: 13
<212> TYPE: PRT
<213> ORGANISM: Human immunodeficiency virus

<400> SEQUENCE: 13

Met Gly Tyr Gly Arg Lys Lys Arg Arg Gln Arg Arg Arg
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: Xaa is D-Arginine

<400> SEQUENCE: 14

Xaa Xaa Xaa Xaa Xaa Xaa Xaa Xaa Xaa
1               5
```

METHODS OF INHIBITING TUMOR CELL PROLIFERATION

This application is a divisional application of U.S. application Ser. No. 11/150,756, filed Jun. 10, 2005, now U.S. Pat. No. 7,799,896, which is a divisional application of U.S. application Ser. No. 10/809,144 filed Mar. 25, 2004, now U.S. Pat. No. 7,635,673, which is related to and claims priority to U.S. provisional application Ser. No. 60/457,257 filed Mar. 25, 2003, U.S. provisional application Ser. No. 60/474,075 filed May 29, 2003, U.S. provisional application Ser. No. 60/513,809 filed Oct. 23, 2003, U.S. provisional application Ser. No. 60/540,691 filed Jan. 30, 2004, and U.S. provisional application Ser. No. 60/549,211 filed Mar. 2, 2004, the disclosure of each of which is incorporated by reference herein.

This invention was made with government support under AG21842-02 awarded by the National Institute on Aging, and under DK54687-06 awarded by the National Institute of Diabetes and Digestive and Kidney Diseases. The government has certain rights in the invention.

BACKGROUND OF THE INVENTION

1. Field of the Invention

The invention relates to methods of inhibiting tumor cell proliferation by inhibiting FoxM1B activity. Specifically, the invention relates to methods of inhibiting tumor cell proliferation by inhibiting FoxM1B activity, expression, or nuclear localization in a tumor cell. The invention also relates to screening methods for identifying compounds that can inhibit tumor cell growth by inhibiting FoxM1B activity, expression, or nuclear localization in a tumor cell.

2. Background of the Related Art

The Forkhead box transcription factors have been implicated in regulating cellular longevity and proliferative capacity. Such studies include a finding of increased longevity in *C. elegans* bearing a mutant daf-2 gene, which encodes the worm homolog of the insulin/Insulin-like Growth Factor 1 (IGF1) receptor (Lin et al., 1997, *Science* 278: 1319-1322; Ogg et al., 1997, *Nature* 389: 994-999). Disruption of the daf-2 gene abolishes insulin-mediated activation of the phosphatidylinositol 3-kinase (PI3K)—protein kinase B/Akt (Akt) signal transduction pathway and prevents inhibition of the forkhead transcription factor daf-16 (corresponding to mammalian homologs FoxO1 or Fkhr) (Paradis and Ruvkun, 1998, *Genes Dev.* 12: 2488-2498). Activation of the PI3K/Akt pathway phosphorylates the C-terminus of the Daf-16 (FoxO1; Fkhr) gene product and mediates its nuclear export into the cytoplasm, thus preventing FoxO1 transcriptional activation of target genes (Biggs et al., 1999, *Proc. Natl. Acad. Sci. USA* 96: 7421-7426; Brunet et al., 1999, *Cell* 96: 857-68; Guo et al., 1999, *J. Biol. Chem.* 274: 17184-17192).

More recent studies of Daf-2⁻ *C. elegans* mutants have demonstrated that Daf-16 stimulates expression of genes that limit oxidative stress (Barsyte et al., 2001, *FASEB J.* 15: 627-634; Honda et al., 1999, *FASEB J.* 13: 1385-1393; Wolkow et al., 2000, *Science* 290: 147-150) and that the mammalian FoxO1 gene could functionally replace the Daf-16 gene in *C. elegans* (Lee et al., 2001, *Curr. Biol.* 11: 1950-1957). In proliferating mammalian cells, the PI3K/Akt signal transduction pathway is essential for G1 to S-phase progression because it prevents transcriptional activity of the FoxO1 and FoxO3 proteins, which stimulate expression of the CDK inhibitor p27$^{kip1}$ gene (Medema et al., 2000, *Nature* 404: 782-787). Moreover, genetic studies in budding yeast demonstrated that forkhead Fkh1 and Fkh2 proteins are components of a transcription factor complex that regulates expression of genes critical for progression into mitosis (Hollenhorst et al., 2001, *Genes Dev.* 15: 2445-2456; Koranda et al., 2000, *Nature* 406: 94-98; Kumar et al., 2000, *Curr. Biol.* 10: 896-906; Pic et al., 2000, *EMBO J.* 19: 3750-3761).

Forkhead Box M1B (FoxM1B) transcription factor (also known as Trident and HFH-11B) is a proliferation-specific transcription factor that shares 39% amino acid homology with the HNF-3 winged helix DNA binding domain. The molecule also contains a potent C-terminal transcriptional activation domain that possesses several phosphorylation sites for M-phase specific kinases as well as PEST sequences that mediate rapid protein degradation (Korver et al., 1997, *Nucleic Acids Res.* 25: 1715-1719; Korver et al., 1997, *Genomics* 46: 435-442; Yao et al., 1997, *J. Biol. Chem.* 272: 19827-19836; Ye et al., 1997, *Mol. Cell Biol.* 17: 1626-1641).

In situ hybridization studies have shown that FoxM1B is expressed in embryonic liver, intestine, lung, and renal pelvis (Ye et al., 1997, *Mol. Cell Biol.* 17: 1626-1641). In adult tissue, however, FoxM1B is not expressed in postmitotic, differentiated cells of the liver and lung, although it is expressed in proliferating cells of the thymus, testis, small intestine, and colon (Id). FoxM1B expression is reactivated in the liver prior to hepatocyte DNA replication following regeneration induced by partial hepatectomy (Id).

FoxM1B is expressed in several tumor-derived epithelial cell lines and its expression is induced by serum prior to the $G_1$/S transition (Korver et al., 1997, *Nucleic Acids Res.* 25: 1715-1719; Korver et al., 1997, *Genomics* 46: 435-442; Yao et al., 1997, *J. Biol. Chem.* 272: 19827-19836; Ye et al., 1997, *Mol. Cell Biol.* 17: 1626-1641). Consistent with the role of FoxM1B in cell cycle progression, elevated FoxM1B levels are found in numerous actively-proliferating tumor cell lines (Korver et al., 1997, *Nucleic Acids Res.* 25: 1715-1719; Yao et al., 1997, *J. Biol. Chem.* 272: 19827-36; Ye et al., 1997, *Mol. Cell Biol.* 17: 1626-1641). Increased nuclear staining of FoxM1B was also found in human basal cell carcinomas (Teh et al., 2002, *Cancer Res.* 62: 4773-80), suggesting that FoxM1B is required for cellular proliferation in human cancers.

These studies and others suggest that FoxM1B plays some role in human cancers. FoxM1B, therefore, would provide an attractive target for anti-cancer therapies because FoxM1B expression typically declines during normal aging (see co-owned and co-pending U.S. provisional patent application, Ser. No. 60/426,068, filed Nov. 13, 2002, incorporated by reference herein). Thus, FoxM1B might provide a selective target that is more active in tumor cells than in normal cells, particularly terminally-differentiated, aged or aging normal cells that surround a tumor, allowing tumor cells to be treated while minimizing the deleterious side-effects of such compounds on normal cells.

SUMMARY OF THE INVENTION

The invention provides methods of inhibiting proliferation of a tumor cell, comprising the step of inhibiting FoxM1B activity in the tumor cell. The methods of the invention can be accomplished by regulating FoxM1B activity through any of the mechanisms as described herein, including but not limited to inhibiting FoxM1B-dependent transcription activity by interfering with binding of either Cdk2-Cyclin E/A or Cdk1-Cyclin B complexes, preventing or reducing phosphorylation of Threonine 596 in the FoxM1B protein (both of which will significantly reduce Foxm1b transcriptional activity) or inhibiting nuclear localization of FoxM1B protein.

In one aspect of the invention, cellular FoxM1B activity is inhibited by causing FoxM1B protein to localize in the tumor cell cytoplasm or to localize to the nucleolus of the tumor cell nucleus and/or preventing or inhibiting translocation of FoxM1B to the cell nucleus. Causing FoxM1B protein to localize in the cytoplasm can be accomplished, for example, by contacting a cell with a compound that causes FoxM1B to translocate from the nucleus to the cytoplasm, or that sequesters FoxM1B in the cytoplasm and prevents FoxM1B from translocating from the cytoplasm to the nucleus. Causing FoxM1B protein to localize in the nucleolus of the nucleus can occur when FoxM1B protein interacts with the tumor suppressor $p19^{ARF}$ protein or a peptide containing the $p19^{ARF}$ sequences 26-44 or compounds that mimic $p19^{ARF}$ function. Such compounds can be identified using screening methods of the invention as described herein.

In another aspect, FoxM1B activity can be inhibited by contacting a tumor cell with an antisense oligonucleotide, wherein the antisense oligonucleotide is complementary to nucleic acid sequences of RNA or double-stranded DNA that encodes FoxM1B and which inhibits FoxM1B gene expression. Preferably, an antisense oligonucleotide of the invention comprises a nucleotide sequence that is complementary to nucleotides 1-2700 of FoxM1B cDNA.

In another aspect, FoxM1B activity can be inhibited by contacting a cell, preferably a tumor cell, with a peptide having an amino acid sequence of the $p19^{ARF}$ tumor suppressor protein as set forth in SEQ ID NO: 10 (rrrrrrrrrKFVRSR-RPRTASCALAFVN; referred to herein as the (D-Arg)$_9$-$p19^{ARF}$ 26-44 peptide), SEQ ID NO: 11 (KFVRSRRPRTASCALAFVN; referred to herein as the $p19^{ARF}$ 26-44 peptide), or SEQ ID NO: 12 (KFVRSR-RPRTASCALAFVNMLLRLERIL RR; referred to herein as the $p19^{ARF}$ 26-55 peptide).

In yet another aspect, FoxM1B activity can be inhibited indirectly by interfering with or inhibiting activity of endogenous proteins necessary to activate FoxM1B. For example, FoxM1B activity can be inhibited by interfering with the ability of FoxM1B to interact with p300/CBP or by inhibiting CDK1 phosphorylation of FoxM1B. In addition, a tumor cell can be contacted with a tyrphostin, for example, a Jak2 kinase inhibitor, such as AG490, to inhibit FoxM1B activity. Jak2 kinase inhibitors can inhibit FoxM1B activity by interfering with the ability of growth factors, such as growth hormone, to activate FoxM1B. Other inhibitors of FoxM1B activity are provided in the Examples below, for example, alsterpaullone, Akt inhibitor, U0126, and Ly294002.

The methods of the invention can be used to inhibit growth of any tumor cell that expresses FoxM1B protein or that is derived from a cell that expressed FoxM1B protein. A cell that expressed FoxM1B protein can be, for example, a cell from an aging individual, wherein expression of FoxM1B protein is diminished as a result of aging. In a particular aspect, the methods of the invention can be used to inhibit tumor cell growth in vitro (i.e. under cell culture conditions) or in vivo (i.e. in a live animal). In other aspects, the methods of the invention can be used to inhibit growth of tumor cells that are derived from benign or malignant tumors. In a particular aspect, the tumor cells are of epithelial cell origin, for example, from liver, lung, skin, intestine (small intestine or colon), spleen, prostate, breast, brain, or thymus cells. The tumor cells can also be of mesoderm cell origin, for example, from liver, lung, skin, intestine (small intestine or colon), spleen, prostate, breast, brain, bone marrow or thymus cells.

The invention also provides methods for inhibiting tumor growth in an animal comprising administering to an animal, bearing at least one tumor cell present in its body, a therapeutically effective amount of a FoxM1B inhibitor for a therapeutically effective period of time. In one aspect, the FoxM1B inhibitor can be an antisense oligonucleotide, wherein the antisense oligonucleotide is complementary to nucleic acid sequences of RNA or double-stranded DNA that encodes FoxM1B and which inhibits FoxM1B gene expression. In another aspect, the FoxM1B inhibitor can be a compound that inhibits FoxM1B activity. Such compounds can be identified using screening methods of the invention as described herein. In yet another aspect, the FoxM1B inhibitor can be a peptide having an amino acid sequence as set forth in SEQ ID NO: 10, SEQ ID NO: 11, or SEQ ID NO: 12, for a therapeutically effective period of time. In additional aspects, a combination of peptides that inhibit FoxM1B activity can be administered to the animal. For example, peptides having an amino acid sequence as set forth in SEQ ID NO: 10 can be administered with peptides having an amino acid sequence as set forth in SEQ ID NO: 11 and/or SEQ ID NO: 12. One of skill in the art will recognize that any combination of these peptides can be administered to the animal bearing at least one tumor cell in its body.

The invention also provides screening methods for identifying compounds that prevent tumor progression comprising the steps of: contacting with a candidate compound a plurality of cells comprising a FoxM1B gene, wherein the cells express FoxM1B protein when cultured in vitro; assaying FoxM1B localization in the cells; and identifying a candidate compound when FoxM1B is localized in the cytoplasm and not in the nuclei of cells contacted with the compound but localized in the nuclei of cells not contacted with the compound. In one aspect, the compounds identified in this screening method of the invention can prevent tumor progression (i e inhibit tumor cell proliferation and/or de-differentiation of a tumor cell) in a patient when administered to a patient who has at least one tumor cell present in his body.

The invention further provides screening method for identifying compounds that inhibit tumor progression comprising the steps of: contacting with a candidate compound a plurality of cells comprising a FoxM1B gene, wherein the cells express FoxM1B protein when cultured in vitro; assaying FoxM1B localization in the cells; selecting a candidate compound when FoxM1B is localized in the cytoplasm and not in the nuclei of cells contacted with the compound but localized in the nuclei of cells not contacted with the compound; and identifying a compound as a compound that can inhibit tumor progression if proliferation of tumor cells is inhibited when contacted with the compound.

In addition, the invention provides screening methods for identifying compounds that inhibit nuclear localization of FoxM1B protein, comprising the steps of: contacting a cell with a compound, wherein the cell expresses a green fluorescent protein-FoxM1B (GFP-FoxM1B) fusion protein; contacting the cell with growth hormone; detecting localization of the GFP-FoxM1B protein in the cells; and identifying a compound as a compound that inhibits FoxM1B localization if the GFP FoxM1B protein is localized in the cytoplasm and not the nuclei of the cells.

The invention also provides screening method for identifying compounds that inhibit nuclear localization of FoxM1B protein, comprising the steps of: contacting a transgenic mouse with a compound, wherein the cells of the transgenic mouse express a green fluorescent protein-FoxM1B (GFP-FoxM1B) fusion protein; administering growth hormone to the mouse; detecting localization of the GFP-FoxM1B protein in a cell that is removed from the mouse; and identifying a compound as a compound that inhibits FoxM1B nuclear localization if the GFP-FoxM1B protein is localized in the cytoplasm but not the nucleus of the cell that is removed from the mouse.

The invention also provides screening methods for identifying compounds that inhibit tumor cell proliferation comprising the steps of: expressing a FoxM1B reporter construct in a cell; and detecting FoxM1B activity in the presence and absence of a test compound. A suitable reporter construct is 6X FoxM1B/FoxA TATA-luciferase expression vector described in the Examples below.

In one aspect, a compound can be pre-selected for a screening method of the invention by contacting a plurality of cells with a candidate compound and assaying for cell proliferation, wherein a candidate compound is selected for a screening method of the invention if cell proliferation is inhibited (i.e. the cells proliferate more slowly or not at all in the presence than in the absence of the compound).

In addition, the invention provides methods for identifying compounds that can inhibit FoxM1B transcriptional activity or transformation of a cell, the methods comprising the steps of (a) assaying a cell for FoxM1B transcriptional activity, wherein the cell comprises a FoxM1B expression vector and a reporter gene construct comprising a FoxM1B-responsive transcription control element; and (b) assaying for FoxM1B anchor independent growth by formation of colonies on soft agar using doxycycline inducible GFP-Foxm1b cell line. In preferred embodiments, the FoxM1B expression vector is CMV-FoxM1B cDNA expression vector. In preferred embodiments, the reporter gene is luciferase and the FoxM1B-responsive transcription control element comprises the 6X FoxM1B binding site driving TATA box. In preferred embodiments, these constructs are co-transferred into the cell, either consecutively or simultaneously.

The invention also provides pharmaceutical compositions comprising compounds identified using any of the screening methods of the invention and methods of using the pharmaceutical compositions to inhibit tumor growth in animals. The invention further provides pharmaceutical compositions comprising a peptide having an amino acid sequence as set forth in SEQ ID NO: 10, SEQ ID NO: 11, or SEQ ID NO: 12 or therapeutically-effective mixture thereof. In certain aspects, pharmaceutical compositions of the invention are useful for inhibiting tumor cell growth in an animal by inhibiting FoxM1B activity in the tumor cell.

Specific preferred embodiments of the invention will become evident from the following more detailed description of certain preferred embodiments and the claims.

DETAILED DESCRIPTION OF THE DRAWINGS

FIGS. 1A and 1B depict a human FoxM1B cDNA comprising a deletion of the terminal 972 nucleotides at the 3' end (SEQ ID NO: 1).

FIG. 1C depicts a human FoxM1B protein sequence (SEQ ID NO: 2) encoded by the nucleotide sequence as set forth in SEQ ID NO: 1.

FIGS. 4A and 4B show RNase protection assays (RPA) with a FoxM1B probe after infection of human osteoblastoma U2Os cells with AdFoxM1B AS.

Figure 5:
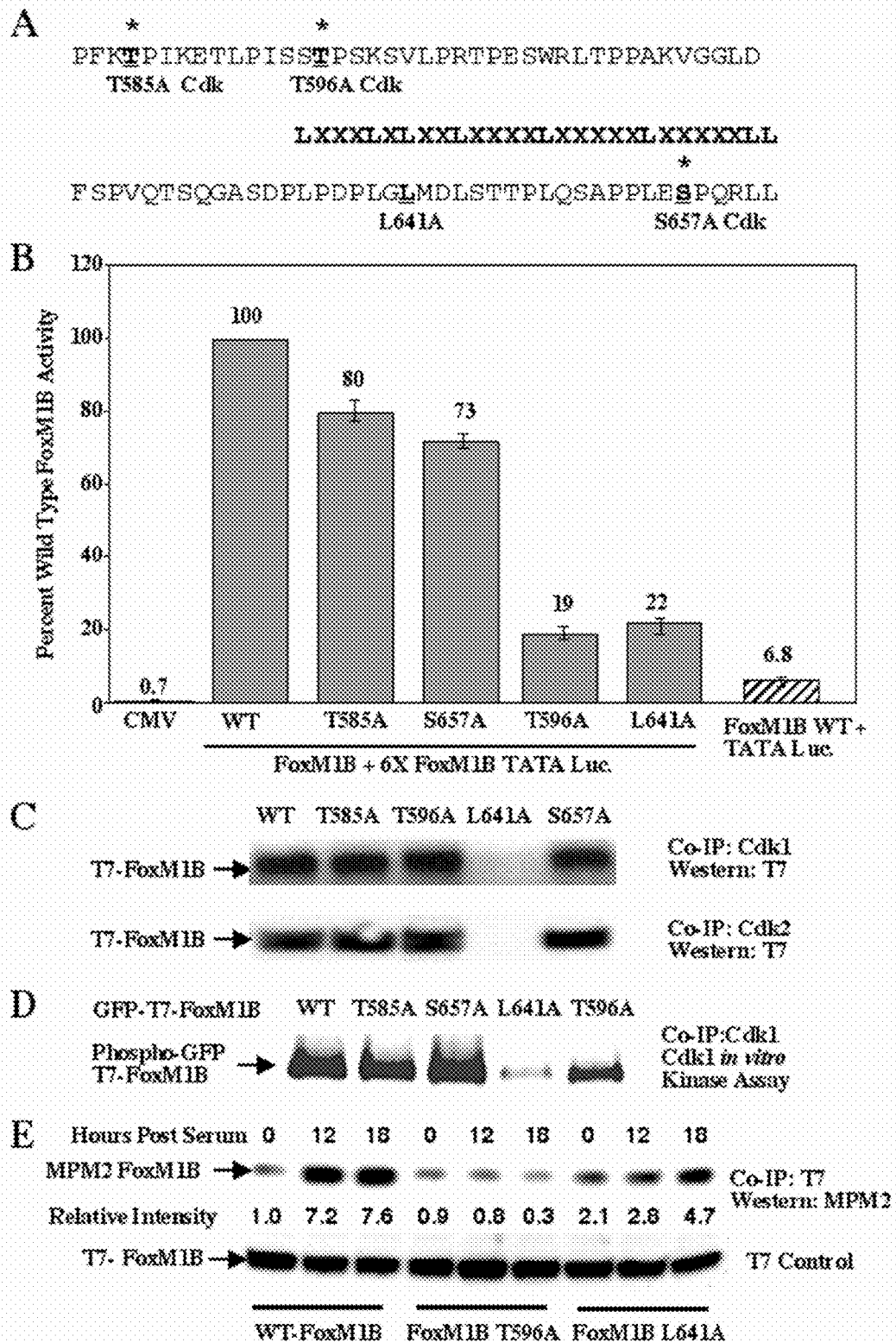

FIG. 5A shows the FoxM1B amino acid sequence from amino acid residue 582-662 (SEQ ID NO: 8) and the LXLXXL (SEQ ID NO: 3) motif, which extends from amino acid residue 635-662 (SEQ ID NO: 9). All of the Thr or Ser residues in the FoxM1B protein sequence that are potential Cdk1/Cdk2 phosphorylation sites were changed to alanine and the Leu residue at 641 in the LXLXXL (SEQ ID NO: 3) motif was changed to alanine.

FIG. 5B depicts a graph showing that mutation of the Cdk1 phosphorylation site at 596 and Leu residue at 641 causes diminished FoxM1B transcriptional activity. Results are expressed as the percent activity with respect to wild-type FoxM1B where CMV-empty served as a control for basal expression levels of the FoxM1B reporter gene. Four separate transfection experiments were performed in triplicate to calculate ±SD.

FIG. 5C shows the results of Western blot analysis with T7 epitope-tagged antibody of U20S cells transiently transfected with CMV-GFP-T7-FoxM1B following immunoprecipitation with a Cdk1 or Cdk2 polyclonal antibody. The immunoprecipitated proteins were subjected to Western blot analysis using a monoclonal antibody against the T7 epitope tagged antibody protein. These co-immunoprecipitation studies showed that the Leu residue at 641 was required for association with the Cdk-Cyclin complexes.

FIG. 5D shows the results of a kinase assay of U20S cells transiently transfected with CMV GFP-FoxM1B (lane1), CMV-GFP-FoxM1B T585A (lane 2), CMV GFP-FoxM1B T596A (lane 3), CMV GFP-FoxM1B L641A (lane 4), or CMV GFP-FoxM1BS657A (lane 5).

FIG. 5E shows diminished in vivo phosphorylation of the FoxM1B T596A Cdk mutant and FoxM1B L641A mutant proteins by the Cdk-Cyclin protein complexes. U20S cells were transiently transfected with either CMV T7-FoxM1B, CMV T7-FoxM1B T596A or FoxM1B L641A, and transfected cells were then serum starved for 48 hours. The cells were then incubated in the presence or absence of serum for 12 or 18 hours, the cells harvested and protein extracts prepared. Protein extracts were immunoprecipitated (IP) with an antibody specific for the T7 epitope and then subjected to Western blot analysis with MPM2 monoclonal antibody that recognizes phosphorylated Cdk sites. Western blot analysis with T7 antibody demonstrated equal amounts of FoxM1B protein in all the lanes. Relative intensity of MPM2 signal was determined and FoxM1B levels from cells not stimulated with serum was set at one.

Figure 6:
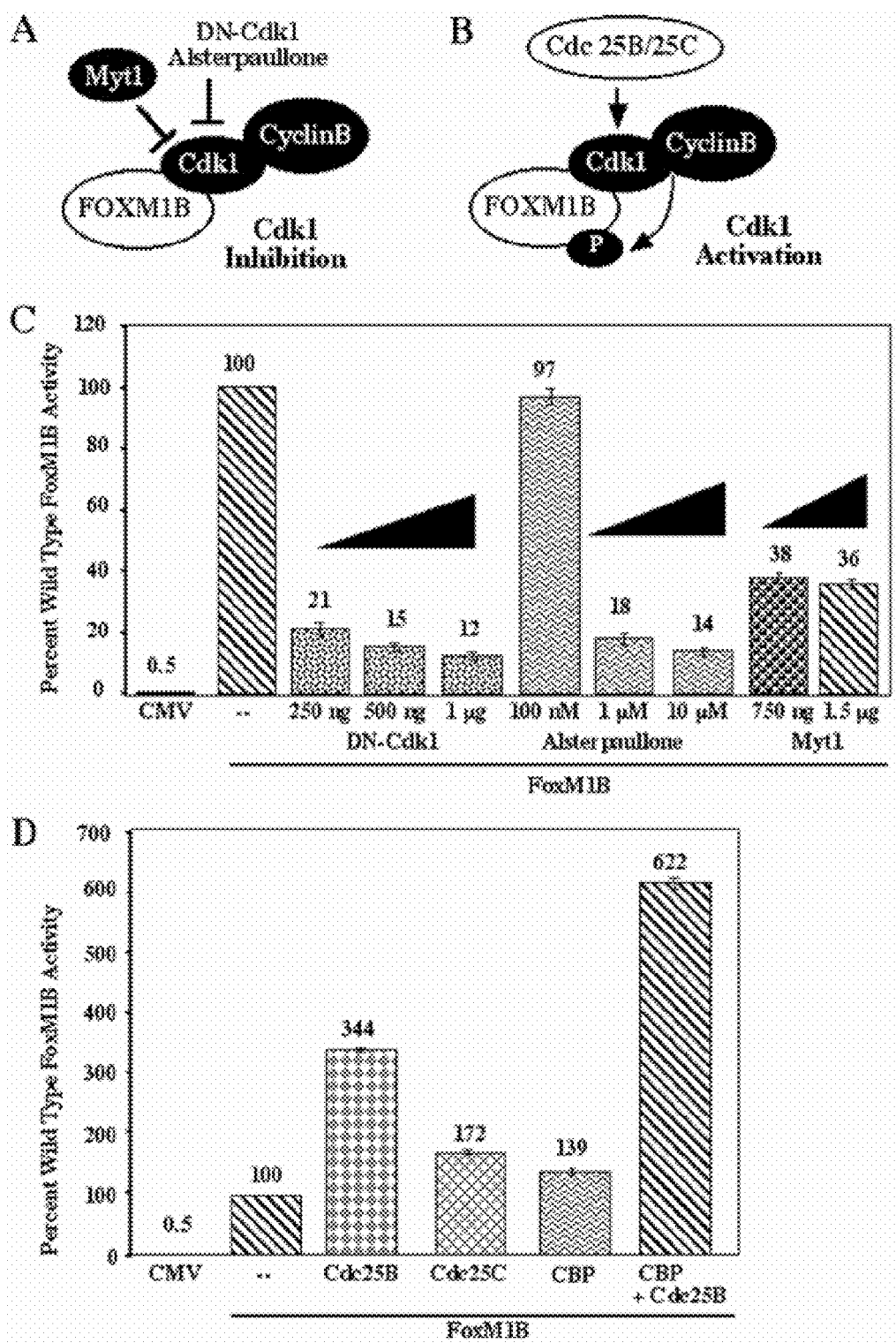
Figure 7:
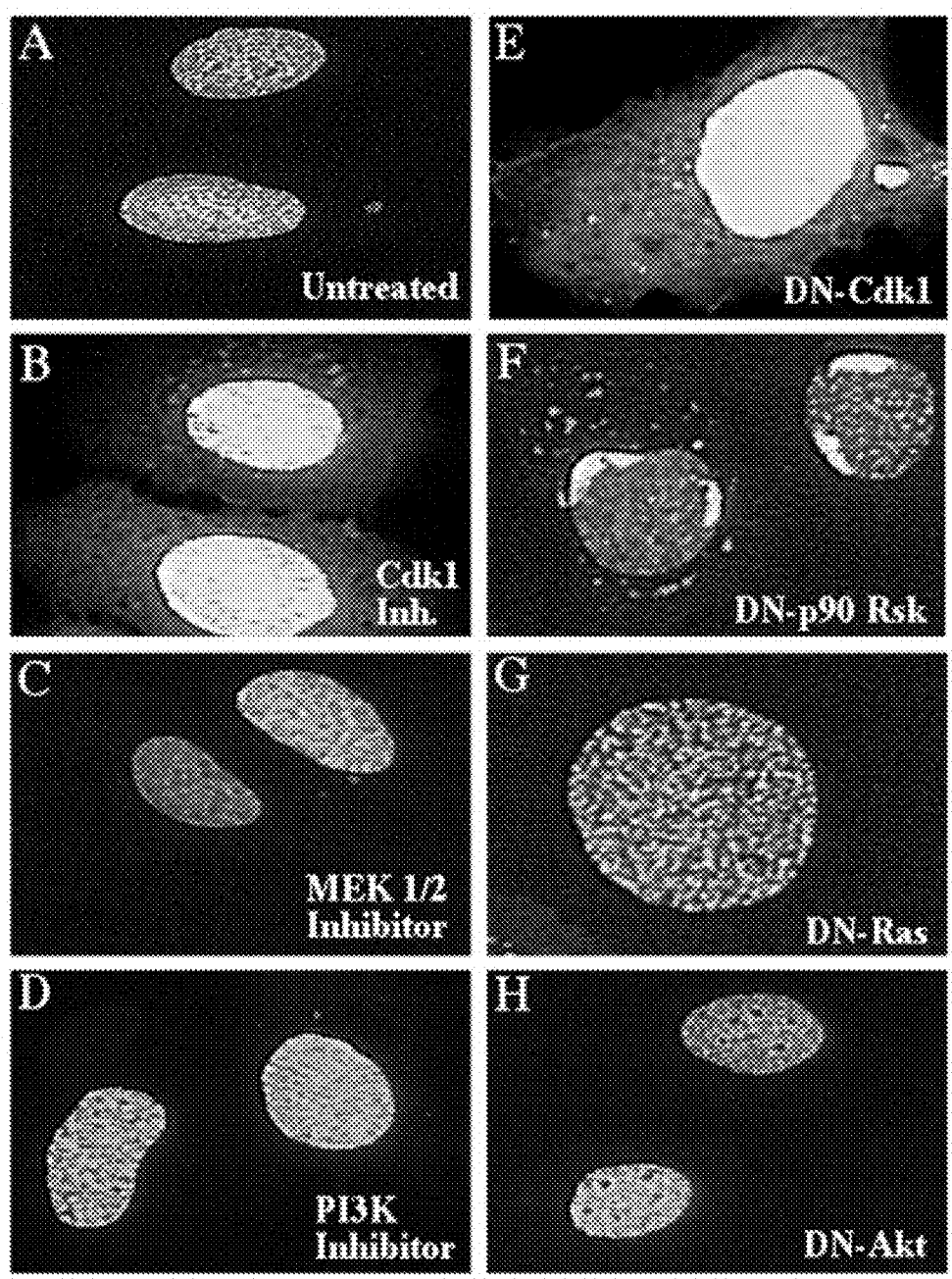

FIG. 6A is a schematic diagram depicting inhibition of Cdk1 kinase activity by either Myt1 phosphorylation, dominant-negative (DN) Cdk1 or the Cdk1 inhibitor Alsterpaullone.

FIG. 6B is a schematic diagram depicting stimulation of Cdk1 activity by Cdc25B and Cdc25C dephosphorylation.

FIG. 6C is a graph demonstrating that inhibition of Cdk1 activity diminished FoxM1B transcriptional activity in cotransfection assays. U20S TetR cells were transiently co-transfected with the reporter 6X-FoxM1B-TATA-Luciferase and CMV-TO-FoxM1B (500 ng) alone or with increasing amounts of either CMV-DN-Cdk1, Cdk1 pharmacological inhibitor Alsterpaullone or CMV-Myt1. Results are expressed as the percent activity with respect to wild-type FoxM1B using four separate transfection experiments were performed in triplicate to calculate ±SD.

FIG. 6D is a graph demonstrating that activation of Cdk1 activity by dephosphorylation with either Cdc25B or Cdc25C stimulated FoxM1B transcriptional activity, which was potentiated by increased CBP levels.

FIGS. 7A-H show nuclear localization of GFP-FoxM1B fusion protein following treatment with either pharmacological kinase inhibitors or dominant negative kinases. U20S cells were transiently transfected with CMV GFP-FoxM1B with the indicated pharmacological kinase inhibitors (B-D) or dominant-negative kinase expression vectors (E-H). Cells in panel (A) were untreated.

Figure 8:
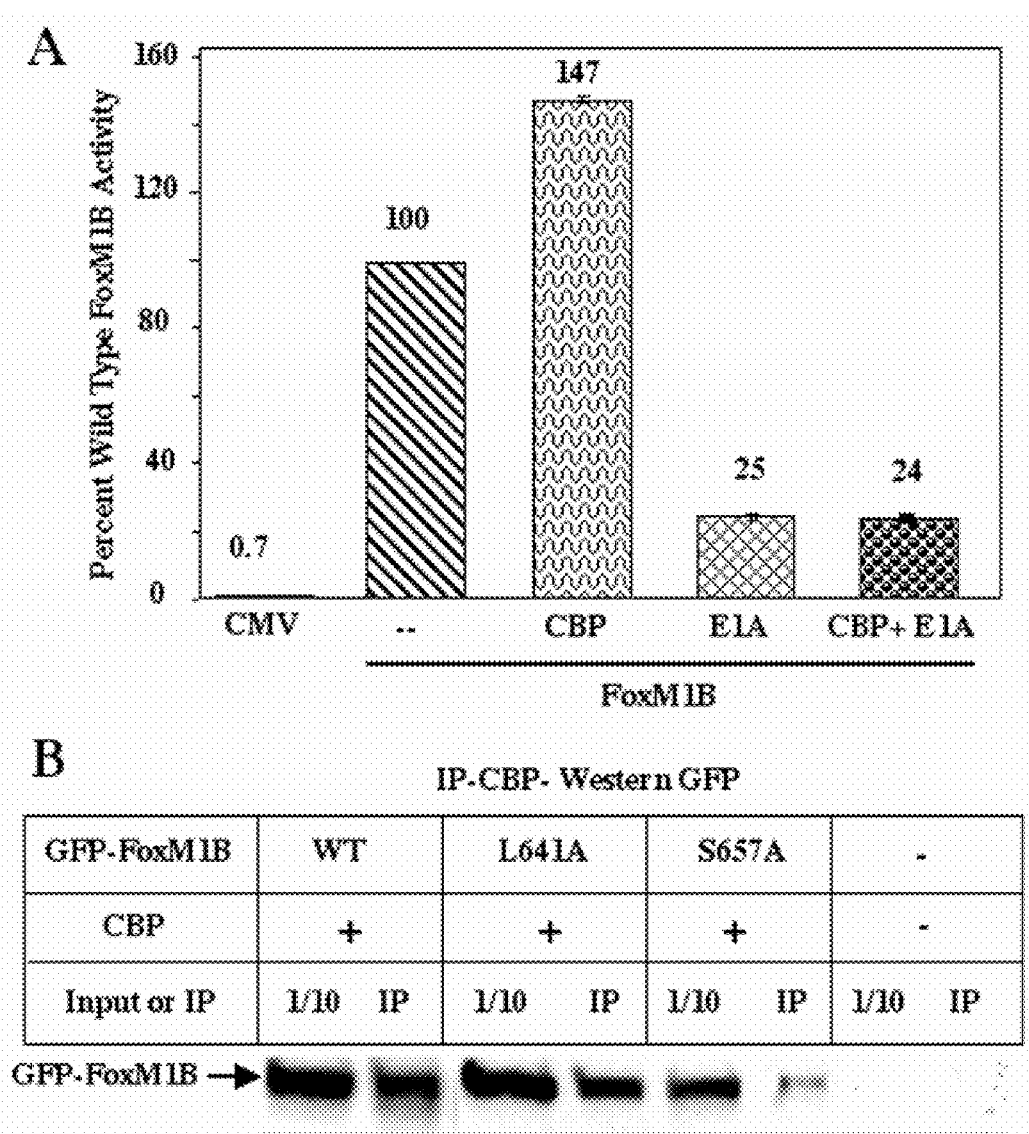

FIG. 8A is a graph demonstrating that inhibition of CBP histone acetyl transferase activity by E1A decreased the FoxM1B transcriptional activity. U20S cells were transiently co-transfected with the reporter 6X-FoxM1B-TATA-Luciferase and CMV-FoxM1B alone or in different combinations with CBP and E1A expression vectors.

FIG. 8B shows the results of Western blot analysis of cell lysates after immunoprecipitation with a monoclonal antibody that recognized CBP. U20S cells were transiently transfected with CBP and either CMV WT GFP-FoxM1B (lanes 1-2), CMV GFP-FoxM1B L641A (lanes 3-4), CMV GFP-FoxM1B S657A (lanes 5-6), or mock transfected (lanes 7-8). The first lane of each set contains 1/10 of the input protein extract (50 ug) and the second lane contains the immunoprecipitated (IP) protein extracts.

Figure 9:
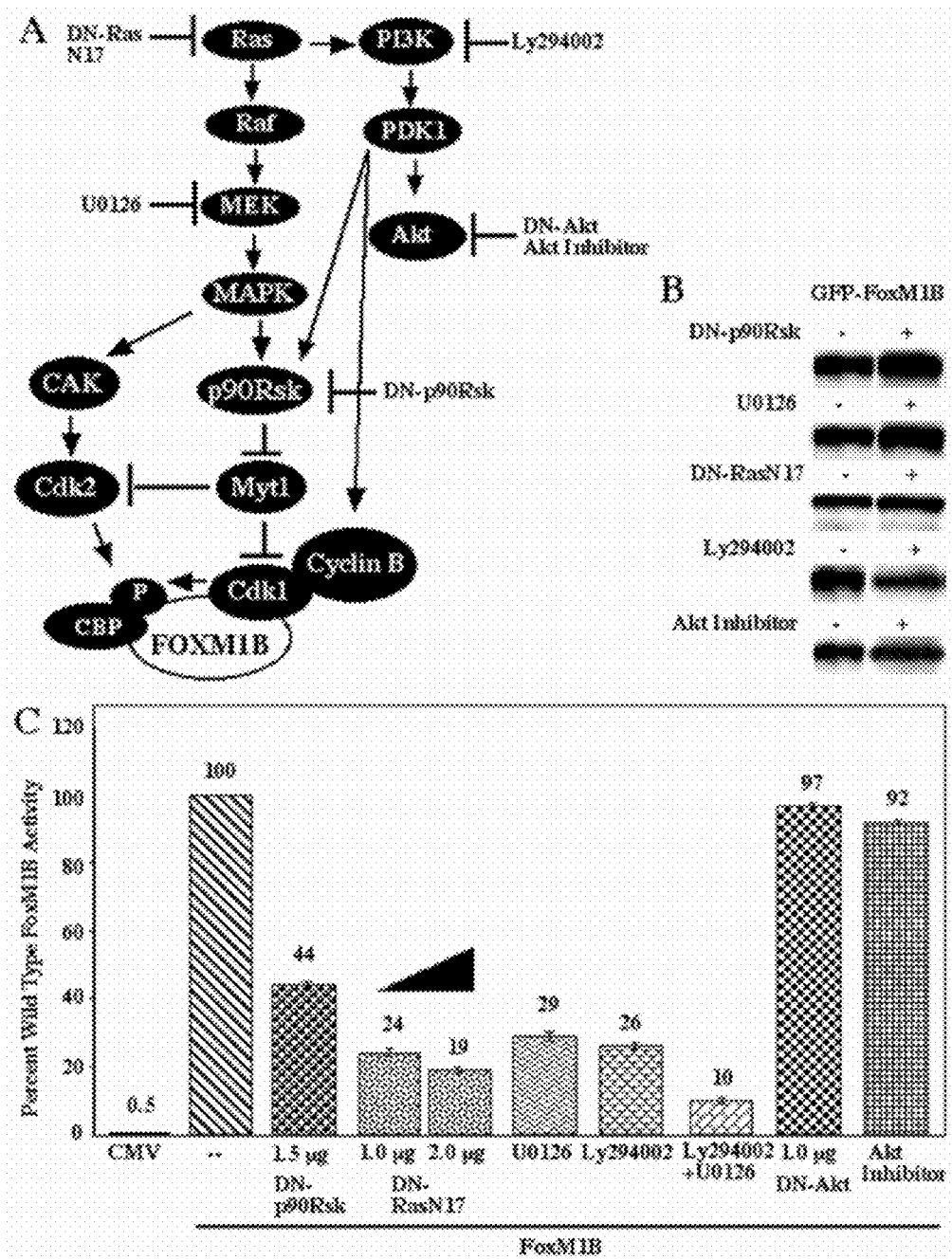

FIG. 9A shows a schematic diagram depicting the Ras/MEK/MAPK/p90Rsk/Myt1 and PI3K/PDK1/p90Rsk/Myt1 pathways, which prevent Myt1 phosphorylation mediated inhibition of Cdk1 activity. Also shown is the action of DN-RasN17, the MEK1/2 inhibitor U0126, PI3K inhibitor Ly294002, DN-Akt and Akt pharmacological kinase inhibitor and DN-p90Rsk.

FIG. 9B shows the results of Western blot analysis with GFP antibody of protein extracts from U20S cells transiently transfected with CMV GFP-FoxM1B plasmid with either CMV DN-p90Rsk or CMV DN-RasN17 or 50 μM of U0126, 50 μM of PI3K inhibitor Ly294002 or 25 μM of Akt inhibitor.

FIG. 9C is a graph demonstrating that inhibition of Ras/MEK/MAPK/p90Rsk and PI3K/PDK1/p90Rsk pathways resulted in diminished FoxM1B transcriptional activity. U20S TetR cells were transiently co-transfected with the reporter 6X-FoxM1B-TATA-Luciferase and CMV-TO-FoxM1B (500 ng) with CMV-DN-p90Rsk, CMV-DN-Ras or DN-AKT or with 50 μM of either U0126 or Ly294002 alone or together or with 25 μM of Akt inhibitor. Four separate transfection experiments were performed in triplicate to calculate ±SD.

Figure 10:
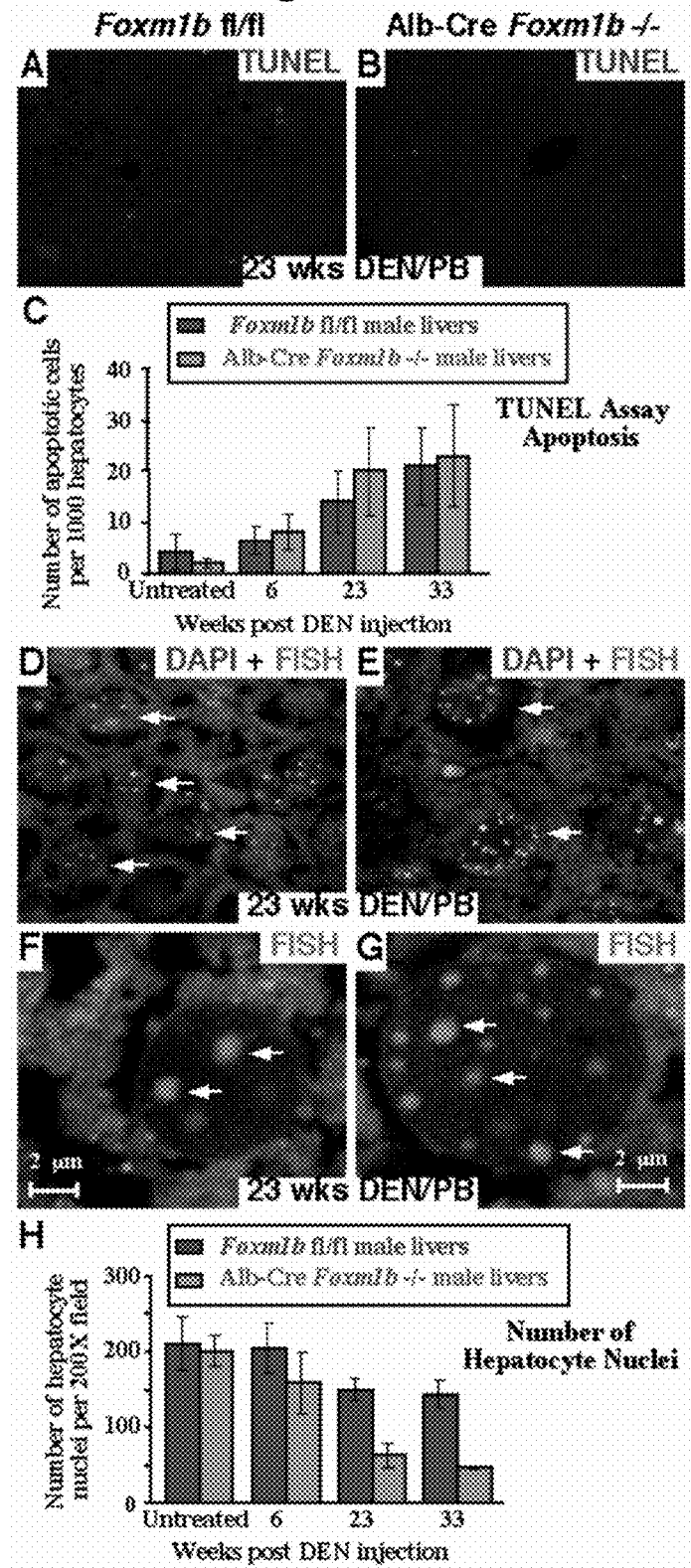

FIGS. 10A-B show fluorescent micrographs of TUNEL assay (100×) demonstrated similar apoptosis levels in Alb-Cre Foxm1b -/- and Foxm1b fl/fl control after 23 weeks of DEN/PB exposure.

FIG. 10C shows a graph of the number of apoptotic cells (TUNEL positive) per 1000 hepatocytes (±SD) in non-tumor regions of livers from male Foxm1b fl/fl or Alb-Cre Foxm1b -/- mice after either 0, 6, 23, or 33 weeks of DEN/PB exposure.

FIGS. 10D-G show high power magnification of hepatocytes in which the nuclei were counterstained with DAPI (630×; D-E) or visualized by Laser Confocal microscopy (F-G; bar indicates 2 μm). A centromere-specific mouse fluorescent in situ hybridization (FISH) probe was used to show that Alb-Cre Foxm1b -/- hepatocyte nuclei possessed an increase in the number of hybridizing chromosomes compared to control hepatocyte nuclei at 23 weeks of DEN/PB treatment.

FIG. 10H is a graph of the mean number of DAPI stained hepatocyte nuclei per 200× field (±SD) in non-tumor regions of livers from male Foxm1b fl/fl or Alb-Cre Foxm1b -/- mice either untreated or after 6, 23, or 33 weeks of DEN/PB exposure. The mean number (±SD) of TUNEL or DAPI positive hepatocyte nuclei per 1000 cells or 200× field was calculated by counting the number of positive hepatocyte nuclei using 5 different liver sections from 3 male mice at the indicated times of DEN/PB exposure.

FIG. 11A-H shows immunohistochemically stained liver sections from Foxm1b fl/fl and Alb-Cre Foxm1b -/- mice either untreated or treated with DEN/PB for either 6, 23 or 33 weeks stained for nuclear expression of FoxM1B protein. Abundant nuclear staining of FoxM1B protein was induced as early as 6 weeks after DEN/PB exposure in Foxm1b fl/fl hepatocytes surrounding the periportal vein (PV, C), but not in hepatocytes near the central vein (CV). High levels of nuclear FoxM1B protein persisted in hyper-proliferative hepatic adenomas and HCC (C and E, margins of tumor indicated by arrows). As expected, nuclear staining of Foxm1b protein was not found in Alb-Cre Foxm1b -/- hepatocytes at any of the time points following DEN/PB treatment (B, D, F and H). Abbreviations are PV, portal vein and CV, central vein. Magnifications are 200×.

FIG. 12A-I shows that Alb-Cre Foxm1b -/- livers exhibit normal expression of GST-pi and CAR following DEN/PB treatment. Alb-Cre Foxm1b -/- and Foxm1b fl/fl livers isolated from male mice after 23 weeks of DEN/PB exposure were immunohistochemically stained with antibody specific to Glutathionine-S-transferase placental isoform (GST-pi). Both Alb-Cre Foxm1b -/- and Foxm1b fl/fl hepatocytes were strongly immunostained for GST-pi after 23 weeks of DEN/PB treatment (C-F) but its expression was not detected in untreated control Foxm1b fl/fl mouse liver (A-B). Western blot analysis with liver protein extracts demonstrated that hepatic expression of GST-pi protein was induced as early as 6 weeks following DEN/PB treatment and that its hepatic expression continued following 23 weeks of DEN/PB exposure (G). Normal hepatocyte nuclear levels of the CAR nuclear receptor were found in male Alb-Cre Foxm1b -/- mice following DEN/PB treatment (H-I). Magnifications: A, C, E is 50×; B, D, F, H, I is 200×.

Figure 13:
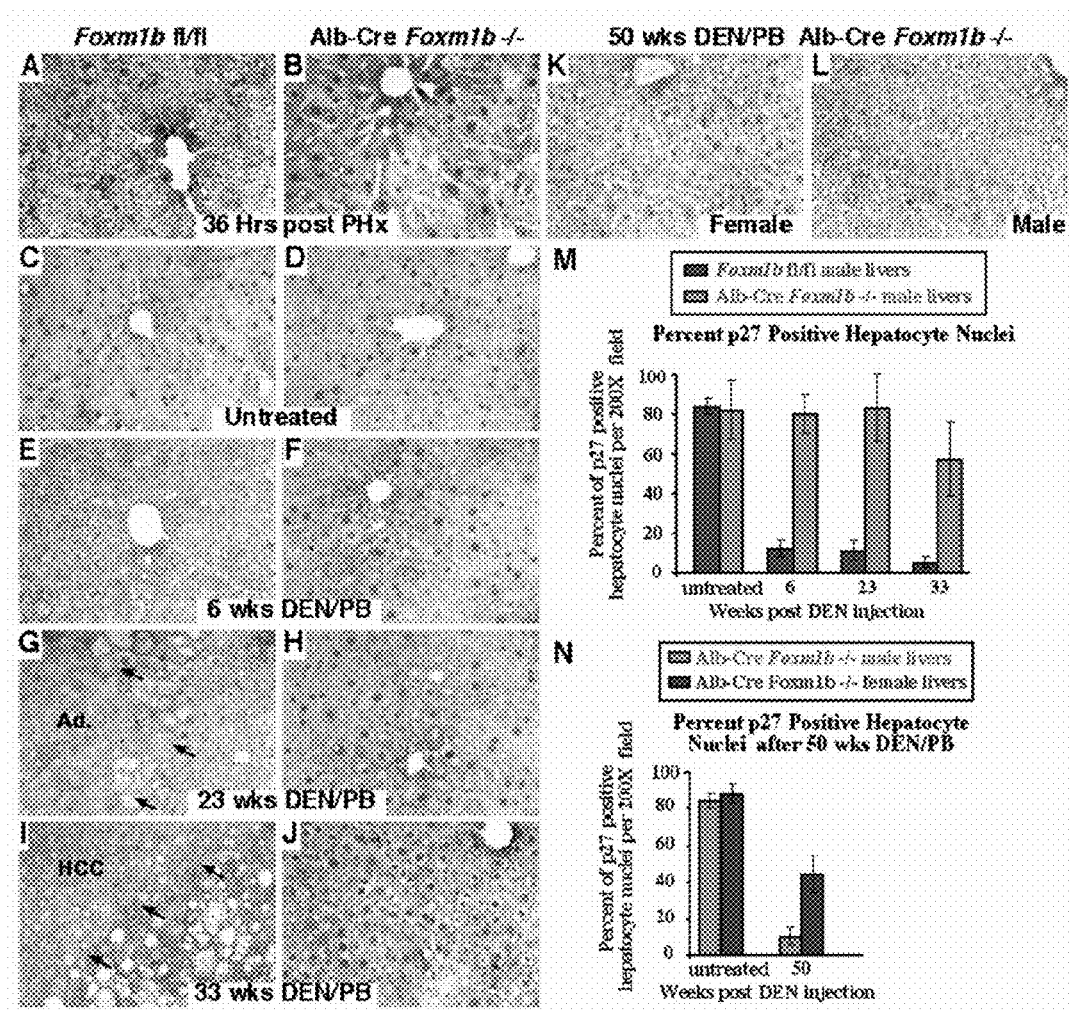

FIGS. 13A-B show $p27^{Kip1}$ immunohistochemical staining of liver sections from untreated Alb-Cre Foxm1b -/- and Foxm1b fl/fl mice.

FIGS. 13C-J show immunohistochemical staining of liver sections from Alb-Cre Foxm1b -/- and Foxm1b fl/fl male mice after either untreated or after 6, 23, or 33 weeks of DEN/PB exposure to examine hepatocyte nuclear expression of $p27^{Kip1}$ protein. In FIGS. 13E and G, the margins of hepatic adenoma (Ad) or hepatocellular Carcinoma (HCC) are indicated by arrows. Magnification: A-J is 200×.

FIG. 13K shows immunohistochemical staining of $p27^{Kip1}$ protein in female Alb-Cre Foxm1b -/- mice hepatocytes after 50 weeks DEN/PB treatment.

FIG. 13L shows immunohistochemical staining of $p27^{Kip1}$ protein in male Alb-Cre Foxm1b -/- mice hepatocytes after 50 weeks of DEN/PB.

FIGS. 13M-N show graphs of percent $p27^{Kip1}$ positive hepatocyte nuclei per 200× field liver section during tumor progression. Number of hepatocyte nuclei per 200× section was determined by DAPI staining.

Figure 14:
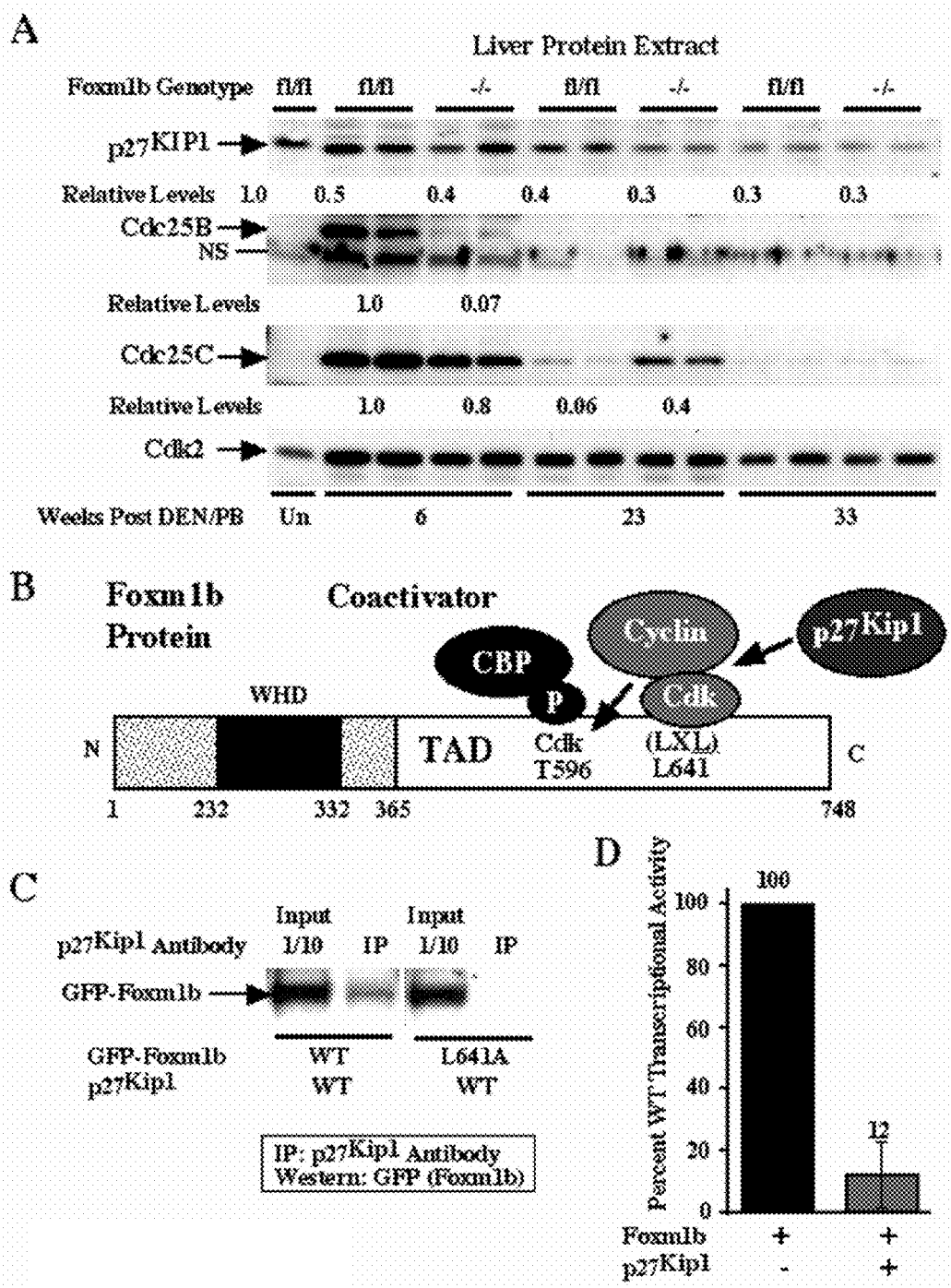

FIG. 14A shows results from Western blot analysis of $p27^{Kip1}$, Cdc25B or Cdc25C protein expression in liver protein extracts isolated from either untreated or DEN/PB treated mice. Expression levels of Cdk2 were used as a loading control.

FIG. 14B is a drawing depicting the FoxM1B winged helix DNA binding domain (WHD), the C-terminal transcriptional activation domain (TAD), and the FoxM1B LXL motif (639-641) that recruits either the Cdk2-Cyclin E/A (S-phase) or Cdk1-Cyclin B (G2 phase) complexes.

FIG. 14C shows co-immunoprecipitation (Co-IP) assays with protein extracts prepared from U2OS cells that were transiently transfected CMV p27$^{Kip1}$ and with CMV expression vectors containing either WT GFP-FoxM1B or GFP-Foxm1b L641A mutant protein that fail to recruit the Cdk-Cyclin complexes. Also shown is a control lane containing 1/10 of the extract used in the Co-IP experiment.

FIG. 14D shows that p27$^{Kip1}$ protein inhibited FoxM1B transcriptional activity in cotransfection assays. Transfections were performed twice in triplicate and used to calculate percent WT FoxM1B transcriptional levels (±SD).

Figure 15:
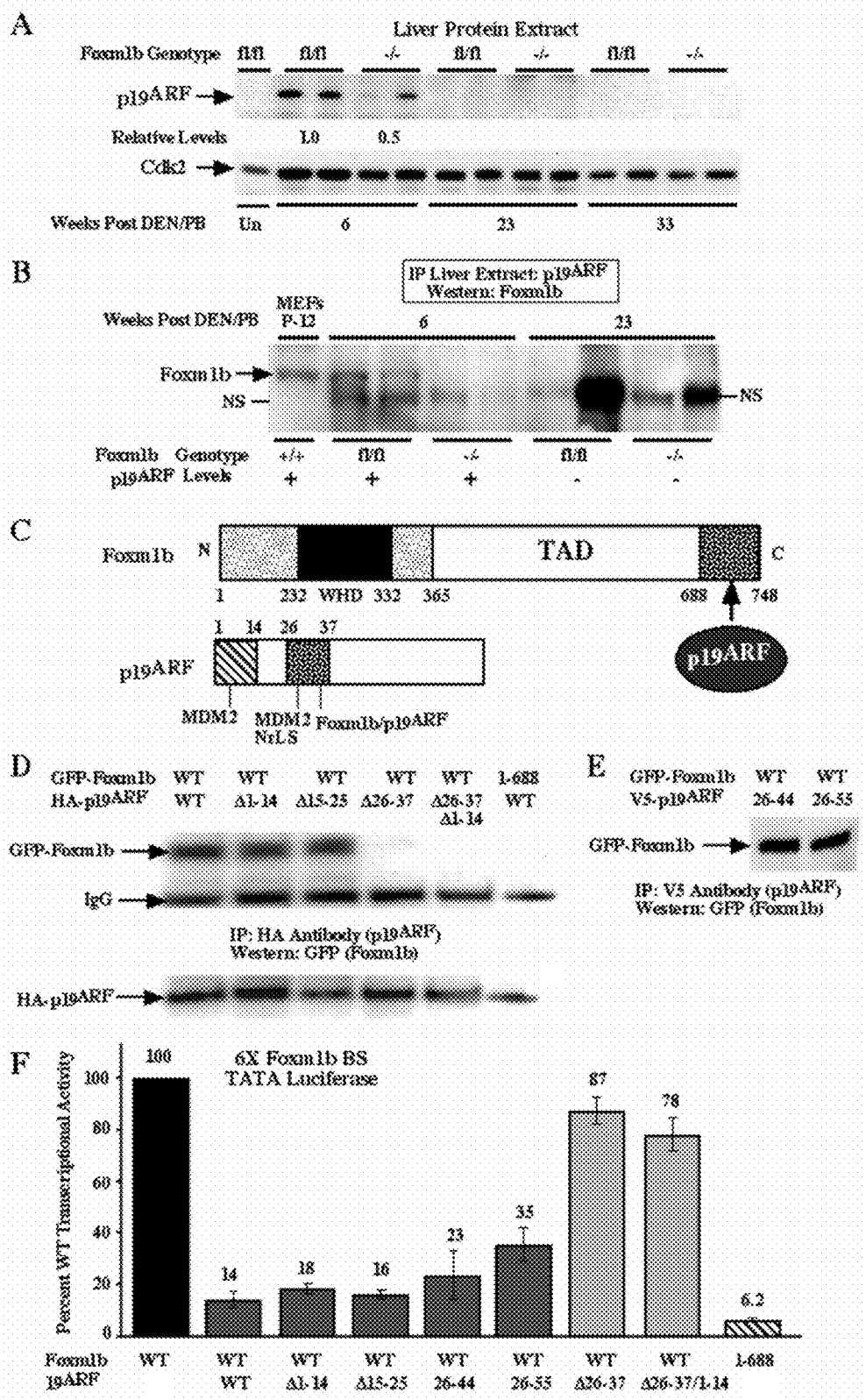

FIG. 15A shows Western Blot analysis, blotting with a p19$^{ARF}$ (p19) antibody, of liver extracts prepared from two mice following either no treatment or 6, 23 and 33 weeks of DEN/PB exposure. Expression levels of Cdk2 were used as a loading control.

FIG. 15B shows co-immunoprecipitation (Co-IP) assays performed with liver protein extracts prepared from Foxm1b fl/fl and Alb-Cre Foxm1b −/− mice following either 6 or 23 weeks of DEN/PB treatment. The protein extracts were first immunoprecipitated with p19 antibody and then analyzed by Western blot analysis with a mouse FoxM1B antibody.

FIG. 15C is a drawing depicting functional domains of the FoxM1B and p19$^{ARF}$ tumor suppressor proteins. Schematically shown is the FoxM1B winged helix DNA binding domain (WHD), the C-terminal transcriptional activation domain (TAD) and the C-terminal region (688-748) required for p19$^{ARF}$ (p19) binding. Schematically shown are the p19 nucleolar localization sequence (NrLS) and the p19 Mdm2 and FoxM1B binding sites.

FIG. 15D shows co-IP assays with protein extracts prepared from U2OS cells that were transiently transfected with CMV green fluorescent protein (GFP)-FoxM1B fusion protein and with p19 expression vectors. These included expression vectors containing either WT p19 protein or N-terminal deletion mutants of the p19 protein (Δ1-14, Δ15-25, Δ26-37, Δ26-37+Δ1-14) that were fused with an hemagglutinin (HA) epitope tag. The p19 protein was immunoprecipitated from transfected protein extracts with HA antibody followed by Western blot analysis with a monoclonal antibody specific to the GFP protein to detect the GFP-FoxM1B fusion protein.

FIG. 15E shows co-IP assays with protein extracts prepared from U2OS cells that were transiently transfected with CMV GFP-FoxM1B fusion protein and expression vector containing V5 epitope tagged p19$^{ARF}$ 26-44 or p19$^{ARF}$ 26-55 sequences. The p19 protein was immunoprecipitated from transfected protein extracts with V5 epitope antibody followed by Western blot analysis with GFP monoclonal antibody.

FIG. 15F shows that the p19 protein inhibits FoxM1B transcriptional activity in cotransfection assays.

FIG. 16A-D shows immunostaining of U2OS cells transfected with HA-p19ARF and GFP-FoxM1B expression vectors demonstrating that the HA tagged p19 was able to target nuclear fluorescence of WT GFP-Foxm1b fusion protein (D) to the nucleolus (B, C).

FIGS. 16E-I shows nucleolar targeting of GFP-FoxM1B WT protein in cotransfections with CMV expression vectors containing mutant p19$^{ARF}$ proteins (Δ1-14, Δ15-25, 26-44 or 26-55) that were still able to associate with FoxM1B protein.

Figure 16:
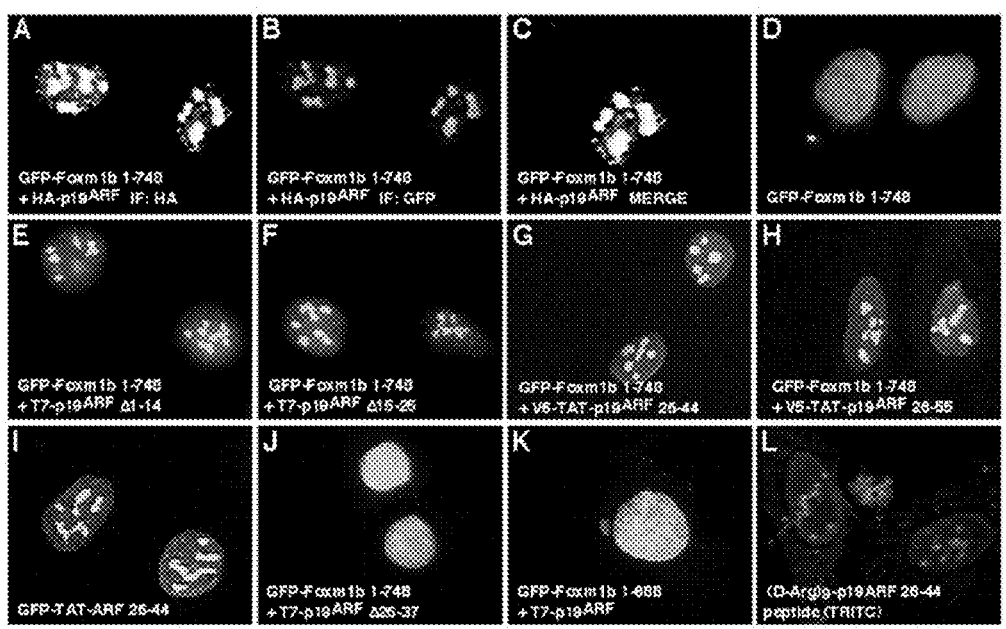

FIG. 16I shows nucleolar fluorescence of CMV GFP-p19$^{ARF}$ 26-44.

FIG. 16J shows nuclear fluorescence of CMV WT GFP-FoxM1B and expression vector containing mutant p19$^{ARF}$Δ26-37 protein that failed to interact with FoxM1B.

FIG. 16K shows transfection of CMV WT p19 expression vector was unable to elicit nucleolar targeting of GFP-FoxM1B 1-688 protein, which failed to bind to p19 protein.

FIG. 16L shows that treatment of U2OS cells for three days with the TRITC fluorescently tagged (D-Arg)$_9$-p19$^{ARF}$ 26-44 peptide demonstrated that this p19$^{ARF}$ peptide was transduced into the cell and was localized to the nucleolus.

Figure 17:
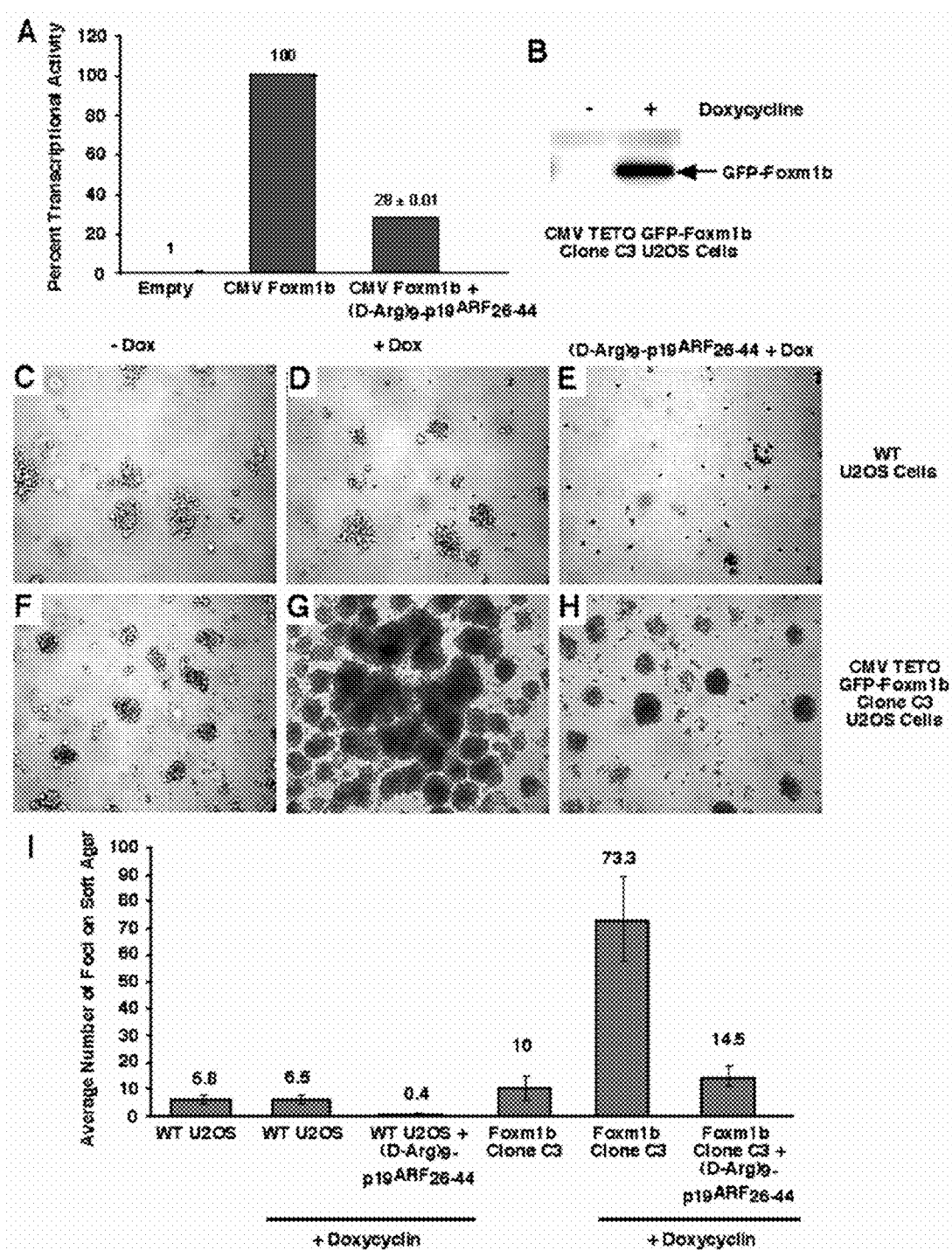

FIG. 17A is a graph showing that the (D-Arg)$_9$-p19$^{ARF}$ 26-44 peptide was an effective inhibitor of FoxM1B transcriptional activity.

FIG. 17B is a Western blot analysis showing that the CMV-TETO GFP-Foxm1b U2OS clone C3 cell line displayed Doxycycline inducible expression of the GFP-FoxM1B fusion protein.

FIG. 17C-H shows results of colony formation assays wherein the (D-Arg)$_9$-p19$^{ARF}$ 26-44 peptide significantly diminished the ability of induced GFP-FoxM1B to stimulate colony formation of the U2OS clone C3 cells on soft agar. Doxycycline induced FoxM1B-GFP expression stimulated anchorage-independent growth in the U2OS clone C3 cell line (F-G) as assessed by propagation for two weeks on soft agar while the (D-Arg)$_9$-p19$^{ARF}$ 26-44 peptide significantly inhibited colony formation of U2OS cells on soft agar (E and H).

FIG. 17I shows a graph depicting quantitation of FoxM1B induced formation of U2OS cell colonies on soft agar treated or not treated with the (D-Arg)$_9$-p19$^{ARF}$ 26-44 peptide. The number of U2OS colonies of the indicated treatments were counted in 4 to 5 different 100× fields and determined the mean number of cell colonies (±SD).

DETAILED DESCRIPTION OF THE PREFERRED EMBODIMENTS

Conventional techniques well known to those with skill in the art were used for recombinant DNA production, oligonucleotide synthesis, and tissue culture and cell transformation (e.g., electroporation, lipofection) procedures. Enzymatic reactions and purification techniques were performed according to manufacturers' specifications or as commonly accomplished in the art or as described herein. The techniques and procedures were generally performed according to conventional methods well known in the art and as described in various general and more specific references that are cited and discussed throughout the present specification. See e.g., Sambrook et al., 2001, MOLECULAR CLONING: A LABORATORY MANUAL, 3d ed., Cold Spring Harbor Laboratory Press, Cold Spring Harbor, N.Y., which is incorporated herein by reference for any purpose. Unless specific definitions are provided, the nomenclature utilized in connection with, and the laboratory procedures and techniques of, molecular biology, genetic engineering, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

Unless otherwise required by context, singular terms shall include pluralities and plural terms shall include the singular.

DEFINITIONS

As utilized in accordance with the present disclosure, the following terms, unless otherwise indicated, shall be understood to have the following meanings:

The term "isolated protein" referred to herein means a protein encoded by a nucleic acid including, inter alia, genomic DNA, cDNA, recombinant DNA, recombinant RNA, or nucleic acid of synthetic origin or some combination thereof, which (1) is free of at least some proteins with which it would normally be found, (2) is essentially free of other proteins from the same source, e.g., from the same cell or species, (3) is expressed by a cell from a different species, (4) has been separated from at least about 50 percent of polynucleotides, lipids, carbohydrates, or other materials with which it is naturally found when isolated from the source cell, (5) is not linked (by covalent or noncovalent interaction) to all or a portion of a polypeptide to which the "isolated protein" is linked in nature, (6) is operatively linked (by covalent or noncovalent interaction) to a polypeptide with which it is not linked in nature, or (7) does not occur in nature. Preferably, the isolated protein is substantially free from other contaminating proteins or polypeptides or other contaminants that are found in its natural environment that would interfere with its therapeutic, diagnostic, prophylactic or research use.

The terms "polypeptide" or "protein" is used herein to refer to native proteins, that is, proteins produced by naturally-occurring and specifically non-recombinant cells, or by genetically-engineered or recombinant cells, and comprise molecules having the amino acid sequence of the native protein, or sequences that have deletions, additions, and/or substitutions of one or more amino acids of the native sequence. The terms "polypeptide" and "protein" specifically encompass FoxM1B protein, or species thereof that have deletions, additions, and/or substitutions of one or more amino acids of FoxM1B having at least one functional property of the FoxM1B protein. In addition, the terms "polypeptide" and "protein" specifically encompass peptides that can inhibit FoxM1B activity, including the (D-Arg)$_9$-p19ARF 26-44 peptide (SEQ ID NO: 10; rrrrrrrrrKFVRSRRPRTAS-CALAFVN), the p19$^{ARF}$ 26-44 peptide (SEQ ID NO: 11; KFVRSRRPRTASCALAFVN), and the p19$^{ARF}$ 26-55 peptide (SEQ ID NO: 12; KFVRSRRPRTASCALAFVNMLL-RLERILRR), or species thereof that have deletions, additions, and/or substitutions of one or more amino acids of SEQ ID NO: 10, SEQ ID NO: 11, or SEQ ID NO: 12 having the ability to inhibit FoxM1B activity.

The term "naturally-occurring" as used herein refers to an object that can be found in nature, for example, a polypeptide or polynucleotide sequence that is present in an organism (including a virus) that can be isolated from a source in nature and which has not been intentionally modified by man. The term "naturally occurring" or "native" when used in connection with biological materials such as nucleic acid molecules, polypeptides, host cells, and the like, refers to materials which are found in nature and are not manipulated by man. Similarly, "recombinant," "non-naturally occurring" or "non-native" as used herein refers to a material that is not found in nature or that has been structurally modified or synthesized by man.

As used herein, the twenty conventional amino acids and their abbreviations follow conventional usage. See IMMUNOLOGY—A SYNTHESIS, 2nd Edition, (E. S. Golub and D. R. Gren, Eds.), 1991, Sinauer Associates, Sunderland, Mass., which is incorporated herein by reference for any purpose. According to certain embodiments, single or multiple amino acid substitutions (in certain embodiments, conservative amino acid substitutions) may be made in the naturally-occurring sequence (in certain embodiments, in the portion of the polypeptide outside the domain(s) forming intermolecular contacts or comprising functional domains). In certain embodiments, a conservative amino acid substitution does not substantially change the structural characteristics of the parent sequence (e.g., a replacement amino acid should not disrupt secondary structure that characterizes the parent or native protein, such as a helix). Examples of art-recognized polypeptide secondary and tertiary structures are described in PROTEINS, STRUCTURES AND MOLECULAR PRINCIPLES (Creighton, Ed.), 1984, W. H. New York: Freeman and Company; INTRODUCTION TO PROTEIN STRUCTURE (Branden and Tooze, eds.), 1991, New York: Garland Publishing; and Thornton et at., 1991, Nature 354: 105, which are each incorporated herein by reference.

Naturally occurring residues may be divided into classes based on common side chain properties: 1) hydrophobic: norleucine, Met, Ala, Val, Leu, Ile; 2) neutral hydrophilic: Cys, Ser, Thr, Asn, Gln; 3) acidic: Asp, Glu; 4) basic: His, Lys, Arg; 5) residues that influence chain orientation: Gly, Pro; and 6) aromatic: Trp, Tyr, Phe.

Conservative amino acid substitutions may encompass non-naturally occurring amino acid residues, which are typically incorporated by chemical peptide synthesis rather than by synthesis in biological systems. These include peptidomimetics and other reversed or inverted forms of amino acid moieties.

In contrast, non-conservative substitutions may involve the exchange of a member of one of these classes for a member from another class. Such substituted residues may be introduced into regions of a protein or polypeptide that are homologous with non-human orthologs thereof, or into the non-homologous regions of the molecule.

In making such changes, according to certain embodiments, the hydropathic index of amino acids may be considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5) (Kyte et al., 1982, J. Mol. Biol. 157:105-131).

The importance of the hydropathic amino acid index in conferring interactive biological function on a protein is understood in the art (see, for example, Kyte et al., 1982, ibid.). It is known that certain amino acids may be substituted for other amino acids having a similar hydropathic index or score and still retain a similar biological activity. In making changes based upon the hydropathic index, in certain embodiments, the substitution of amino acids whose hydropathic indices are within ±2 is included. In certain embodiments, those that are within ±1 are included, and in certain embodiments, those within ±0.5 are included.

It is also understood in the art that the substitution of like amino acids can be made effectively on the basis of hydrophilicity, particularly where the biologically functional protein or peptide thereby created is intended for use in immunological embodiments, as in the present case. In certain embodiments, the greatest local average hydrophilicity of a protein, as governed by the hydrophilicity of its adjacent amino acids, correlates with its immunogenicity and antigen-binding or immunogenicity, i.e., with a biological property of the protein.

As described in U.S. Pat. No. 4,554,101, the following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, in certain embodiments, the substitution of amino acids whose hydrophilicity values are within ±2 is included, in certain embodiments, those that are within ±1 are included, and in certain embodiments, those within ±0.5 are included.

Exemplary amino acid substitutions are set forth in Table 1.

TABLE 1

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, Gln, Asn, 1,4 Diamine-butyric Acid | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan can determine suitable variants of the polypeptide as set forth herein using well-known techniques. In certain embodiments, one skilled in the art can identify suitable areas of the molecule that can be changed without destroying activity by targeting regions not believed to be important for activity. In certain embodiments, one can identify residues and portions of the molecules that are conserved among similar polypeptides. In certain embodiments, even areas that are important for biological activity or for structure can be subject to conservative amino acid substitutions without destroying the biological activity or without adversely affecting the polypeptide structure.

Additionally, one skilled in the art can review structure-function studies identifying residues in similar polypeptides that are important for activity or structure. In view of such a comparison, one can predict the importance of amino acid residues in a protein that correspond to amino acid residues important for activity or structure in similar proteins. One skilled in the art may opt for chemically similar amino acid substitutions for such predicted important amino acid residues.

One skilled in the art can also analyze the three-dimensional structure and amino acid sequence in relation to that structure in similar polypeptides. In view of such information, one skilled in the art can predict the alignment of amino acid residues of a polypeptide with respect to its three dimensional structure. In certain embodiments, one skilled in the art may choose not to make radical changes to amino acid residues predicted to be on the surface of the protein, since such residues may be involved in important interactions with other molecules. Moreover, one skilled in the art may generate test variants containing a single amino acid substitution at each desired amino acid residue. The variants can then be screened using activity assays known to those skilled in the art. Such variants can be used to gather information about suitable variants. For example, if it was discovered that a change to a particular amino acid residue resulted in destroyed, undesirably reduced, or unsuitable activity, variants with such a change can be avoided. In other words, based on information gathered from such routine experiments, one skilled in the art can readily determine the amino acids where further substitutions should be avoided either alone or in combination with other mutations.

Stereoisomers (e.g., D-amino acids) of the twenty conventional amino acids, non-naturally occurring amino acids such as α-,α-disubstituted amino acids, N-alkyl amino acids, lactic acid, and other unconventional amino acids may also be suitable components for polypeptides of the present invention. Examples of unconventional amino acids include but are not limited to: 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Peptide analogs are commonly used in the pharmaceutical industry as non-peptide drugs with properties analogous to those of the template peptide. These types of non-peptide compound are termed "peptide mimetics" or "peptidomimetics." (See Fauchere, 1986, $Adv. Drug Res.$ 15: 29; Veber and Freidinger, 1985, $TINS$ p. 392; and Evans et al., 1987, $J. Med. Chem.$ 30: 1229, which are incorporated herein by reference for any purpose.) Such compounds are often developed with the aid of computerized molecular modeling. Peptide mimetics that are structurally similar to therapeutically useful peptides may be used to produce a similar therapeutic or prophylactic effect. Generally, peptidomimetics are structurally similar to a paradigm polypeptide (i.e., a polypeptide that has a biochemical property or pharmacological activity), but have one or more peptide linkages optionally replaced by a linkage such as: $-CH_2NH-$, $-CH_2S-$, $-CH_2-CH_2-$, $-CH=CH-$ (cis and trans), $-COCH_2-$, $-CH(OH)CH_2-$, and $-CH_2SO-$, by methods well known in the art. Systematic substitution of one or more amino acids of a consensus sequence with a D-amino acid of the same type (e.g., D-lysine in place of L-lysine) may be used in certain embodiments to generate more stable peptides. In addition, conformationally-constrained peptides comprising a consensus sequence or a substantially identical consensus sequence variation may be generated by methods known in the art (Rizo and Gierasch, 1992, $Ann. Rev. Biochem.$ 61: 387), incorporated herein by reference for any purpose); for example, by adding internal cysteine residues capable of forming intramolecular disulfide bridges which cyclize the peptide.

As used herein, the term "isolated polynucleotide" as used herein means a polynucleotide of genomic, cDNA, or synthetic origin or a combination thereof, which by virtue of its source the "isolated polynucleotide" (1) is not associated with all or a portion of a polynucleotide in which the "isolated polynucleotide" is found in nature, (2) is linked to a polynucleotide which it is not linked to in nature, or (3) does not occur in nature as part of a larger sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

The term "polynucleotide" as used herein means a polymeric form of nucleotides that are at least 10 bases in length. In certain embodiments, the bases may be ribonucleotides or deoxyribonucleotides or a modified form of either type of nucleotide. The term includes single and double stranded forms of DNA.

The term "oligonucleotide" as used herein includes naturally occurring, and modified nucleotides linked together by naturally occurring, and/or non-naturally occurring oligonucleotide linkages. Oligonucleotides are a polynucleotide subset generally comprising no more than 200 nucleotides. In certain embodiments, oligonucleotides are 10 to 60 nucleotides in length. In certain embodiments, oligonucleotides are 12, 13, 14, 15, 16, 17, 18, 19, or 20 to 40 bases in length. Oligonucleotides are single stranded, e.g. for use in the construction of a gene mutant using site directed mutagenesis techniques. Oligonucleotides of the invention may be sense or antisense oligonucleotides.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotides linkages such as phosphate, phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.* 14: 9081; Stec et al., 1984, *J. Am. Chem. Soc.* 106: 6077; Stein et al., 1988, *Nucl. Acids Res.* 16: 3209; Zon et al., 1991, *Anti-Cancer Drug Design* 6: 539; Zon et al., 1991, OLIGONUCLEOTIDES AND ANALOGUES: A PRACTICAL APPROACH, (F. Eckstein, ed.), Oxford University Press, Oxford England, pp. 87-108; Stec et al., U.S. Pat. No. 5,151,510; Uhlmann and Peyman, 1990, *Chemical Reviews* 90: 543, the disclosures of each of which are hereby incorporated by reference for any purpose. An oligonucleotide can include a detectable label, such as a radiolabel, a fluorescent label, an antigenic label or a hapten.

The phrase "recombinant nucleic acid construct" as used herein refers to a DNA or RNA sequence that comprises a coding sequence that is operatively linked to a control sequence. A recombinant nucleic acid construct of the invention is capable of expressing a protein that is encoded by the coding sequence when introduced into a cell. A recombinant nucleic acid construct of the invention preferably comprises the nucleic acid sequence that encodes a protein as set forth in SEQ ID NO: 2, such as the nucleic acid sequence as set forth in SEQ ID NO: 1, whereby a cell contacted with the recombinant nucleic acid construct expresses FoxM1B protein. The term "operatively linked" as used herein refers to components that are in a relationship permitting them to function in their intended or conventional manner. For example, a control sequence "operatively linked" to a coding sequence is ligated thereto in such a way that expression of the coding sequence is achieved under conditions compatible with the control sequences.

The term "control sequence" or "control element" as used herein refers to polynucleotide sequences that can effect the expression and processing of coding sequences to which they are ligated. The nature of such control sequences may differ depending upon the host organism. According to certain embodiments, control sequences for prokaryotes may include promoters, repressors, operators, ribosomal binding sites, and transcription termination sequences and antisense mRNA. According to certain embodiments, control sequences for eukaryotes may include promoters, enhancers and transcription termination sequences, or sequences that regulate protein degradation, mRNA degradation, nuclear localization, nuclear export, cytoplasmic retention, protein phosphorylation, protein acetylation, protein sumolation, or RNA inhibition (RNAi). In certain embodiments, "control sequences" can include leader sequences and/or fusion partner sequences. "Control sequences" are "operatively linked" to a coding sequence when the "control sequence" effects expression and processing of coding sequences to which they are ligated. In one embodiment, a control sequence or control element can be a FoxM1B-responsive transcription control element that comprises the 6X FoxM1B binding site driving TATA box, as described in the Examples below.

As used herein, the phrase "tissue specific promoters" refers to nucleic acid sequences that are capable of directing transcription of a coding sequence and that are activated specifically within a specific cell type. For example, liver specific promoters that drive expression of genes in liver cells include, but are not limited to, human or mouse α1-antitrypsin, albumin promoter, serum amyloid A, transthyretin, hepatocyte nuclear factor 6, and major urinary protein (MUP).

The term "vector" is used to refer to any molecule (e.g., nucleic acid, plasmid, or virus) used to transfer coding information to a host cell or a target cell. Viral vectors suitable for the methods of the invention include those derived from, for example, an adenovirus, an adeno-associated virus, a retrovirus, a herpes simplex virus, or a vaccinia virus.

The term "expression vector" refers to a vector that is suitable for transformation of a host cell or a target cell and contains nucleic acid sequences that direct and/or control the expression of inserted heterologous nucleic acid sequences. Expression includes, but is not limited to, processes such as transcription, translation, and RNA splicing, if introns are present. In one embodiment, an expression vector of the invention is a CMV-FoxM1B cDNA, as described in the Examples below.

The term "host cell" is used to refer to a cell into which has been introduced, or that is capable of having introduced, a nucleic acid sequence and then of expressing a gene of interest. The term includes the progeny of the parent cell, whether or not the progeny is identical in morphology or in genetic make-up to the original parent, so long as the gene is present. In preferred embodiments, the host cell is a eukaryotic cell, more preferably a mammalian cell and most preferably a rodent or human cell.

The term "transduction" is used to refer to the transfer of genes from one bacterium to another, usually by a phage. "Transduction" also refers to the acquisition and transfer of eukaryotic cellular sequences by viruses such as retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, *Virology* 52: 456; Sambrook et al., 2001, MOLECULAR CLONING: A LABORATORY MANUAL, 3d ed., Cold Spring Harbor Laboratory Press, Cold Spring Harbor, N.Y.; Davis et al., 1986, BASIC METHODS IN MOLECULAR BIOLOGY (Elsevier); and Chu et al., 1981, *Gene* 13:

197. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, may be maintained transiently as an episomal element without being replicated, or may replicate independently as a plasmid. A cell is stably transformed when the DNA is replicated with the division of the cell.

In certain embodiments, methods of the invention comprise the step of expressing FoxM1B protein in a host cell or a target cell by introducing into the cell a recombinant nucleic acid construct of the invention. According to such embodiments, the cells are transformed with the recombinant nucleic acid construct using any method for introducing polynucleotides into a host cell or a target cell, including, for example packaging the polynucleotide in a virus (or into a viral vector) and transducing a host cell or a target cell with the virus (or vector), or by transfection procedures known in the art, as exemplified by U.S. Pat. Nos. 4,399,216, 4,912,040, 4,740,461, and 4,959,455 (which patents are hereby incorporated herein by reference for any purpose). In certain embodiments, the transformation procedure used may depend upon the cell to be transformed. Methods for introduction of heterologous polynucleotides into mammalian cells are well known in the art and include, but are not limited to, dextran-mediated transfection, calcium phosphate precipitation, polybrene mediated transfection, protoplast fusion, electroporation, encapsulation of the polynucleotide(s) in liposomes, mixing nucleic acid with positively-charged lipids, and direct microinjection of the DNA into cells and cell nuclei.

Recombinant nucleic acid constructs of the invention typically comprise a nucleic acid molecule encoding all or a functional portion of the amino acid sequence of FoxM1B protein that is inserted into an appropriate expression vector using conventional recombinant genetic techniques. Preferably, the recombinant nucleic acid construct of the invention comprises the nucleic acid sequence that encodes a protein as set forth in SEQ ID NO: 2. The vector is typically selected to be functional in the particular host cell or target cell employed (i.e., the vector is compatible with the host cell or the target cell machinery, permitting amplification and/or expression of the gene). For a review of expression vectors, see Nolan and Shatzman, 1998, Curr. Opin. Biotechnol. 9:447-450.

Typically, expression vectors used in any of the host cells or target cells contain sequences for vector maintenance and for cloning and expression of exogenous nucleotide sequences. Such sequences, collectively referred to as "flanking sequences" in certain embodiments will typically include one or more of the following nucleotide sequences: a promoter, one or more enhancer sequences, an origin of replication, a transcriptional termination sequence, a complete intron sequence containing a donor and acceptor splice site, a sequence encoding a leader sequence for polypeptide secretion, a ribosome binding site, a polyadenylation signal sequence, a polylinker region comprising one or a plurality of restriction endonuclease sites for inserting nucleic acid encoding the polypeptide to be expressed, and a selectable marker element. Each of these sequences is discussed below.

Flanking sequences may be homologous (i.e., from the same species and/or strain as the host cell or the target cell), heterologous (i.e., from a species other than the host cell or the target cell species or strain), hybrid (i.e., a combination of flanking sequences from more than one source), synthetic or native. As such, the source of a flanking sequence may be any prokaryotic or eukaryotic organism, any vertebrate or invertebrate organism, or any plant, provided that the flanking sequence is functional in, and can be activated by, the host cell or the target cell machinery.

Flanking sequences useful in the vectors of this invention may be obtained by any of several methods well known in the art. Typically, flanking sequences useful herein will have been previously identified by mapping and/or by restriction endonuclease digestion and can thus be isolated from the proper tissue source using the appropriate restriction endonucleases. In some cases, the full nucleotide sequence of a flanking sequence may be known. The flanking sequence also may be synthesized using the methods described herein for nucleic acid synthesis or cloning.

Where all or only a portion of the flanking sequence is known, it may be obtained using in vitro amplification methods such as polymerase chain reaction (PCR) and/or by screening a genomic library with a suitable oligonucleotide and/or flanking sequence fragment from the same or another species. Where the flanking sequence is not known, a fragment of DNA containing a flanking sequence may be isolated from a larger piece of DNA that may contain, for example, a coding sequence or even another gene or genes. Isolation may be accomplished by restriction endonuclease digestion to produce the proper DNA fragment followed by isolation using agarose gel purification, Qiagen® column chromatography (Chatsworth, Calif.), or other methods known to the skilled artisan. The selection of suitable enzymes to accomplish this purpose is readily apparent to one of ordinary skill in the art.

Optionally, the vector may contain a "tag"-encoding sequence, i.e., an oligonucleotide molecule located at the 5' or 3' end of the FoxM1B polypeptide coding sequence, wherein such an oligonucleotide sequence encodes polyHis (such as hexaHis), or another "tag" for which commercially available antibodies exist, such as FLAG, HA (hemaglutinin influenza virus), or myc. This tag oligonucleotide is typically ligated to the coding sequence "in frame" so that the tag is fused to the polypeptide upon expression of the polypeptide, and can serve as a means for affinity purification of the FoxM1B polypeptide from the host cell or the target cell. Affinity purification can be accomplished, for example, by column chromatography using antibodies against the tag as an affinity matrix. Optionally, the tag can subsequently be removed from the purified FoxM1B polypeptide by various means such as using certain peptidases for cleavage. In preferred embodiments of such vectors permitting removal of the tag, a protease cleavage site is included in the tag sequence in a position between the tag and polypeptide amino acid sequences when the tagged polypeptide is expressed.

In some cases, for example where glycosylation is desired in a eukaryotic host cell expression system, various presequences can be manipulated to improve glycosylation or yield. For example, the peptidase cleavage site of a particular signal peptide can be altered, or pro-sequences added, which also may affect glycosylation. The final protein product may have, in the −1 position (relative to the first amino acid of the mature protein) one or more additional amino acids incident to expression, which may not have been totally removed. For example, the final protein product may have one or two amino acid residues found in the peptidase cleavage site, attached to the amino-terminus. Alternatively, use of some enzyme cleavage sites may result in a slightly truncated yet active form of the desired polypeptide, if the enzyme cuts at such area within the mature polypeptide.

A transcription termination sequence is typically located 3' to the end of a polypeptide-coding region and serves to terminate transcription. Usually, a transcription termination sequence in prokaryotic cells is a G-C rich fragment followed by a poly-T sequence. While the sequence is easily cloned from a library or even purchased commercially as part of a vector, it can also be readily synthesized using methods for nucleic acid synthesis such as those described herein. In eukaryotes, the sequence AAUAAA (SEQ ID NO: 7) functions both as a transcription termination signal and as a poly A signal required for endonuclease cleavage followed by the addition of poly A residues (usually consisting of about 200 A residues).

A selectable marker gene element encodes a protein necessary for the survival and growth of a host cell or a target cell grown in a selective culture medium. Typical selection marker genes encode proteins that (a) confer resistance to antibiotics or other toxins, e.g., ampicillin, tetracycline, or kanamycin for prokaryotic host cells; (b) complement auxotrophic deficiencies of the cell; or (c) supply critical nutrients not available from complex media. Preferred selectable markers are the kanamycin resistance gene, the ampicillin resistance gene, and the tetracycline resistance gene. A bacterial neomycin resistance gene can also be used most advantageously for selection in both prokaryotic and eukaryotic cells.

The expression and cloning vectors of the present invention will typically contain a promoter that is recognized by the host organism and operatively linked to nucleic acid encoding the FoxM1B protein. Promoters are untranscribed sequences located upstream (i.e., 5') to the start codon of a structural gene (generally within about 100 to 1000 bp) that control transcription of the structural gene. Promoters are conventionally grouped into one of two classes: inducible promoters and constitutive promoters. Inducible promoters initiate increased levels of transcription from DNA under their control in response to some change in culture conditions, such as the presence or absence of a nutrient or a change in temperature. Constitutive promoters, on the other hand, initiate continual gene product production; that is, there is little or no experimental control over gene expression. A large number of promoters, recognized by a variety of potential host cells or target cells, are well known. A suitable promoter is operatively linked to the DNA encoding FoxM1B protein by removing the promoter from the source DNA by restriction enzyme digestion or amplifying the promoter by polymerase chain reaction and inserting the desired promoter sequence into the vector.

Suitable promoters for use with mammalian cells are well known and include, but are not limited to, those obtained from the genomes of eukaryotic viruses such as polyoma virus, fowlpox virus, adenovirus (such as Adenovirus 2), bovine papilloma virus, avian sarcoma virus, cytomegalovirus, retroviruses, hepatitis-B virus and most preferably Simian Virus 40 (SV40). Other suitable mammalian promoters include heterologous mammalian promoters, for example, heat-shock promoters and the actin promoter.

Particular promoters useful in the practice of the recombinant expression vectors of the invention include, but are not limited to: the SV40 early promoter region (Bernoist and Chambon, 1981, *Nature* 290: 304-10); the CMV promoter; the promoter contained in the 3' long terminal repeat of Rous sarcoma virus (Yamamoto, et al., 1980, *Cell* 22: 787-97); the herpes thymidine kinase promoter (Wagner et al., 1981, *Proc. Natl. Acad. Sci. U.S.A.* 78: 1444-45); and the regulatory sequences of the metallothionine gene (Brinster et al., 1982, *Nature* 296: 39-42). Also of interest are the following animal transcriptional control regions, which exhibit tissue specificity and have been utilized in transgenic animals: the elastase I gene control region that is active in pancreatic acinar cells (Swift et al., 1984, *Cell* 38: 639-46; Ornitz et al., 1986, *Cold Spring Harbor Symp. Quant. Biol.* 50: 399-409; MacDonald, 1987, *Hepatology* 7: 425-515); the insulin gene control region that is active in pancreatic beta cells (Hanahan, 1985, *Nature* 315: 115-22); the mouse mammary tumor virus control region that is active in testicular, breast, lymphoid and mast cells (Leder et al., 1986, *Cell* 45: 485-95); the beta-globin gene control region that is active in myeloid cells (Mogram et al., 1985, *Nature* 315: 338-40; Kollias et al., 1986, *Cell* 46: 89-94); the myelin basic protein gene control region that is active in oligodendrocyte cells in the brain (Readhead et al., 1987, *Cell* 48: 703-12); the myosin light chain-2 gene control region that is active in skeletal muscle (Sani, 1985, *Nature* 314: 283-86); the gonadotropic releasing hormone gene control region that is active in the hypothalamus (Mason et al., 1986, *Science* 234: 1372-78); and most particularly the immunoglobulin gene control region that is active in lymphoid cells (Grosschedl et al., 1984, *Cell* 38: 647-58; Adames et al., 1985, *Nature* 318: 533-38; Alexander et al., 1987, *Mol. Cell Biol.* 7: 1436-44).

Preferably, the promoter of a recombinant nucleic acid construct of the invention is active in the tissue from which a target or host cell is derived. For example, if the cell is a liver cell, one could advantageously use the albumin gene control region (Pinkert et al., 1987, *Genes and Devel.* 1: 268-76); the alpha-feto-protein gene control region (Krumlauf et al., 1985, *Mol. Cell Biol.* 5: 1639-48; Hammer et al., 1987, *Science* 235: 53-58); or the alpha 1-antitrypsin gene control region (Kelsey et al., 1987, *Genes and Devel.* 1: 161-71), all of which are active in the liver.

The vectors of the invention can also contain an enhancer sequence that increases transcription in higher eukaryotic cells of nucleic acid encoding FoxM1B protein. Enhancers are cis-acting elements of DNA, are usually about 10-300 bp in length, and act on promoters to increase transcription. Enhancers are relatively orientation- and position-independent. They have been found within introns as well as within several kilobases both 5' and 3' to the transcription unit. Several enhancer sequences available from mammalian genes are known (e.g., enhancers from globin, elastase, albumin, alpha-feto-protein, insulin, transthyretin, and HNF-6 genes). An enhancer from a virus also can be used to increase expression of a gene. The SV40 enhancer, the cytomegalovirus early promoter enhancer, the polyoma enhancer, and adenovirus enhancers are exemplary enhancing elements for the activation of eukaryotic promoters. While an enhancer may be spliced into the vector at a position 5' or 3' to a nucleic acid molecule, it is typically located at a site 5' from the promoter.

An origin of replication is typically a part of prokaryotic expression vectors, particularly those that are commercially available, and the origin aids in replication and amplification of the vector in a host cell or a target cell. If the vector of choice does not contain an origin of replication site, one may be chemically synthesized based on a known sequence, and ligated into the vector. For example, the origin of replication from the plasmid pBR322 (New England Biolabs, Beverly, Mass.) is suitable for most gram-negative bacteria, and various replication origins (e.g., from viruses of eukaryotes such as SV40, polyoma, adenovirus, vesicular stomatitus virus (VSV), or papillomaviruses such as HPV or BPV) are useful for cloning vectors in mammalian cells. Generally, a mammalian origin of replication is not needed for mammalian expression vectors (for example, the SV40 origin is often used only because it also contains the early promoter).

Expression vectors of the invention may be constructed from a convenient starting vector such as a commercially available vector. Such vectors may or may not contain all of the desired flanking sequences. Where one or more of the flanking sequences described herein are not already present in the vector, they may be individually obtained and ligated into the vector. Methods used for obtaining each of the flanking sequences are well known to one skilled in the art.

After the vector has been constructed and a nucleic acid molecule encoding FoxM1B protein has been inserted into the proper site of the vector, the completed vector may be inserted into a suitable host cell or a target cell for amplification and/or polypeptide expression. The transformation of an expression vector encoding FoxM1B protein into a selected host cell or target cell may be accomplished by well-known methods including methods such as transfection, infection, calcium chloride, electroporation, microinjection, lipofection, DEAE-dextran method, or other known techniques as described above. The method selected will in part be a function of the type of host cell or target cell to be used. These methods and other suitable methods are well known to the skilled artisan, and are set forth, for example, in Sambrook et al., 2001, MOLECULAR CLONING: A LABORATORY MANUAL, 3d ed., Cold Spring Harbor Laboratory Press, Cold Spring Harbor, N.Y.

A host cell or target cell, when cultured under appropriate conditions, synthesizes a FoxM1B protein that can subsequently be collected from the culture medium (if the host cell or target cell secretes it into the medium) or directly from the host cell or target cell producing it (if it is not secreted) if collection of the protein is desired. Selection of an appropriate host cell will depend upon a number of different factors, such as desired expression levels, polypeptide modifications that are desirable or necessary for activity (such as glycosylation or phosphorylation) and ease of folding into a biologically-active molecule.

Mammalian cell lines available as hosts for expression are well known in the art and include, but are not limited to, many immortalized cell lines available from the American Type Culture Collection (ATCC), such as Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected through determining which cell lines have high expression levels of FoxM1B protein.

Selection of an appropriate target cell will also depend on the various factors discussed above for selection of an appropriate host cell. In addition, a target cell can be selected based on the disease or condition that affects a patient who is to be treated by methods of the invention. For example, if a patient has a lung injury, a lung cell can be chosen as the appropriate target cell. A target cell can be, for example, a cell from or in the patient himself or a cell from a genetically suitable donor. A "genetically suitable donor" is a donor whose tissues present a low likelihood of being rejected by the recipient once introduced or transplanted.

Alternatively, expression of FoxM1B polypeptide in a cell can be decreased, by decreasing or inhibiting expression of a gene or genes (e.g., transcription factors) and/or increasing the expression of a gene or genes (e.g., transcriptional repressors) in a manner which results in decreased FoxM1B polypeptide production from the cell's endogenous FoxM1B gene. This method includes introducing a non-naturally occurring polypeptide (e.g., a polypeptide comprising a site-specific DNA binding domain fused to a transcriptional factor domain) into the cell such that decreased FoxM1B polypeptide production from the cell's endogenous FoxM1B gene results.

The present invention further relates to DNA constructs useful in the method of altering expression of a target gene. In certain embodiments, the exemplary DNA constructs comprise: (a) one or more targeting sequences, (b) a regulatory sequence, (c) an exon, and (d) an unpaired splice-donor site. The targeting sequence in the DNA construct directs the integration of elements (a)-(d) into a target gene in a cell such that the elements (b)-(d) are operatively linked to sequences of the endogenous target gene. In another embodiment, the DNA constructs comprise: (a) one or more targeting sequences, (b) a regulatory sequence, (c) an exon, (d) a splice-donor site, (e) an intron, and (f) a splice-acceptor site, wherein the targeting sequence directs the integration of elements (a)-(f) such that the elements of (b)-(f) are operatively linked to the endogenous gene. The targeting sequence is homologous to the preselected site in the cellular chromosomal DNA with which homologous recombination is to occur. In the construct, the exon is generally 3' of the regulatory sequence and the splice-donor site is 3' of the exon.

If the sequence of a particular gene is known, such as the nucleic acid sequence of FoxM1B polypeptide presented herein, a DNA fragment that is complementary to a selected region of the gene can be synthesized or otherwise obtained, such as by appropriate restriction of the native DNA at specific recognition sites bounding the region of interest. This fragment serves as a targeting sequence upon insertion into the cell and will hybridize to its homologous region within the genome. If this hybridization occurs during DNA replication, this DNA fragment, and any additional sequence attached thereto, will be incorporated into the newly synthesized daughter strand of DNA. The present invention, therefore, includes nucleotides encoding a FoxM1B polypeptide, which nucleotides may be used as targeting sequences.

As demonstrated herein, FoxM1B-dependent transcription requires binding of the Cdk1-Cyclin B complex through an LXLXXL (SEQ ID NO: 3) motif in the FoxM1B transcriptional activation domain. The data provided in the Examples below show that FoxM1B protein recruits Cdk1-Cyclin B or Cdk2-Cyclin E to efficiently phosphorylate the FoxM1B protein at Thr residue 596. Adjacent to the LXLXXL (SEQ ID NO: 3) motif is a Cdk phosphorylation site at Thr 596, whose retention is essential for FoxM1B-dependent transcription by mediating recruitment of p300/CBP coactivator proteins, which provides accessibility of the local chromatin structure through acetylation of histone proteins. Consistent with these findings, stimulation of Cdk1 activity together with increased CBP coactivator levels provided a 6.2-fold increase in FoxM1B-dependent transcription, whereas inhibiting Cdk1 function significantly diminished FoxM1B transcriptional activity. The results described herein suggest a positive feedback loop in which Cdk1 phosphorylation stimulates FoxM1B-mediated Cdc25B transcription and Cdc25B phosphatase further potentiates Cdk1 activity. Also, the Examples below demonstrate that inhibition of the Ras/MAPK and PI3K/PDK1 pathways separately or together results in significant decreases in FoxM1B-dependent transcriptional activity, indicating that these cascades are essential for FoxM1B transcriptional activity.

In one embodiment, the invention provides methods for inhibiting proliferation of a tumor cell comprising the step of inhibiting FoxM1B activity in the tumor cell. Several methods of inhibiting FoxM1B activity can be used to accomplish the methods of the invention. For example, FoxM1B activity in a cell can be inhibited by causing FoxM1B protein to localize in the cytoplasm, rather than in the nucleus. Causing FoxM1B to localize in the cytoplasm can be accomplished, for example, by contacting a cell with a compound that causes FoxM1B to translocate from the nucleus to the cytoplasm, or that sequesters FoxM1B in the cytoplasm and prevents FoxM1B from translocating from the cytoplasm to the nucleus. Such compounds can be identified using screening methods of the invention as described herein.

In addition, FoxM1B localization can be controlled by interfering with the ability of FoxM1B to interact with cellular proteins that may be necessary for nuclear localization of FoxM1B. FoxM1B localization can also be altered by interfering with compounds or proteins that are induce nuclear localization of FoxM1B. For example, growth hormone can cause expression and nuclear localization of FoxM1B in a cell (see, for example, co-owned and co-pending U.S. patent application Ser. No. 10/151,587, filed May 17, 2002 and explicitly incorporated by reference herein). Thus, in a tumor cell where growth hormone is causing FoxM1B expression and nuclear localization, tumor cell proliferation could be inhibited by contacting the cell with a growth hormone inhibitor.

In another embodiment, an inhibitor of FoxM1B activity used in the methods of the invention can decrease FoxM1B activity by interfering with cellular proteins necessary for FoxM1B activity. For example, an inhibitor can interfere with FoxM1B binding to Cdk1 or p300/CBP or can disrupt protein activity or interactions in the Ras/MAPK or PI3K/PDK1 pathways. In another embodiment, FoxM1B activity can be inhibited by contacting a tumor cell with a tyrphostin, for example, a Jak2 kinase inhibitor, such as AG490, which interferes with the pathway through which growth hormone activates FoxM1B.

In another aspect, FoxM1B activity can be inhibited by contacting a tumor cell with an antisense construct, wherein the antisense oligonucleotide is complementary to nucleic acid sequences of RNA or double-stranded DNA that encodes FoxM1B and that inhibits FoxM1B gene expression. Antisense oligonucleotides of the invention can be complementary to and hybridize with expression control sequences (such as triple helix formation) or to FoxM1B mRNA. For example, antisense DNA or RNA molecules, which have a sequence that is complementary to at least a portion of a FoxM1B gene can be introduced into a cell to interfere with expression of FoxM1B gene. Antisense oligonucleotides can be designed by available techniques using the sequence of the FoxM1B gene disclosed herein. Typically, an antisense molecule will be complementary to the start site (5' end) of the FoxM1B gene. When the antisense molecule then hybridizes to the corresponding FoxM1B mRNA, translation of this mRNA is prevented or reduced.

Alternatively, gene therapy can be employed to create a dominant-negative inhibitor of FoxM1B. In these embodiments, DNA encoding a mutant polypeptide of FoxM1B or FoxM1B activity inhibiting peptide fragment thereof can be prepared and introduced into the cells of a patient using either viral or non-viral methods as described herein. Each such mutant is typically designed to compete with endogenous FoxM1B in its biological role.

In one embodiment of the invention, an effective inhibitor of FoxM1B activity causes at least about 50% reduction in FoxM1B activity. Preferably, an effective inhibitor of FoxM1B activity causes at least about 80% reduction in FoxM1B activity. Most preferably, an inhibitor of FoxM1B activity causes at least about 90% reduction in FoxM1B activity.

In another embodiment, the invention provides screening methods for identifying compounds that can prevent tumor progression and inhibit tumor cell proliferation. The screening methods of the invention comprise identifying compounds that can inhibit FoxM1B activity or FoxM1B nuclear localization. For example, one embodiment of the screening methods of the invention comprises the steps of: contacting with a candidate compound a plurality of cells comprising a FoxM1B gene, wherein the cells express FoxM1B protein when cultured in vitro; assaying FoxM1B localization in the cells; and identifying a candidate compound when FoxM1B is localized in the cytoplasm and not in the nuclei of cells contacted with the compound but localized in the nuclei of cells not contacted with the compound.

Another embodiment of the screening methods of the invention comprises the steps of: contacting with a candidate compound a plurality of cells comprising a FoxM1B gene, wherein the cells express FoxM1B protein when cultured in vitro; assaying FoxM1B localization in the cells; selecting a candidate compound when FoxM1B is localized in the cytoplasm and not in the nuclei of cells contacted with the compound but localized in the nuclei of cells not contacted with the compound; and identifying a compound as a compound that can inhibit tumor progression if proliferation of tumor cells is inhibited when contacted with the compound in vitro or in vivo.

In yet another embodiment, the screening methods of the invention can comprise a pre-selection step, wherein a compound can be pre-selected for a screening method of the invention by contacting a plurality of cells with a candidate compound and assaying for cell proliferation, wherein a candidate compound is selected for a screening method of the invention if cell proliferation is inhibited (i.e. the cells proliferate more slowly or not at all in the presence than in the absence of the compound).

Still other embodiments of the screening methods of the invention comprise the steps of: contacting a cell with a compound, wherein the cell expresses a green fluorescent protein-FoxM1B (GFP-FoxM1B) fusion protein; contacting the cell with growth hormone; detecting localization of the GFP-FoxM1B protein in the cells; and identifying a compound as a compound that inhibits FoxM1B localization if the GFP FoxM1B protein is localized in the cytoplasm and not the nuclei of the cells.

Yet another embodiment of the screening methods of the invention comprises the steps of: contacting a transgenic mouse with a compound, wherein the cells of the transgenic mouse express a green fluorescent protein-FoxM1B (GFP-FoxM1B) fusion protein; administering growth hormone to the mouse; detecting localization of the GFP-FoxM1B protein in a cell removed from the mouse; and identifying a compound as a compound that inhibits FoxM1B nuclear localization if the GFP-FoxM1B protein is localized in the cytoplasm but not the nucleus of the cell that is removed from the mouse.

Assaying for nuclear localization and expression of FoxM1B protein can be accomplished by any method known the art. For example, immunohistochemistry using detectably-labeled primary anti-FoxM1B antibodies, or unlabeled primary anti-FoxM1B and detectably-labeled secondary antibodies (for example, labeled with fluorescent markers, such as fluorescein isothiocyanate, FITC), can be used to visualize FoxM1B protein localization, inter alia, by fluorescence microscopy. Alternative labels, such as radioactive, enzymatic and hapten labels, are within the scope of this invention.

As used herein, the terms "label" or "labeled" refers to incorporation of a detectable marker, e.g., by incorporation of a radiolabeled amino acid or attachment to a polypeptide of biotin moieties that can be detected by marked avidin (e.g., streptavidin containing a fluorescent marker or enzymatic activity that can be detected by optical or colorimetric methods). In certain embodiments, the label or marker can also be therapeutic. Various methods of labeling polypeptides and glycoproteins can be used that are known in the art. Examples of labels for polypeptides include, but are not limited to, the following: radioisotopes or radionuclides e.g., $^{3}H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent groups, biotin, and predetermined polypeptide epitopes recognized by a secondary reporter (e.g., leucine zipper pair sequences, binding sites for secondary antibodies, metal binding domains, epitope tags). In certain embodiments, labels are attached by spacer arms of various lengths (such as —($CH_2$)—, n=1-50, more preferably 1-20) to reduce steric hindrance.

Compounds identified in these screens can be used in the methods of inhibiting tumor cell proliferation, as discussed herein below.

The screening methods of the invention can also be used to identify endogenous FoxM1B inhibitor polypeptides by contacting cells with known polypeptides instead of test compounds. Such polypeptides can be used to inhibit FoxM1B activity as described herein.

In certain embodiments, the invention provides a method of inhibiting tumor growth in an animal comprising administering to the animal, which has at least one tumor cell present in its body, a therapeutically effective amount of an antisense oligonucleotide, for a therapeutically effective period of time, wherein the antisense oligonucleotide is complementary to nucleic acid sequences of RNA or double-stranded DNA that encodes FoxM1B and which inhibits FoxM1B gene expression. In another embodiment, the invention provides a method of inhibiting tumor growth in an animal comprising inhibiting FoxM1B activity in a tumor cell in the animal, for example, by administering to the animal, which has at least one tumor cell present in its body, a therapeutically effective amount of a compound that inhibits FoxM1B activity. Such compounds can be identified using screening methods of the invention as described herein.

In certain embodiments, the invention provides pharmaceutical compositions comprising a therapeutically effective amount of a compound that inhibits FoxM1B expression, nuclear localization or expression and or nuclear localization in mammalian cells together with a pharmaceutically acceptable diluent, carrier, solubilizer, emulsifier, preservative and/or adjuvant. In other embodiments, the invention provides pharmaceutical compositions that comprise a therapeutically effective amount of a compound that inhibits FoxM1B expression in mammalian cells and also induces FoxM1B protein to translocate into the cytoplasm from the nucleus of tumor cells together with a pharmaceutically acceptable diluent, carrier, solubilizer, emulsifier, preservative and/or adjuvant. Such compounds can be identified in screening methods of the invention. The invention further provides pharmaceutical compositions comprising a peptide having an amino acid sequence as set forth in SEQ ID NO: 10, SEQ ID NO: 11, or SEQ ID NO: 12.

The term "agent" is used herein to denote a chemical compound, a mixture of chemical compounds, a biological macromolecule, or an extract made from biological materials.

The term "pharmaceutical composition" as used herein refers to a composition comprising a pharmaceutically acceptable carrier, excipient, or diluent and a chemical compound, peptide, or composition as described herein that is capable of inducing a desired therapeutic effect when properly administered to a patient.

The term "therapeutically effective amount" refers to the amount of growth hormone or a pharmaceutical composition of the invention or a compound identified in a screening method of the invention determined to produce a therapeutic response in a mammal. Such therapeutically effective amounts are readily ascertained by one of ordinary skill in the art and using methods as described herein.

As used herein, "substantially pure" means an object species that is the predominant species present (i.e., on a molar basis it is more abundant than any other individual species in the composition). In certain embodiments, a substantially purified fraction is a composition wherein the object species comprises at least about 50 percent (on a molar basis or on a weight or number basis) of all macromolecular species present. In certain embodiments, a substantially pure composition will comprise more than about 80%, 85%, 90%, 95%, or 99% of all macromolar species present in the composition. In certain embodiments, the object species is purified to essential homogeneity (wherein contaminating species cannot be detected in the composition by conventional detection methods) wherein the composition consists essentially of a single macromolecular species.

The term "patient" includes human and animal subjects.

As used herein, the terms "tumor growth" and "tumor cell proliferation" are used to refer to the growth of a tumor cell. The term "tumor cell" as used herein refers to a cell that is neoplastic. A tumor cell can be benign, i.e. one that does not form metastases and does not invade and destroy adjacent normal tissue, or malignant, i.e. one that invades surrounding tissues, is capable of producing metastases, may recur after attempted removal, and is likely to cause death of the host. Preferably a tumor cell that is subjected to a method of the invention is an epithelial-derived tumor cell, such as a tumor cell derived from skin cells, lung cells, intestinal epithelial cells, colon epithelial cells, testes cells, breast cells, prostate cells, brain cells, bone marrow cells, blood lymphocytes, ovary cells or thymus cells.

Acceptable formulation materials preferably are nontoxic to recipients at the dosages and concentrations employed. The pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. Suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides, disaccharides, and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20 and polysorbate 80, Triton, trimethamine, lecithin, cholesterol, or tyloxapal); stability enhancing agents (such as sucrose or sorbitol); tonicity enhancing agents (such as alkali metal halides, preferably sodium or potassium chloride, mannitol, or sorbitol); delivery vehicles; diluents; excipients and/or pharmaceutical adjuvants. See, for example, REMINGTON'S PHARMACEUTICAL SCIENCES, 18$^{th}$ Edition, (A. R. Gennaro, ed.), 1990, Mack Publishing Company.

Optimal pharmaceutical compositions can be determined by one skilled in the art depending upon, for example, the intended route of administration, delivery format and desired dosage. See, for example, REMINGTON'S PHARMACEUTICAL SCIENCES, Id. Such compositions may influence the physical state, stability, rate of in vivo release and rate of in vivo clearance of the antibodies of the invention.

The primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. Pharmaceutical compositions can comprise Tris buffer of about pH 7.0-8.5, or acetate buffer of about pH 4.0-5.5, which may further include sorbitol or a suitable substitute therefor. Pharmaceutical compositions of the invention may be prepared for storage by mixing the selected composition having the desired degree of purity with optional formulation agents (REMINGTON'S PHARMACEUTICAL SCIENCES, Id.) in the form of a lyophilized cake or an aqueous solution. Further, the FoxM1B-inhibiting product may be formulated as a lyophilizate using appropriate excipients such as sucrose.

Formulation components are present in concentrations that are acceptable to the site of administration. Buffers are advantageously used to maintain the composition at physiological pH or at a slightly lower pH, typically within a pH range of from about 5 to about 8.

The pharmaceutical compositions of the invention can be delivered parenterally. When parenteral administration is contemplated, the therapeutic compositions for use in this invention may be in the form of a pyrogen-free, parenterally acceptable aqueous solution comprising the desired compound identified in a screening method of the invention in a pharmaceutically acceptable vehicle. A particularly suitable vehicle for parenteral injection is sterile distilled water in which the compound identified in a screening method of the invention is formulated as a sterile, isotonic solution, appropriately preserved. Preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which may then be delivered via a depot injection. Formulation with hyaluronic acid has the effect of promoting sustained duration in the circulation. Implantable drug delivery devices may be used to introduce the desired molecule.

The compositions may be formulated for inhalation. In these embodiments, a compound identified in a screening method of the invention or a FoxM1B inhibitor disclosed herein is formulated as a dry powder for inhalation, or inhalation solutions may also be formulated with a propellant for aerosol delivery, such as by nebulization. Pulmonary administration is further described in PCT Application No. PCT/US94/001875, which describes pulmonary delivery of chemically modified proteins and is incorporated by reference.

The pharmaceutical compositions of the invention can be delivered through the digestive tract, such as orally. The preparation of such pharmaceutically acceptable compositions is within the skill of the art. A FoxM1B inhibitor disclosed herein or compounds of the invention that are administered in this fashion may be formulated with or without those carriers customarily used in the compounding of solid dosage forms such as tablets and capsules. A capsule may be designed to release the active portion of the formulation at the point in the gastrointestinal tract when bioavailability is maximized and pre-systemic degradation is minimized. Additional agents can be included to facilitate absorption of the FoxM1B inhibitor disclosed herein or compound identified in a screening method of the invention. Diluents, flavorings, low melting point waxes, vegetable oils, lubricants, suspending agents, tablet disintegrating agents, and binders may also be employed.

A pharmaceutical composition may involve an effective quantity of a FoxM1B inhibitor disclosed herein or a compound identified in a screening method of the invention in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions are evident to those skilled in the art, including formulations involving a FoxM1B inhibitor disclosed herein or compounds of the invention in sustained- or controlled-delivery formulations. Techniques for formulating a variety of other sustained- or controlled-delivery means, such as liposome carriers, bio-erodible microparticles or porous beads and depot injections, are also known to those skilled in the art. See, for example, PCT Application No. PCT/US93/00829, which describes the controlled release of porous polymeric microparticles for the delivery of pharmaceutical compositions. Sustained-release preparations may include semipermeable polymer matrices in the form of shaped articles, e.g. films, or microcapsules, polyesters, hydrogels, polylactides (U.S. Pat. No. 3,773,919 and EP 058,481), copolymers of L-glutamic acid and gamma ethyl-L-glutamate (Sidman et al., 1983, *Biopolymers* 22: 547-556), poly(2-hydroxyethyl-methacrylate) (Langer et al., 1981, *J. Biomed. Mater. Res.* 15: 167-277) and Langer, 1982, *Chem. Tech.* 12: 98-105), ethylene vinyl acetate (Langer et al., id.) or poly-D(−)-3-hydroxybutyric acid (EP 133,988). Sustained release compositions may also include liposomes, which can be prepared by any of several methods known in the art. See e.g., Eppstein et al., 1985, *Proc. Natl. Acad. Sci. USA* 82: 3688-3692; EP 036,676; EP 088,046 and EP 143, 949.

The pharmaceutical composition to be used for in vivo administration typically is sterile. In certain embodiments, this may be accomplished by filtration through sterile filtration membranes. In certain embodiments, where the composition is lyophilized, sterilization using this method may be conducted either prior to or following lyophilization and reconstitution. In certain embodiments, the composition for parenteral administration may be stored in lyophilized form or in a solution. In certain embodiments, parenteral compositions generally are placed into a container having a sterile access port, for example, an intravenous solution bag or vial having a stopper pierceable by a hypodermic injection needle.

Once the pharmaceutical composition of the invention has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The present invention is directed to kits for producing a single-dose administration unit. Kits according to the invention may each contain both a first container having a dried protein compound identified in a screening method of the invention and a second container having an aqueous formulation, including for example single and multi-chambered pre-filled syringes (e.g., liquid syringes, lyosyringes or needle-free syringes).

The effective amount of a pharmaceutical composition of the invention to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which the pharmaceutical composition is being used, the route of administration, and the size (body weight, body surface or organ size) and/or condition (the age and general health) of the patient. A clinician may titer the dosage and modify the route of administration to obtain the optimal therapeutic effect. Typical dosages range from about 0.1 µg/kg to up to about 100 mg/kg or more, depending on the factors mentioned above. In certain embodiments, the dosage may range from 0.1 µg/kg up to about 100 mg/kg; or 1 µg/kg up to about 100 mg/kg; or 5 µg/kg up to about 100 mg/kg.

The dosing frequency will depend upon the pharmacokinetic parameters of a FoxM1B inhibitor disclosed herein or compound identified in a screening method of the invention in the formulation. For example, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

Administration routes for the pharmaceutical compositions of the invention include orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. The pharmaceutical compositions may be administered by bolus injection or continuously by infusion, or by implantation device. The pharmaceutical composition also can be administered locally via implantation of a membrane, sponge or another appropriate material onto which the desired molecule has been absorbed or encapsulated. Where an implantation device is used, the device may be implanted into any suitable tissue or organ, and delivery of the desired molecule may be via diffusion, timed-release bolus, or continuous administration.

In certain embodiments, it may be desirable to use a FoxM1B inhibitor disclosed herein or pharmaceutical compositions of compounds identified in a screening method of the invention in an ex vivo manner. In such instances, cells, tissues or organs that have been removed from the patient are exposed to pharmaceutical compositions of the invention or a recombinant nucleic acid construct encoding a FoxM1B inhibitor disclosed herein after which the cells, tissues and/or organs are subsequently implanted back into the patient.

In certain embodiments, a FoxM1B inhibitor disclosed herein, a FoxM1B inhibitor encoding recombinant nucleic acid constructs or pharmaceutical compositions of compounds identified in a screening method of the invention can be delivered by implanting certain cells that have been genetically engineered, using methods such as those described herein, to express and secrete the polypeptide. Such cells may be animal or human cells, and may be autologous, heterologous, or xenogeneic, or may be immortalized. In order to decrease the chances of an immunological response, the cells may be encapsulated to avoid infiltration of surrounding tissues. Encapsulation materials are typically biocompatible, semi-permeable polymeric enclosures or membranes that allow the release of the protein product(s) but prevent the destruction of the cells by the patient's immune system or by other detrimental factors from the surrounding tissues.

Pharmaceutical compositions of the invention can be administered alone or in combination with other therapeutic agents, in particular, in combination with other cancer therapy agents. Such agents generally include radiation therapy or chemotherapy. Chemotherapy, for example, can involve treatment with one or more of the following agents: anthracyclines, taxol, tamoxifene, doxorubicin, 5-fluorouracil, and other drugs known to one skilled in the art.

Anti-FoxM1B polypeptide cell therapy, e.g., the implantation of cells producing polypeptides that inhibit FoxM1B activity, is also provided herein. This embodiment of the invention involves implanting cells capable of synthesizing and secreting a biologically active form of a polypeptide of a FoxM1B inhibitor. Such FoxM1B inhibitor polypeptide-producing cells can be cells that are natural producers of FoxM1B inhibitor polypeptides or may be recombinant cells whose ability to produce FoxM1B inhibitor polypeptides has been augmented by transformation with a gene encoding the desired polypeptide or with a gene augmenting the expression of the polypeptide. Such a modification may be accomplished by means of a vector suitable for delivering the gene as well as promoting its expression and secretion. In order to minimize potential immunological reaction in patients being administered an inhibitor polypeptide, as may occur with the administration of a polypeptide of a foreign species, it is preferred that natural cells producing FoxM1B inhibitor polypeptide be of human origin, most preferably autologous to the individual in whom they are implanted, and produce human FoxM1B inhibitor polypeptide. Likewise, it is preferred that the recombinant cells, most preferably cells autologous to the individual in whom they are implanted, that produce FoxM1B inhibitor polypeptide be transformed with an expression vector containing a gene encoding a human FoxM1B inhibitor polypeptide.

Implanted cells may be encapsulated to avoid infiltration of surrounding tissue. Human or non-human animal cells may be implanted in patients in biocompatible, semipermeable polymeric enclosures or membranes that permit release of FoxM1B inhibitor polypeptide, but that prevent destruction of the cells by the patient's immune system or by other detrimental factors from surrounding tissue. Alternatively, autologous cells, i.e., the patient's own cells, transformed to produce FoxM1B inhibitor polypeptides ex vivo, may be implanted directly into the patient without such encapsulation.

Techniques for the encapsulation of living cells are known in the art, and preparation of encapsulated cells and their implantation in patients may be routinely accomplished. For example, Baetge et al. (PCT Pub. No. WO 95/05452 and PCT/US94/09299) describe membrane capsules containing genetically engineered cells for effective delivery of biologically active molecules. The capsules are biocompatible and are easily retrievable. The capsules encapsulate cells transfected with recombinant DNA molecules comprising DNA sequences encoding biologically active molecules operatively linked to promoters that are not subject to down-regulation in vivo upon implantation into a mammalian host. Such devices provide for the delivery of the molecules from living cells to specific sites within a recipient. See U.S. Pat. Nos. 4,892,538; 5,011,472; and 5,106,627. A system for encapsulating living cells is described in PCT Pub. No. WO 91/10425 (Aebischer et al.). See also, PCT Pub. No. WO 91/10470 (Aebischer et al.); Winn et al., 1991, *Exper. Neurol.* 113:322-29; Aebischer et al., 1991, *Exper. Neurol.* 111:269-75; and Tresco et al., 1992, *ASAIO* 38:17-23 for art-recognized systems for encapsulating living cells.

In vivo, ex vivo and in vitro gene delivery of FoxM1B inhibitor polypeptides or antisense oligonucleotides is also provided herein. One example of a gene therapy technique is to use an antisense oligonucleotide of the FoxM1B gene (either genomic DNA, cDNA, and/or mRNA) that is complementary to a portion of the gene encoding a FoxM1B polypeptide that can be operatively linked to a constitutive or inducible promoter to form a "gene therapy DNA construct." The promoter may be homologous or heterologous to the endogenous FoxM1B gene, provided that it is active in the cell or tissue type into which the construct is inserted. Other components of the gene therapy DNA construct may optionally include DNA molecules designed for site-specific integration (e.g., endogenous sequences useful for homologous recombination), tissue-specific promoters, enhancers or silencers, DNA molecules capable of providing a selective advantage over the parent cell, DNA molecules useful as labels to identify transformed cells, negative selection systems, cell specific binding agents (for example, for cell targeting), cell-specific internalization factors, transcription factors enhancing expression from a vector, and factors enabling vector production.

A gene therapy DNA construct can then be introduced into cells (either ex vivo or in vivo) using viral or non-viral vectors. One means for introducing the gene therapy DNA construct is by means of viral vectors as described herein. Certain vectors, such as retroviral vectors, will deliver the DNA construct to the chromosomal DNA of the cells, and the gene can integrate into the chromosomal DNA. Other vectors will function as episomes, and the gene therapy DNA construct will remain unintegrated, for example, in the cell cytoplasm. Other suitable methods for delivering nucleic acid constructs into cells are disclosed in U.S. Pat. No. 6,475,798 filed Nov. 5, 2002; U.S. Pat. No. 6,291,243 filed Sep. 18, 2001; and US Patent Application Number 20030033615 filed Feb. 13, 2003, all of which are hereby incorporated by reference.

In yet other embodiments, regulatory elements can be included for controlled expression of the antisense oligonucleotide or a FoxM1B inhibitor polypeptide in the target cell. Such elements are activated in response to an appropriate effector. In this way, a therapeutic polypeptide can be expressed when desired. One conventional control means involves the use of small molecule dimerizers or rapalogs to dimerize chimeric proteins which contain a small molecule-binding domain and a domain capable of initiating a biological process, such as a DNA-binding protein or transcriptional activation protein (see PCT Pub. Nos. WO 96/41865, WO 97/31898, and WO 97/31899). The dimerization of the proteins can be used to initiate transcription of the transgene.

In vivo gene therapy may be accomplished by introducing the gene encoding FoxM1B inhibitor polypeptide or an antisense oligonucleotide into cells via local delivery of a FoxM1B nucleic acid molecule, by direct injection or by other appropriate viral or non-viral delivery vectors. (Hefti, 1994, *Neurobiology* 25:1418-35.) For example, a nucleic acid molecule encoding a FoxM1B polypeptide may be contained in an adeno-associated virus (AAV) vector for delivery to the targeted cells (see, e.g., Johnson, PCT Pub. No. WO 95/34670; PCT App. No. PCT/US95/07178). The recombinant AAV genome used according to the teachings of the invention typically contains AAV inverted terminal repeats flanking a DNA sequence encoding a FoxM1B polypeptide operatively linked to functional promoter and polyadenylation sequences.

Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors. U.S. Pat. No. 5,672,344 describes an in vivo viral-mediated gene transfer system involving a recombinant neurotrophic HSV-1 vector. U.S. Pat. No. 5,399,346 provides examples of a process for providing a patient with a therapeutic protein by the delivery of human cells that have been treated in vitro to insert a DNA segment encoding a therapeutic protein. Additional methods and materials for the practice of gene therapy techniques are described in U.S. Pat. No. 5,631,236 (involving adenoviral vectors), U.S. Pat. No. 5,672,510 (involving retroviral vectors), and U.S. Pat. No. 5,635,399 (involving retroviral vectors expressing cytokines).

Nonviral delivery methods include, but are not limited to, liposome-mediated transfer, naked DNA delivery (e.g., by direct injection), receptor-mediated transfer (ligand-DNA complex), electroporation, calcium phosphate precipitation, and microparticle bombardment (e.g., gene gun). Gene therapy materials and methods may also include inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture. Such additional methods and materials for the practice of gene therapy techniques are described in U.S. Pat. No. 4,970,154 (involving electroporation techniques), U.S. Pat. No. 5,679,559 (describing a lipoprotein-containing system for gene delivery), U.S. Pat. No. 5,676,954 (involving liposome carriers), U.S. Pat. No. 5,593,875 (describing methods for calcium phosphate transfection), and U.S. Pat. No. 4,945,050 (describing a process wherein biologically active particles are propelled at cells at a speed whereby the particles penetrate the surface of the cells and become incorporated into the interior of the cells), and PCT Pub. No. WO 96/40958 (involving nuclear ligands).

It is also contemplated that FoxM1B gene therapy or cell therapy can further include the delivery of one or more additional polypeptide(s) in the same or a different cell(s). Such cells may be separately introduced into the patient, or the cells may be contained in a single implantable device, such as the encapsulating membrane described above, or the cells may be separately modified by means of viral vectors.

Another means of increasing endogenous FoxM1B inhibitor polypeptide expression in a cell via gene therapy is to insert one or more enhancer elements into the FoxM1B inhibitor polypeptide promoter, where the enhancer elements can serve to increase transcriptional activity of the FoxM1B inhibitor gene. The enhancer elements used are selected based on the tissue in which one desires to activate the gene-enhancer elements known to confer promoter activation in that tissue are preferred. For example, if a gene encoding a FoxM1B inhibitor polypeptide is to be "turned on" in T-cells, the lck promoter enhancer element may be used. Here, the functional portion of the transcriptional element to be added may be inserted into a fragment of DNA containing the FoxM1B inhibitor polypeptide promoter (and optionally, inserted into a vector and/or 5' and/or 3' flanking sequences) using standard cloning techniques. This construct, known as a "homologous recombination construct," can then be introduced into the desired cells either ex vivo or in vivo.

The following Examples are provided for the purposes of illustration and are not intended to limit the scope of the present invention. The present invention is not to be limited in scope by the exemplified embodiments, which are intended as illustrations of individual aspects of the invention. Indeed, various modifications of the invention in addition to those shown and described herein will become apparent to those skilled in the art from the foregoing description and accompanying drawings. Such modifications are intended to fall within the scope of the appended claims.

EXAMPLES

Example 1

Generation of Conditional FoxM1B Knockout Mice

Figure 2:
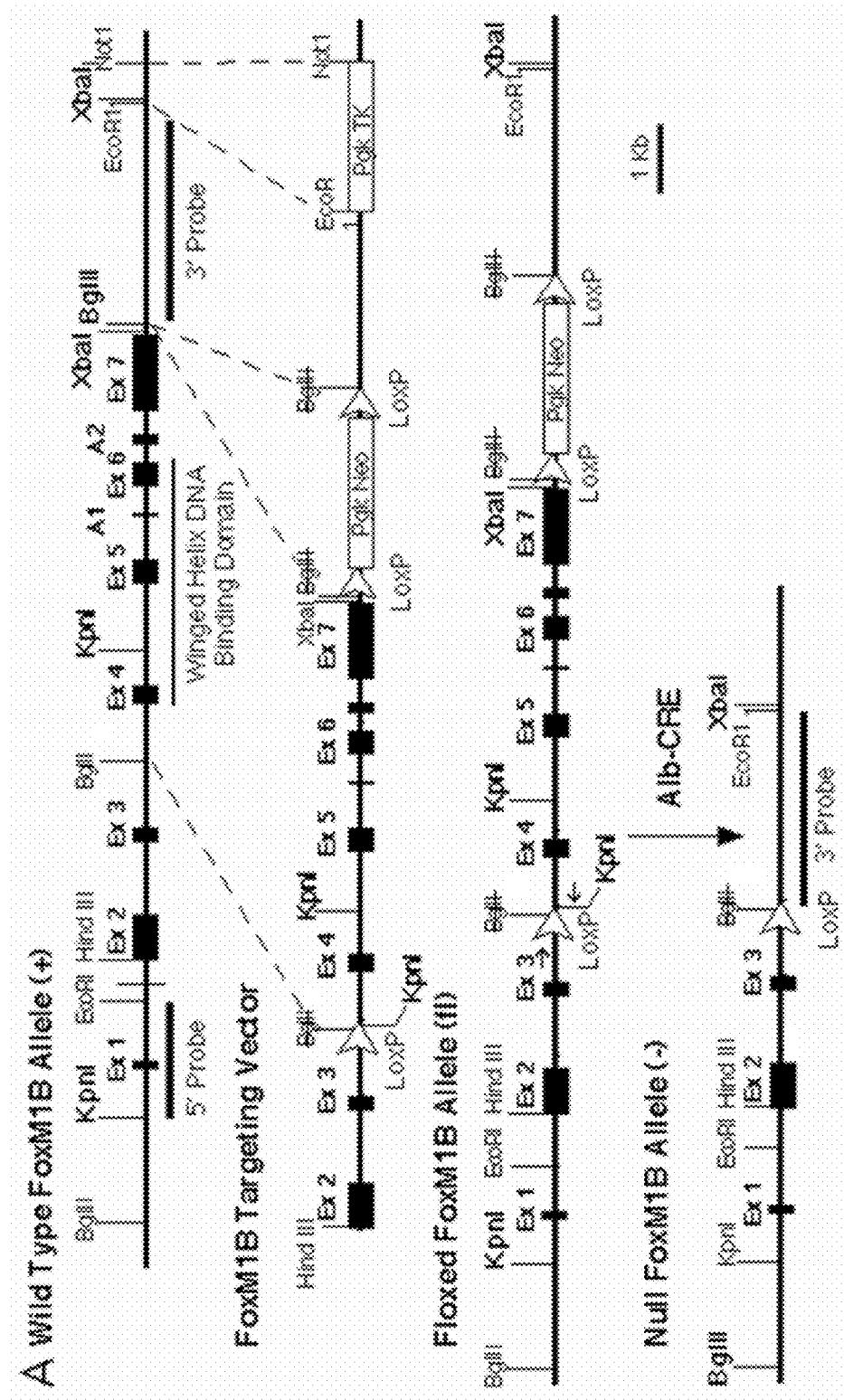
FIG. 2 is a schematic representation of triple-LoxP FoxM1B targeting vector used to generate conditional FoxM1B knockout mice.

FoxM1B knockout mice die immediately after birth. Therefore, to examine the role of FoxM1B in adult tissues, conditional FoxM1B knockout mice were generated using a triple-LoxP FoxM1B targeting vector to create a "Floxed" FoxM1B targeted locus (see FIG. 2 for a schematic diagram of the vector). Cre recombinase-mediated deletion of the FoxM1 genomic sequences spanning the two LoxP sites removes the entire winged helix DNA binding domain and the C-terminal transcriptional activation domain, thereby preventing expression of functional FoxM1 isoforms. Following standard electroporation and culture of mouse embryonic stem (ES) cells to select for homologous recombination (G418 and gangcyclovir), homologous recombinants were identified by Southern blotting of ES cell genomic DNA.

Mouse blastocysts were injected with the ES cells comprising the "Floxed" (fl/+) FoxM1B targeted allele, and chimeric mice with germ line transmission were selected. Viable mice homozygous for the "Floxed" (fl/fl) FoxM1B targeted allele were generated in this manner. Mice either homozygous (fl/fl) or heterozygous (fl/+) for the FoxM1B (fl) allele were verified by PCR amplification of mouse genomic DNA with primers that flanked the LoxP site. Breeding the albumin promoter Cre recombinase transgene into the FoxM1B (fl/fl) mouse genetic background allowed hepatocyte deletion of the FoxM1B locus within six weeks after birth, which was verified by Southern blot using liver genomic DNA.

Example 2

TTR-FoxM1B Transgenic Livers Display Increased Size of Hepatic Preneoplastic and Neoplastic Nodules To investigate the influence of increased FoxM1B expression on liver tumor formation, wild type (WT) and TTR-FoxM1B transgenic (TG) CD-1 mice were treated for 23 weeks with diethylnitrosamine (DEN)/Phenobarbital (PB) liver tumor induction (Goldfarb et al., 1983, Environ. Health Perspect. 50:149-161; Russell et al., 1996, Mol. Carcinog. 15:183-189; Slagle et al., 1996, Mol. Carcinog. 15:261-269; Tamano et al., 1994, Carcinogenesis 15:1791-1798). Transgenic CD-1 mice were generated using the −3 kb transthyretin (TTR) promoter to constitutively express the FoxM1B transgene (SEQ ID NO: 1 as shown in FIG. 1) in hepatocytes as described (Ye et al., 1999, Mol. Cell Biol., 19: 8570-8580). At 14 days postnatal of age 17 WT and TTR-FoxM1B TG CD-1 mice received a single IP injection of 5 µg of DEN/g body weight (10 µl/g body weight of 0.05% solution of DEN in water). At 4 weeks of age, mice were placed on water containing 0.05% of PB for 21 weeks. The mice were sacrificed at 25 weeks of age, the livers were fixed in paraformaldehyde, paraffin embedded, sectioned and then H&E stained and examined for tumors. The TTR-FoxM1B TG livers exhibited larger preneoplastic and neoplastic nodules (Table 2; greater than 200 µm in size) and hepatocyte proliferation was stimulated in these hepatic nodules as determined by immunohistochemical staining for Ki67 antigen. However, increased FoxM1B levels did not increase the number of hepatic tumor nodules, suggesting that FoxM1B enhanced the growth of hepatic tumors but did not stimulate tumor initiation.

TABLE 2

| | Size of liver tumor | | |
|---|---|---|---|
| | $R \geq 450 \, \mu m^a$ | $450 \, \mu m > R \geq 200 \, \mu m^b$ | $R < 200 \, \mu m$ |
| TTR-FoxM1B TG liver | 3.6 ± 1.3 | 20.3 ± 6.1 | 5.7 ± 4.0 |
| Wild Type Liver | 0.3 ± 0.3 | 8.8 ± 2.5 | 38.8 ± 9.4 |

Table 2 shows the mean number±(s.e.m.) of hepatic preneoplastic or neoplastic nodules (adenomas) per $cm^3$ within the range of sizes shown (n=17 for each genotype). As shown in column 2(a) and 3(b), values are significantly different from control mice based on the Student's t-test P=0.019 and P=0.0027, respectively.

Example 3

Figure 3:
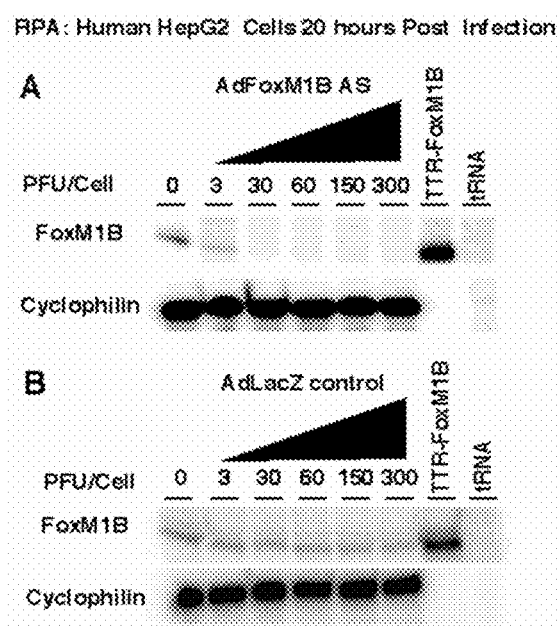
FIGS. 3A and 3B show RNase protection assays (RPA) with a FoxM1B probe after infection of human hepatoma HepG2 cells with Adenovirus expressing antisense human FoxM1B cDNA (AdFoxM1B AS).
Figure 4:
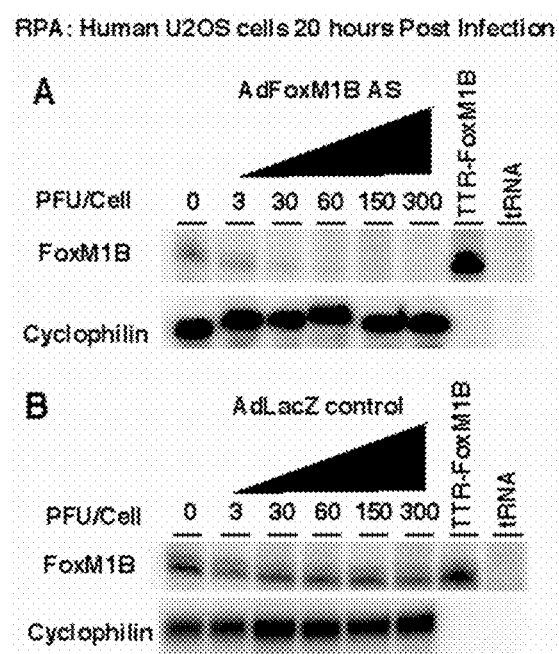

Infection of Proliferating Human Cell Lines with Adenovirus Expressing Antisense Human FoxM1B cDNA Inhibits Expression of Endogenous FoxM1B mRNA Proliferating human hepatoma HepG2 cells were infected with an increasing amounts of plaque forming units (PFU) per cell of either an adenovirus expressing antisense human FoxM1B cDNA (FIG. 3A, AdFoxM1B AS) or Adenovirus expressing bacterial LacZ gene (FIG. 3B, AdLacZ) and total RNA was isolated 20 hours following post infection. Expression of human FoxM1B mRNA was measured using an RNase protection assay (RPA) with a FoxM1B probe as described previously (Ye et al., 1999, Mol. Cell. Biol. 19:8570-8580; Ye et al., 1997, Mol. Cell Biol. 17:1626-1641). These RPA studies demonstrated that AdFoxM1B AS infection at 30 pfu per cell is sufficient to inhibit endogenous FoxM1B expression (FIG. 3A), but AdLacZ control infections did not influence FoxM1B expression (FIG. 3B). Furthermore, AdFoxM1B infection of human osteoblastoma U2OS cells was sufficient to prevent FoxM1B expression in this human tumor cell line as well (FIG. 4). Taken together infection of cells with AdFoxM1B AS is an effective means by which to inhibit FoxM1B expression in tumor cell lines.

Example 4

Generation of FoxM1B Expression Plasmids and Luciferase Reporter Plasmid

The CMV-FoxM1B expression plasmid was generated by PCR amplification of the CMV Human FoxM1B expression plasmid (Ye et al., 1997, *Mol. Cell Biol.* 17:1626-1641) with 5' EcoR1 T-epitope tagged FoxM1B primer: 5'-gcggaattcac-catggctagcatgactggtggacag-caaatgggtTGGCAGAACTCTGTGTCTGAG (SEQ ID NO: 4) and a 3' antisense primer that hybridized to the CMV expression vector SV-40 poly A region: 5'-gttttgtccaattatgtca (SEQ ID NO: 5). The resulting 3.3 KB FoxM1B PCR product was digested with EcoR1 and HindIII, generating the 2.5 KB EcoRI-HindIII T7 tagged FoxM1B cDNA fragment and removing 800 nucleotides from the 3' untranslated region. This FoxM1B cDNA fragment was subsequently cloned in the corresponding sites in the CMV expression vector (Pani et al., 1992, *Mol. Cell Biol.* 12:3723-373245).

A CMV pEGFP-FoxM1B expression plasmid was generated by liberating a 2.5 KB EcoRI-HindIII fragment from the CMV FoxM1B expression vector. The HindIII site was made blunt by T4 polymerase fill in reaction and then the FoxM1B cDNA fragment was cloned into EcoRI-SmaI sites of the pEGFP-C2 expression plasmid (Clontech). The CMV tetracycline operator (CMV-TO) FoxM1B expression plasmid was generated by excising an EcoRI-BamHI fragment from pEGFP-FoxM1B expression plasmid. The BamHI site was made blunt by a T4 polymerase reaction and then the FoxM1B cDNA fragment was cloned into EcoRI and EcoRV sites of the pCDNA4-TO expression plasmid (T-Rex system, Invitrogen).

A 6X FoxM1B/FoxA TATA-Luciferase utilized 6 copies of the FoxM1B/FoxA binding site (TTTGTTTGTTTG; SEQ ID NO: 6) from the cdx-2 promoter region driving expression of the CMV-TATA box luciferase reporter gene as described previously (Rausa et al., 2003, *Mol. Cell. Biol.* 23:437-449; Samadani et al., 1996, *Mol. Cell. Biol.* 16:6273-6284; Ye et al., 1997, *Mol. Cell Biol.* 17:1626-1641).

Example 5

FoxM1B-Dependent Transcription Requires the 596 Cdk Phosphorylation Site and Binding of Cdk1/Cdk2 Proteins through the FoxM1B LXLXXL Sequence Previous transfection studies demonstrated that the FoxM1B transcriptional activation domain was contained within the carboxyl-terminal 365 to 748 amino acid residues (Ye et. al., 1997. *Mol. Cell. Biol.* 17:1626-1641). Searching the FoxM1B C-terminal sequence for Cdk1/2 consensus phosphorylation sites X-pS/T-P-X-R/K revealed three potential Cdk1/2 sites at residues 585, 596 and 657 in the FoxM1B protein (FIG. 5A). In order to assess the transcriptional function of these potential FoxM1B Cdk1/2 sites, site-directed mutagenesis was used to alter either Thr or Ser residue to an Ala residue to prevent their Cdk phosphorylation in vivo. Transient transfection assays with 6X FoxM1B TATA-luciferase reporter and CMV vectors expressing either WT or Cdk1/2 mutant FoxM1B protein revealed that mutation of Cdk1/2 sites at either 585 or 657 resulted in only a marginal decrease (20% to 30%) in FoxM1B transcriptional activity (FIG. 5B). In contrast, mutation of the FoxM1B 596 Thr residue (FoxM1B T596A) caused an 80% decrease in transcriptional activity, suggesting that this particular Cdk1/2 phosphorylation site plays an important role in FoxM1B-dependent transcription (FIG. 5B). Moreover, FoxM1B was unable to activate expression of the TATA-luciferase control reporter in cotransfection assays, demonstrating that the multimerized FoxM1B binding sites were required for FoxM1B-dependent transcriptional activation (FIG. 5B).

To identify FoxM1B sequences involved in the interaction with Cdk proteins, site-directed mutagenesis was used to convert the Leu 641 residue to an Ala residue thereby disrupting the FoxM1B LXL (639-641) motif shown in FIG. 5A, which has been shown to bind to Cdk-Cyclin proteins as efficiently as the Cyclin-binding Cy (RXL) motif (Takeda et al., 2001, *J Biol Chem* 276:1993-1997; Wohlschlegel et al., 2001, *Mol Cell Biol* 21:4868-4874). Transient transfection assays demonstrated that FoxM1B L641A mutant protein displayed an 80% reduction in transcriptional activity (FIG. 5B). Furthermore, increasing amounts of the CMV FoxM1B L641A expression vector inhibited transcriptional activity of the WT FoxM1B protein in cotransfection assays, suggesting that the CMV FoxM1B L641A mutant protein functioned as a dominant negative inhibitor. Moreover, both GFP-T7-FoxM1B L641A and GFP-T7-FoxM1B T596A mutant proteins are retained in the nucleus (FIG. 4A-C), indicating that their diminished transcriptional activity was not due to inhibition of nuclear localization.

To determine whether the FoxM1B T596A or FoxM1B L641A mutant proteins exhibited diminished protein association with either the Cdk1 or Cdk2 protein, co-immunoprecipitation (Co-IP) experiments were performed with protein extracts prepared from U2OS cells transfected with either CMV T7-FoxM1B WT or mutant expression constructs (FIG. 5C). The transfected U2OS cell extracts were Co-IP with either Cdk1 or Cdk2 antibody and then FoxM1B protein was visualized by Western blot analysis with the T7 epitope Tag monoclonal antibody. These studies demonstrated that CMV T7-FoxM1B L641A mutant protein was unable to interact with either Cdk1 or Cdk2 proteins, whereas the FoxM1B mutant proteins disrupted in each of the Cdk1 phosphorylation sites could efficiently associate with the Cdk proteins (FIG. 5C). These results suggested that retention of the second Leu residue within the LXL sequence was essential for interaction between FoxM1B and Cdk proteins, and that FoxM1B binding of either Cdk1 or Cdk2 Cyclin protein complexes was required for its transcriptional activity.

To examine whether the Cdk1-Cyclin B complex phosphorylates the FoxM1B protein, Co-immunoprecipitation (Co-IP) Cdk1 in vitro kinase assays were performed with $^{32}$P labeled γ-ATP. Protein extracts prepared from U2OS cells transfected with either CMV GFP-T7-FoxM1B WT or GFP-T7-FoxM1B Cdk mutant expression vectors were co-immunoprecipitated with Cdk-1 antibody and were then used for radioactive Cdk1 in vitro kinase assay. The proteins phosphorylated in the Co-IP Cdk1 in vitro kinase reaction were resolved on SDS-PAGE and visualized by autoradiography. Consistent with reduced transcriptional activity, the Cdk1 Co-IP kinase assay demonstrated that GFP-T7-FoxM1B T596A mutation exhibited reduced phosphorylation by the Cdk1 protein, whereas Cdk1 phosphorylated the GFP-T7-FoxM1B T585A and GFP-T7-FoxM1B S657A proteins to levels found with the GFP-T7-FoxM1B WT protein (FIG. 5D). As expected, the GFP-T7-FoxM1B L641A mutant protein failed to interact efficiently with Cdk1 protein (FIG. 5C)

and therefore only low levels of FoxM1B L641A mutant protein were available for Cdk1 phosphorylation in the Co-IP Cdk1 kinase assay (FIG. 5D).

To examine Cdk phosphorylation in vivo, protein extracts were prepared from serum stimulated U2OS cells transfected with either CMV T7-FoxM1B WT, CMV T7-FoxM1B T596A or CMV FoxM1B L641A expression constructs. These protein extracts were IP with the T7 antibody and then Western blot analysis with the MPM2 monoclonal antibody was used to determine Cdk phosphorylation in vivo. These results demonstrated that Cdk phosphorylation of T7-FoxM1B WT protein was increased following serum stimulation and that the FoxM1B Thr 596 residue was required for phosphorylation by the Cdk-Cyclin complexes in vivo (FIG. 5E). Furthermore, in vivo Cdk phosphorylation of the T7-FoxM1B L641A mutant protein was significantly reduced (FIG. 5E), suggesting that recruitment of the Cdk-Cyclin complex by the FoxM1B LXL sequence was critical for its efficient Cdk phosphorylation in vivo.

Example 6

FoxM1B-Dependent Transcription is Stimulated by Increased Cdk1 activity and CBP Co-Activator Levels CMV-FoxM1B and the 6X FoxM1B TATA luciferase constructs were co-transfected with increasing amounts of CMV-DN-Cdk1 or cells were treated with increasing concentration of the pharmacological Cdk1 inhibitor Alsterpaullone (FIG. 6A) to demonstrate that Cdk1 activity is necessary for FoxM1B transcriptional activity. Inhibiting Cdk1 activity with either dominant negative (DN) Cdk1 or a pharmacologically active concentration of Alsterpaullone (1 µM) caused an 80% to 90% reduction in FoxM1B transcriptional activity (FIG. 6C). Neither DN-Cdk1 nor Alsterpaullone (1 µM) altered nuclear localization of transfected CMV GFP-FoxM1B protein (FIGS. 7A, B and E), suggesting that inhibiting Cdk1 activity alone diminished FoxM1B-dependent transcription. Furthermore, co-transfection of CMV WT-Myt1 kinase, which negatively regulates Cdk1 activity through phosphorylation, resulted in a 64% reduction in FoxM1B transcriptional activity (FIG. 6C). Consistent with these findings, stimulation of Cdk1 activity by co-transfection of either CMV Cdc25B or Cdc25C phosphatases enhanced FoxM1B transcriptional activity by 3.4-fold and 1.7-fold, respectfully (FIGS. 6B and 6D). Furthermore, co-transfection of CMV Cdc25B and CMV CBP together significantly augmented CBP-mediated stimulation of FoxM1B transcriptional activity from 1.4-fold to 6.2-fold increase (FIG. 6D). Taken together, these results provided evidence that Cdk1 activity was required to stimulate FoxM1B transcriptional activity.

Example 7

FoxM1B Transcriptional Activity Involves Recruitment of CBP through Phosphorylation of the FoxM1B 596 Cdk1 Site Co-transfection assays were performed with CMV-CBP or CMV-Adenovirus E1A alone or in combination to determine if FoxM1B transcriptional activity required the CBP co-activator protein. Co-transfection of CMV-CBP stimulated FoxM1B transcriptional activity by 50%, whereas inhibition of CBP function with E1A resulted in a 75% reduction in FoxM1B transcriptional activity (FIG. 8A). These studies suggested that recruitment of the p300/CBP family of coactivator proteins was essential for FoxM1B transcriptional activation.

U2OS cells were transiently transfected with CMV-CBP and either CMV GFP-FoxM1B, CMV GFP-FoxM1B comprising an L641A mutation, or CMV GFP-FoxM1B comprising an T596A mutation to determine if the critical FoxM1B 596 Cdk1 phosphorylation site was required for recruitment of CBP. Protein extracts were prepared 48 hours after transfection, and then used for immunoprecipitation with CBP antibody followed by Western blot analysis with GFP monoclonal antibody. These co-IP experiments demonstrated that both WT and FoxM1B L641A mutant proteins could efficiently interacted with the CBP protein (FIG. 8B). In contrast, disruption of the FoxM1B Cdk1 phosphorylation site at Thr residue 596 significantly diminished FoxM1B's ability to associate with the CBP protein (FIG. 8B). Taken together these results showed that FoxM1B phosphorylation by Cdk1-Cyclin B complex was required for recruitment of the p300/CBP coactivator protein, serving as a mechanism for proliferation-specific stimulation of FoxM1B transcriptional activity.

Example 8

Blocking the Ras-MAPK and PI3K-PDK1 Pathways Diminished FoxM1B Transcriptional Activity, but Inhibiting Akt did not Influence FoxM1B-Dependent Transcription The role of the MAPK and PI3K pathways in regulating FoxM1B activity was examined using FoxM1B transcription assays performed in U2OS cells that were either treated with the pharmacological MEK1/2 inhibitor U0126 or PI3K inhibitor Ly294002, or co-transfected with CMV DN-RasN17 expression vector (FIG. 9A). These transfection studies demonstrated that inhibition of MEK1/2, PI3K or Ras caused a 70 to 80% reduction in FoxM1B-dependent transcription (FIG. 9C), a finding consistent with the important roles of Ras/MAPK and PI3K/PDK1 pathways in Cdk1-Cyclin B activation. In contrast, blocking the Akt pathway with either CMV DN-Akt or the Akt pharmacological kinase inhibitor did not significantly alter FoxM1B transcriptional activity (FIG. 9C). Furthermore, combining the MEK1/2 (U0126) and PI3K (Ly294002) inhibitors resulted in a 90% reduction in FoxM1B-dependent transcription demonstrating the importance of the Ras/MAPK and PI3K/PDK1 pathway in regulating FoxM1B transcriptional activity (FIG. 9C). Co-transfection of CMV DN-p90Rsk (FIG. 9A) resulted in a 56% reduction in FoxM1B transcriptional activity (FIG. 9C), which was similar to the transcriptional reductions found with CMV WT-Myt1 (FIG. 6C). Addition of the Ras/MEK1/2 or PI3K/Akt pathway inhibitors did not diminish expression (FIG. 9B) or nuclear localization of GFP-FoxM1B protein (FIGS. 7C, D, G and H), suggesting that these inhibitors caused decreases in FoxM1B transcriptional activity. However, co-transfection of DN-p90Rsk resulted in redistribution of a portion of GFP-FoxM1B fluorescence to the periphery of the nucleus (FIG. 7F), suggesting that p90Rsk signaling may influence FoxM1B nuclear localization. Taken together, these studies demonstrated that FoxM1B transcriptional activity required Cdk1-Cyclin B1 activation, which was mediated by growth factor stimulation of the Ras/MAPK and PI3K/PDK1 signaling cascades.

Example 9

Alb-Cre Foxm1b −/− Livers Fail to Develop Hepatic Adenomas or Hepatocellular Carcinomas After DEN/PB Treatment A well-established Diethylnitrosamine (DEN)/Phenobarbital (PB) liver tumor induction protocol (see Tamano et al., 1994, *Carcinogenesis* 15:1791-1798; Sargent et al., 1996, *Cancer Res.* 56:2985-91; Kalinina et al., 2003, *Oncogene* 22:6266-6276) was used to determine whether Foxm1b was required for proliferative expansion during mouse liver tumor formation. A single intraperitoneal (IP) injection of the tumor initiator Diethylnitrosamine (DEN) was given at 14 days postnatally to the entire mouse litter containing both Foxm1b fl/fl (control) and Alb-Cre Foxm1b −/− (experimental) pups. Two weeks later, the mice were placed on drinking water containing 0.05% of the liver tumor promoter Phenobarbital (PB) for the duration of the liver tumor induction experiment.

Eight control Foxm1b fl/fl mice and 11 experimental Alb-Cre Foxm1b −/− mice were sacrificed at 23 weeks of DEN/PB exposure and seven control Foxm1b fl/fl and 13 experimental Alb-Cre Foxm1b −/− mice were sacrificed at 33 weeks following DEN/PB treatment (Table 3).

TABLE 3

Number of tumors per cm² liver tissue after 23 or 33 weeks of DEN/PB treatment

| DEN/PB & Sex | Foxm1b fl/fl Mice | | | | Alb-Cre Foxm1b −/− Mice | | | |
|---|---|---|---|---|---|---|---|---|
| | [1]# Mice | [2]Adenomas | # Mice | Carcinomas | # Mice | Adenomas | # Mice | Carcinomas |
| 23 weeks Male | 3 | 14.2 ± 5.2 | 3 | 0.5 ± 1.0 | 6 | 0 | 6 | 0 |
| 33 weeks Male | 3 | 11.2 ± 0.6 | 3 | 3.8 ± 0.9 | 7 | 0 | 7 | 0 |
| 23 weeks Female | 5 | 3.5 ± 1.7 | 5 | 0 | 5 | 0 | 5 | 0 |
| 33 weeks Female | 4 | 21.0 ± 6.9 | 4 | 0 | 6 | 0 | 6 | 0 |

[1]# Mice: Number of mice (male or female) analyzed for liver tumors after either 23 or 33 weeks of Diethylnitrosamine (DEN)/Phenobarbital (PB) treatment.
[2]Number of liver tumors per cm² liver tissue ± SD (adenomas or hepatocellular carcinomas greater than 0.1 mm in size) determined from Hematoxylin and Eosin stained liver sections obtained from four different mouse liver lobes.

Livers were harvested from male Foxm1b fl/fl and Alb-Cre Foxm1b −/− mice after 6 weeks of DEN/PB exposure to provide an early time point during liver tumor promotion. Liver sections were histologically stained with Hematoxylin and Eosin (H&E) and hepatocyte DNA replication was determined by immunofluorescent detection of BrdU that had been administered in drinking water 4 days before sacrificing the mice following the procedure described in Ledda-Columbano et al., 2002, *Hepatology* 36:1098-1105. After 23 weeks of DEN/PB treatment, H&E stained liver sections from Foxm1b fl/fl male mice revealed numerous hepatic adenomas with abundant BrdU labeling (Table 3). Highly proliferative hepatocellular carcinomas (HCC) with abundant BrdU labeling were visible in liver sections from each of the male control Foxm1b fl/fl mice following 33 weeks of DEN/PB exposure (Table 3). Furthermore, significant numbers of hyper-proliferative adenomas were found in liver sections from female and male Foxm1b fl/fl mice after 33 weeks of DEN/PB treatment (Table 3). No hepatic adenomas or HCC were detected in male or female Alb-Cre Foxm1b −/− mice at either 23 or 33 weeks following DEN/PB exposure (Table 3). At 6, 23 and 33 weeks following DEN/PB treatment, low levels of BrdU incorporation were found in Foxm1b deficient hepatocytes, which was approximately 30% of BrdU labeling levels found in Foxm1b fl/fl hepatocytes of non-tumor regions following DEN/PB exposure.

In addition, rabbit polyclonal antibodies specific to α-fetoprotein (AFP) (Dako Corp., Carpinteria, Calif.) proteins were used for immunohistochemical detection of 5 μm liver sections using methods described previously (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316). AFP and BrdU positive immunofluorescent cells were detected in the Foxm1b fl/fl HCC liver tumors induced by DEN/PB exposure, which identified proliferating AFP-positive hepatocellular carcinoma cells. Fetal hepatocytes express abundant levels of (AFP), its hepatic expression is extinguished postnatally, but AFP expression is reactivated in HCC (Kunnath and Locker, 1983, *Embo J* 2:317-324; Chen et al., 1997, *Crit Rev Eukaryot Gene Expr* 7:11-41). Thus, these studies suggested that Foxm1b is required for proliferative expansion during tumor development of hepatic adenomas and HCC.

Together, these experiments demonstrated that male Alb-Cre Foxm1b −/− mice were resistant to developing HCC in response to 33 weeks of DEN/PB exposure, a treatment sufficient to induce multiple HCC tumors in male Foxm1b fl/fl mice (Table 3).

Furthermore, control Foxm1b fl/fl and experimental Alb-Cre Foxm1b −/− mice were treated with DEN/PB for 50 weeks to determine whether Foxm1b deficient livers were resistant to a prolonged hepatic tumor induction protocol. After 50 weeks of DEN/PB exposure, all nine female Alb-Cre Foxm1b −/− mice were devoid of any liver tumors, whereas HCC tumors were found in all four control female livers with one additional control female mouse dying prematurely. Following 50 weeks of DEN/PB exposure, no liver tumors were found in two out of the four male Alb-Cre Foxm1b −/− mice, while one male mouse exhibited hepatic adenomas and the last male mouse displayed HCC tumors that were negative for Foxm1b protein staining These studies indicated that following prolonged DEN/PB tumor promotion hepatic tumors were found in a subset of the male Alb-Cre Foxm1b −/− livers, suggesting that they developed secondary mutations that allowed tumor formation bypassing the block in Foxm1b −/− hepatocyte proliferation.

Example 10

Alb-Cre Foxm1b −/− Male Mouse Hepatocytes Exhibited No Elevation in Apoptosis and Increased Hypertrophy in Response to DEN/PB Treatment TUNEL staining of liver sections from DEN/PB treated mice was used to determine whether increased apoptosis contributed to the failure of male Alb-Cre Foxm1b −/− mice to develop liver tumors in response to 33 weeks of DEN/PB treatment. The TUNEL assay was performed using the Apo-Tag Red in situ apoptosis detection kit from Intergen (Purchase, N.Y.) according to the manufacturer's recommendations. No difference was found in hepatocyte apoptosis between Alb-Cre Foxm1b −/− and Foxm1b fl/fl mice after 6, 23, or 33 weeks of DEN/PB exposure (FIG. 10A-C). These results suggested that the absence of liver tumors in Foxm1b −/− mice following DEN/PB exposure was not due to an increase in hepatocyte apoptosis.

Hypertrophy of the Alb-Cre Foxm1b −/− hepatocytes was significantly increased compared to that of control hepatocytes (non-tumor liver regions) at 23 weeks of DEN/PB exposure (FIG. 10D-E). A centromere-specific FISH probe purchased from Vysis Inc. (Downers Grove, Ill.) was used to hybridize paraffin embedded liver sections according to manufacturer's protocol, demonstrating that Alb-Cre Foxm1b −/− hepatocyte nuclei possessed an increase in hybridizing chromosomes compared to control hepatocyte nuclei at 23 weeks of DEN/PB treatment (FIG. 10E-G). To quantitate this increase in size, the number of DAPI stained hepatocyte nuclei were counted (per 200× field) in Foxm1b fl/fl and Alb-Cre Foxm1b −/− liver sections and the data for each of the time points following DEN/PB exposure was plotted (FIG. 10H). The mean number (±SD) of DAPI positive hepatocyte nuclei per 1000 cells or 200× field by counting the number of positive hepatocyte nuclei using 5 different 200× liver sections from 3 distinct male mice at the indicated times of DEN/PB exposure or untreated. After 23 or 33 weeks of DEN/PB exposure, half the number of hepatocyte nuclei per 200× field was found in Foxm1b −/− livers compared to Foxm1b fl/fl control liver (FIG. 10H). The data suggested that Foxm1b deficient hepatocytes undergo greater hypertrophy and become more polyploid than Foxm1b fl/fl control hepatocytes at 23 and 33 weeks of DEN/PB treatment. These results suggested that Alb-Cre Foxm1b −/− hepatocytes exhibited low levels of DNA replication with a significant reduction in mitosis as was previously found in Foxm1b deficient hepatocytes during liver regeneration and development (Korver et al., 1998, *Nucleic Acids Res* 25:1715-1719; Wang et al., 2002, *Proc Natl Acad Sci USA* 99:16881-16886). Moreover, Alb-Cre Foxm1b −/− hepatocytes displayed normal serum levels of albumin, bilirubin and glucose after 33 weeks of DEN/PB exposure indicating that their livers functioned normally.

Example 11

Figure 11:
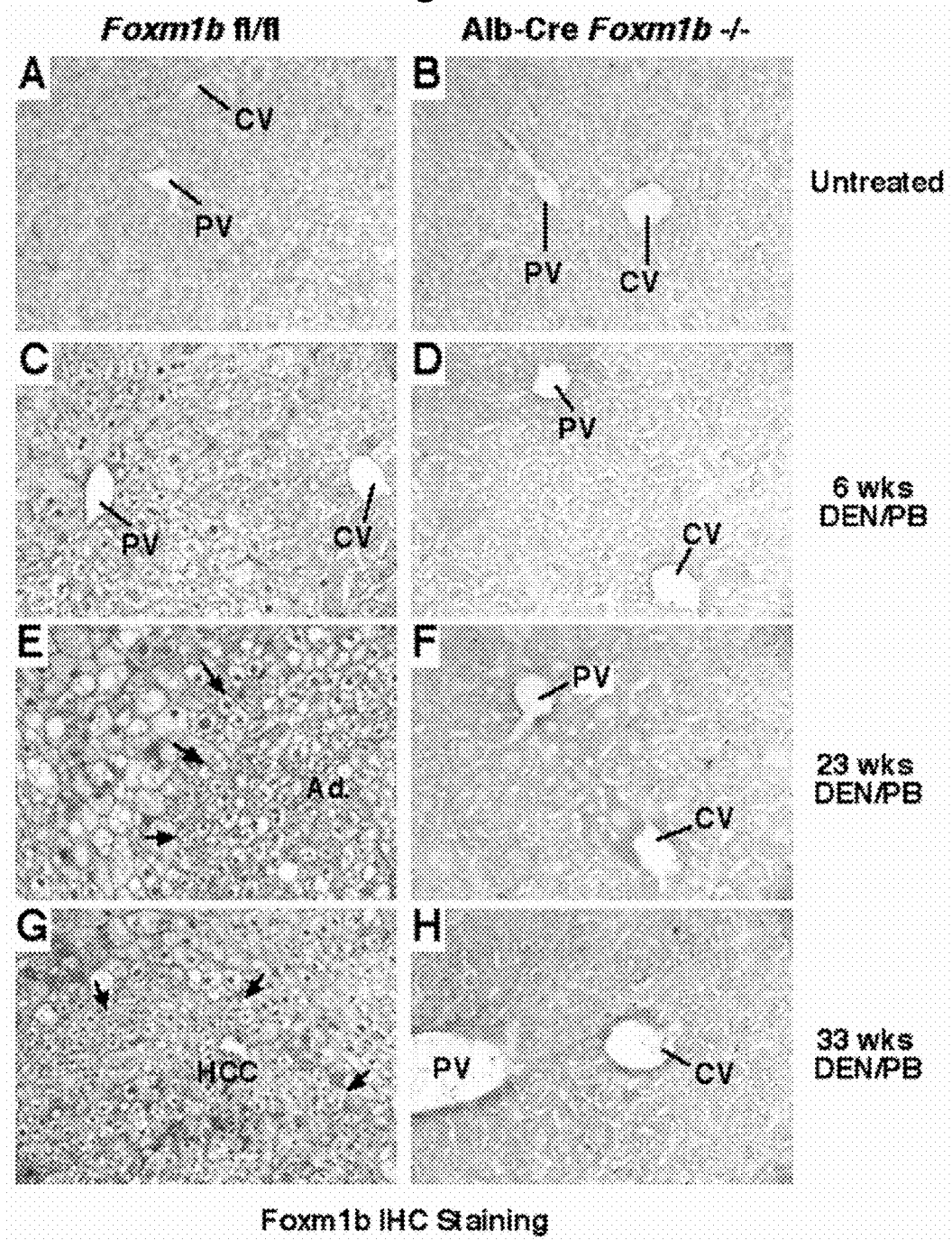

Hepatocyte Expression of Nuclear Foxm1b Protein Increases Prior to Tumor Formation and Continues During Tumor Progression Immunohistochemical staining of liver sections with an antibody specific to Foxm1b protein (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316) demonstrated that untreated hepatocyte nuclei displayed no significant expression of the Foxm1b protein (FIG. 11A-B). Abundant nuclear staining of Foxm1b protein was detected in periportal Foxm1b fl/fl hepatocytes as early as 6 weeks of DEN/PB (FIG. 11C), yet these hepatocytes failed to exhibit abundant BrdU incorporation levels. High levels of nuclear FoxM1B protein persisted in hyper-proliferative liver adenomas and HCC at 23 weeks and 33 weeks following DEN/PB exposure (FIGS. 11E and G). As expected, nuclear staining of FoxM1B protein was not found in Alb-Cre Foxm1b −/− hepatocytes at any of the time points following DEN/PB treatment (FIGS. 11D, F and H), confirming that the Alb-Cre transgene protein efficiently deleted the Foxm1b floxed targeted allele in hepatocytes (Wang et al., 2002, *Proc Natl Acad Sci USA* 99:16881-16886). These studies demonstrated that hepatocyte nuclear levels of FoxM1B were induced in control hepatocytes prior to tumor formation following DEN/PB treatment and that this nuclear expression persisted in hepatic adenomas and HCC.

Example 12

Figure 12:
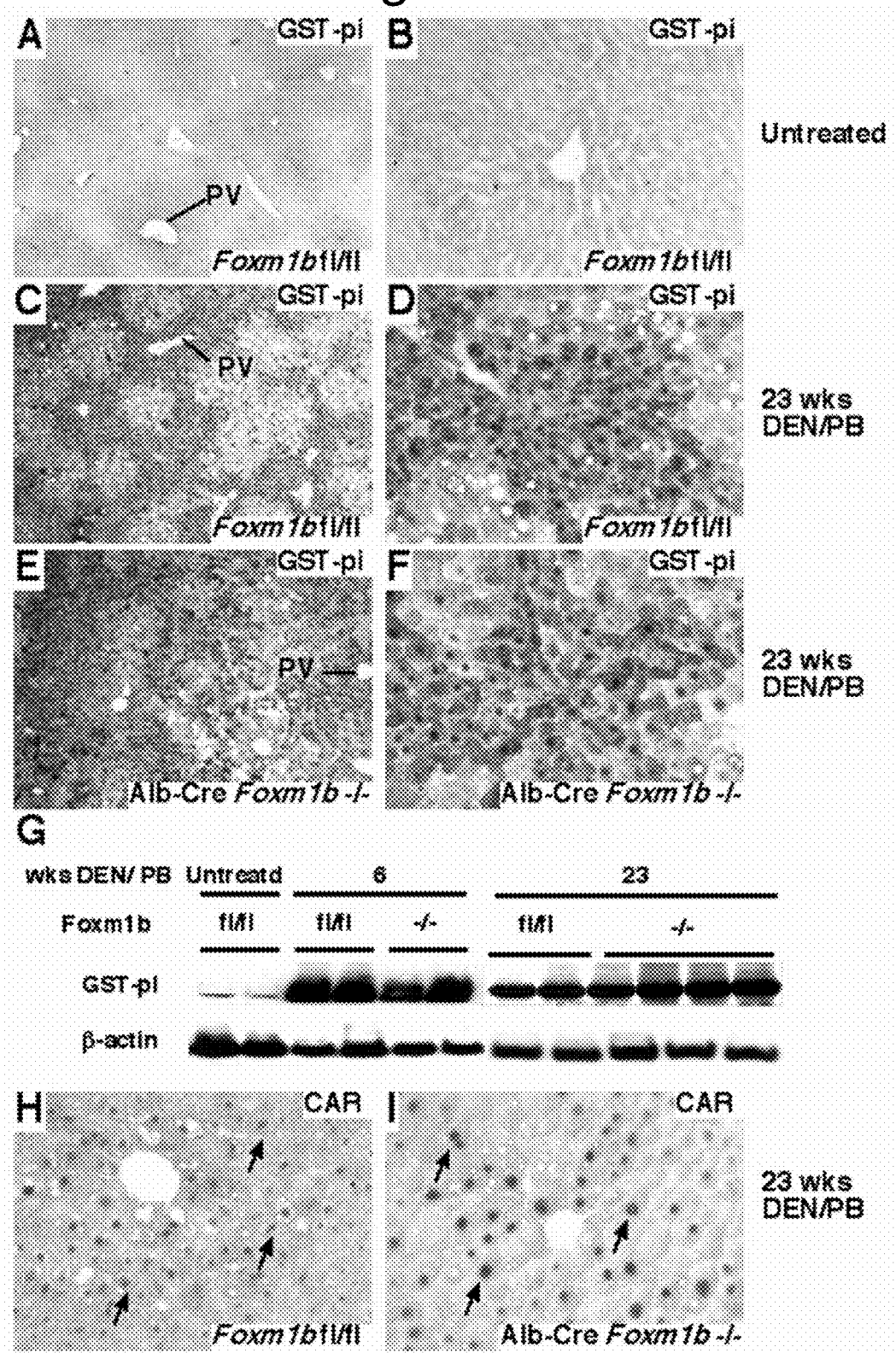

Alb-Cre Foxm1b −/− Livers Exhibit Normal Expression of GST-pi and CAR Following DEN/PB Treatment Glutathionine-S-transferase placental isoform (GST-pi) is an early marker for "altered enzyme foci" in response to DEN/PB exposure (Hatayama et al., 1993, *Carcinogenesis* 14:537-538). Rabbit polyclonal antibodies specific to GST-pi (Dako Corp., Carpinteria, Calif.) proteins were used for immunohistochemical detection of 5 μm liver sections using methods described previously (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316). GST-pi expression was not detected in liver sections of untreated control mice (FIG. 12A-B), but both Alb-Cre Foxm1b −/− and Foxm1b fl/fl hepatocytes were strongly immunostained for GST-pi after 23 weeks of DEN/PB treatment (FIG. 12C-F). Western blot analysis demonstrated that hepatic expression of GST-pi protein was induced as early as 6 weeks following DEN/PB treatment in both Alb-Cre Foxm1b −/− and Foxm1b fl/fl livers with continued expression after 23 weeks of DEN/PB exposure (FIG. 12G). Phenobarbital (PB) stimulates nuclear translocation of the constitutive androstane receptor (CAR) nuclear receptor (Chawla et al., 2001, *Science* 294:1866-1870). No difference in nuclear staining of the CAR receptor was found between Foxm1b fl/fl and Alb-Cre Foxm1b −/− hepatocytes following DEN/PB treatment (FIG. 12H-I), indicating that the Foxm1b deficient hepatocytes were still responsive to the PB tumor promoter. Taken together, the data suggest that Alb-Cre Foxm1b −/− livers responded normally to DEN/PB tumor induction and expressed the "altered enzyme foci" GST-pi marker, but that they failed to undergo the proliferation required for tumor progression.

Example 13

Persistent Nuclear Accumulation of the Cdk Inhibitor p27$^{Kip1}$ Protein and Diminished Cdc25B Expression in Alb-Cre Foxm1b −/− Livers Follows DEN/PB Exposure Liver regeneration studies demonstrated that increased expression of Foxm1b protein was associated with reduced hepatocyte nuclear levels of the Cdk inhibitor p27$^{Kip1}$ protein (Wang et al., 2002, *Proc Natl Acad Sci USA* 99:16881-16886; Wang et al., 2002, *J. Biol. Chem.* 277:44310-44316; Krupczak-Hollis et al., 2003, *Hepatology* 38:1552-1562). Consistent with these findings, persistent nuclear accumulation of hepatocyte p27$^{Kip1}$ protein was found only in Alb-Cre Foxm1b −/− liver sections at 36 hours after partial hepatectomy (PHx; FIG. 13A-B). Nuclear expression of p27$^{Kip1}$ protein was examined in mouse liver sections from untreated and DEN/PB treated mice using immunohistochemical staining Rabbit polyclonal antibodies specific to p27$^{kip1}$ (Cell Signaling, Beverly, Mass.) proteins were used for immunohistochemical detection of 5 µm liver sections using methods described previously (Ye et al., 1997, *Mol Cell Biol* 17:1626-1641; Ye et al., 1999, *Mol. Cell. Biol.* 19:8570-8580; Wang et al., 2002, *J. Biol. Chem.* 277:44310-44316). Similar hepatocyte levels of nuclear p27$^{Kip1}$ protein were found in untreated Alb-Cre Foxm1b −/− and Foxm1b fl/fl mice (FIG. 13C-D), a finding consistent with abundant nuclear expression of the Cdk inhibitor p27$^{Kip1}$ protein in quiescent hepatocytes (Kwon et al., 2002, *J Biol Chem* 277:41417-41422). Hepatocyte nuclear staining of p27$^{Kip1}$ protein was significantly diminished in Foxm1b fl/fl hepatocytes beginning at 6 weeks and continuing through 33 weeks after DEN/PB treatment (FIGS. 13E, G, I and M).

Furthermore, nuclear expression of p27$^{Kip1}$ protein was undetectable in hepatic tumor cells at all time points following DEN/PB treatment (FIGS. 13G and I). In contrast, hepatocyte nuclear staining of p27$^{Kip1}$ protein was sustained in Alb-Cre Foxm1b −/− mice at 6, 23 and 33 weeks after DEN/PB exposure (FIGS. 13F, H, J and M). After 50 weeks DEN/PB treatment, nuclear staining of p27$^{Kip1}$ protein was sustained in Female Alb-Cre Foxm1b −/− mouse hepatocytes (FIGS. 13K and N) and these livers were resistant to development of adenomas and HCC. In contrast, male Alb-Cre Foxm1b −/− mouse hepatocytes exhibited nearly undetectable nuclear staining of p27$^{Kip1}$ protein after 50 weeks of DEN/PB exposure (FIGS. 13L and N) and was associated with 50% of the male Alb-Cre Foxm1b −/− mice developing liver tumors. These results suggested that an increase in liver tumor incidence in male mice following prolonged response to DEN/PB treatment was associated with loss of hepatocyte nuclear levels of p27$^{Kip1}$ protein.

Diminished hepatocyte DNA replication in regenerating Alb-Cre Foxm1b −/− livers was associated with increased nuclear levels of the Cdk inhibitor p21$^{Cip1}$ protein (Wang et al., 2002, *Proc Natl Acad Sci USA* 99:16881-16886). Immunostaining of liver sections demonstrated that nuclear expression of p21$^{Cip1}$ protein in Alb-Cre Foxm1b −/− and Foxm1b fl/fl hepatocytes was similar and restricted to hepatocytes surrounding the central vein after 6, 23 or 33 weeks of DEN/PB treatment. The similar expression pattern of nuclear p21$^{Cip1}$ protein in hepatocytes of DEN/PB treated mice suggested that elevated p21$^{Cip1}$ protein levels were unlikely to be involved in suppressing tumor formation in Alb-Cre Foxm1b −/− livers.

Western blot analysis revealed similar levels of total p27$^{Kip1}$ protein in Foxm1b fl/fl and Alb-Cre Foxm1b −/− liver extracts at 6, 23 or 33 weeks following DEN/PB exposure (FIG. 14A). These results suggested that Foxm1b deficiency resulted in sustained hepatocyte levels of nuclear p27$^{Kip1}$ protein after DEN/PB treatment without changing total expression of the p27$^{Kip1}$ protein.

The Western blot was then stripped and probed sequentially with antibodies specific to the Cdk-activating Cdc25B or Cdc25C phosphatases (Santa Cruz Biotech) at a concentration of 1:1000. Foxm1b fl/fl control livers exhibited a transient increase in expression of the M-phase promoting Cdc25B phosphatase protein at 6 weeks after DEN/PB exposure, whereas hepatic levels of Cdc25B protein were significantly diminished in Alb-Cre Foxm1b −/− livers (FIG. 14A). Similar levels of Cdc25C protein are found in liver extracts from Alb-Cre Foxm1b −/− and Foxm1b fl/fl mice after 6 weeks of DEN/PB treatment (FIG. 14A). However, diminished hepatic expression of Cdc25B and Cdc25C proteins is observed at either 23 or 33 weeks after DEN/PB exposure (FIG. 14A). Taken together, the data suggested that decreased proliferation in Alb-Cre Foxm1b −/− hepatocytes was likely due to sustained nuclear levels of Cdk inhibitor p27$^{Kip1}$ protein and diminished expression of the Cdk1-activator Cdc25B.

Example 14

The Cdk Inhibitor p27$^{Kip1}$ Protein Associates with FoxM1B through the Cdk-Cyclin Complexes and Inhibits its Transcriptional Activity FoxM1B transcriptional activity requires an LXL Cdk docking site (639-641) that recruits either the Cdk2-Cyclin E/A (S-phase) or Cdk1-Cyclin B (G2 phase) complexes to the FoxM1B transcriptional activation domain, which is required for efficient phosphorylation of the FoxM1B Cdk 596 site (Major et al., 2004, *Mol. Cell. Biol.* 24:2649-2661). Retention of this Foxm1b Cdk site at Thr 596 residue was found to be essential for transcriptional activity by mediating phosphorylation dependent recruitment of the CREB Binding Protein (CBP) histone acetyltransferase (Major et al., 2004, *Mol. Cell. Biol.* 24:2649-2661).

Protein extracts were prepared from U2OS cells that were transiently transfected with the CMV p27$^{Kip1}$ and CMV expression constructs containing either WT GFP-Foxm1b or the GFP-FoxM1B L641A mutant that failed to interact with the Cdk-Cyclin complexes (Major et al., 2004, *Mol. Cell. Biol.* 24:2649-2661). These U2OS cell transfected lysates were immunoprecipitated (IP) with the p27$^{Kip1}$ antibody (Cell Signaling, Beverly, Mass.; 1:1000) followed by Western blot analysis with GFP antibody. These Co-IP experiments demonstrated that the p27$^{Kip1}$ protein associated with the WT FoxM1B protein, whereas p27$^{Kip1}$ was unable to bind to the GFP-FoxM1B L641A mutant protein (FIG. 14C). These results suggested that the p27$^{Kip1}$ protein associated with the Cdk-Cyclin complexes, which are recruited by the FoxM1B transcriptional activation domain through the LXL Cdk docking motif (FIG. 14B).

In addition, U2OS cells were transiently transfected with the 6X FoxM1B-TATA-luciferase reporter plasmid (Rausa et al., 2003, *Mol Cell Biol* 20:8264-8282; Major et al., 2004, *Mol. Cell. Biol.* 24:2649-2661) with the CMV WT FoxM1B and p27$^{Kip1}$ expression vectors to determine whether the p27$^{Kip1}$ protein could inhibit Foxm1b transcriptional activity. Transfected cells were harvested at 48 hours after transfection and processed for dual luciferase assays to determine FoxM1B transcriptional activity. Cotransfection of p27$^{Kip1}$ expression vector caused a significant reduction in FoxM1B transcriptional activity (FIG. 14D). This finding was consistent with the ability of the p27$^{Kip1}$ protein to inhibit kinase activity of the Cdk-Cyclin complexes (Polyak et al., 1994, *Genes Dev* 8:9-22; Zerfass-Thome et al., 1997, *Mol Cell Biol* 17:407-415) required for FoxM1B transcriptional activity through Cdk phosphorylation dependent recruitment of the CBP coactivator protein (Major et al., 2004, *Mol. Cell. Biol.* 24:2649-2661).

Example 15

Endogenous p19$^{ARF}$ Tumor Suppressor Associates with FoxM1B Protein in Liver Extracts Prepared from Mice Following 6 Weeks of DEN/PB Exposure Hepatic expression of p19 protein in livers from mice exposed to DEN/PB was examined by Western blot analysis. For Western blotting, 100 μg of total protein extracts prepared from liver following the procedure in Rausa et al., 2000, *Mol Cell Biol* 20:8264-8282) were separated on SDS-PAGE and transferred to PVDF membrane (BioRAD). Rabbit antibodies specific to p19$^{ARF}$ (AB80; GeneTex, San Antonio, Tex.; 1:750) proteins were used as primary antibody. The primary antibody signals were amplified by HRP-conjugated secondary antibodies (Bio-Rad, Hercules, Calif.), and detected with Enhanced Chemiluminescence Plus (ECL-plus, Amersham Pharmacia Biotech, Piscataway, N.J.).

Western Blot analysis demonstrated that hepatic expression of p19 protein was induced at 6 weeks after DEN/PB exposure, but liver expression of p19 was significantly diminished by 23 weeks following DEN/PB exposure (FIG. 15A), a finding consistent with those obtained with other tumors (Sherr and McCormick, 2002, *Cancer Cell* 2:103-112).

Co-immunoprecipitation (Co-IP) assays were performed with liver protein extracts prepared from Foxm1b fl/fl and Alb-Cre Foxm1b −/− mice following either 6 or 23 weeks of DEN/PB treatment (FIG. 15B) to determine whether the p19 tumor suppressor protein associated with the FoxM1B protein. For Co-IP experiments, 500 μg of protein extract prepared from DEN/PB treated liver were immunoprecipitated with p19$^{ARF}$ antibody (AB80; GeneTex, San Antonio, Tex.; 2 μg) followed by Western Blot analysis with mouse antibody FoxM1B protein (1:5000). The signals from the primary antibody were amplified by HRP conjugated anti-mouse IgG (Bio-Rad, Hercules, Calif.), and detected with Enhanced Chemiluminescence Plus (ECL-plus, Amersham Pharmacia Biotech, Piscataway, N.J.). As a positive control, Co-IP experiments were performed with protein extracts prepared from mouse embryo fibroblasts (MEFs) that were cultured in vitro for 12 passages to induce endogenous protein expression of the p19 tumor suppressor (Kamijo et al., 1997, *Cell* 91:649-659). These Co-IP studies demonstrated efficient association between endogenous FoxM1B and p19 proteins in extracts prepared from either Foxm1b fl/fl livers at 6 weeks of DEN/PB exposure or late passage MEFs, but not with liver extracts from Alb-Cre Foxm1b −/− mice (FIG. 15B). Negative controls showed that Foxm1b protein failed to Co-IP with p19 in protein extracts prepared from Foxm1b fl/fl livers at 23 weeks of DEN/PB treatment, which no longer expressed the p19 protein but continued to express Foxm1b protein (FIGS. 15B and 11C).

Example 16

FoxM1B and p19 Cotransfection Assays and Synthesis of (D-Arg)$_9$-p19$^{ARF}$ 26-44 Peptide Human osteosarcoma U2OS cells were maintained in DMEM supplemented with 10% fetal calf serum, 1× Pen/Strep and 1× L-Glutamine (Gibco). For transient transfection, U2OS cells were plated in six-well plates and transfected using Fugene 6 reagent (Roche) according to the manufacturer's protocol. Cells were transfected with 500 ng of CMV WT FoxM1B 1-748 alone or with CMV expression vectors containing either WT T7-p19$^{ARF}$ or N-terminal mutant T7-p19$^{ARF}$ protein (Δ1-14, Δ15-25, Δ26-37, or Δ26-37+Δ1-14) or V5-TAT-p19$^{ARF}$ 26-44 or V5-TAT-p19$^{ARF}$ 26-55 sequences and with 1.5 μg of a 6X FoxM1B TATA-Luciferase reporter. Ten nanograms of CMV-Renilla luciferase reporter plasmid were included as an internal control to normalize transfection efficiency. Cotransfection assays were also performed with 500 ng of CMV FoxM1B 1-688 and 6X FoxM1B TATA-Luciferase reporter and 10 ng of CMV-Renilla internal control. Twenty-four hours post-transfection, cells were prepared for dual luciferase assays (Promega). Luciferase activity was determined as percent of wild type FoxM1B activity following normalization to Renilla activity. Experiments were performed at least four times in triplicate and mean±SD determined.

The Sigma-Genosys company (The Woodlands, Tex.) synthesized a (D-Arg)$_9$-p19ARF 26-44 peptide (rrrrrrrrrK-FVRSRRPRTASCALAFVN; SEQ ID NO: 10) containing nine D-Arg residues (SEQ ID NO: 14) at the N-terminus, which has been demonstrated to enhance cellular uptake of polypeptides (Wender et al., 2000, *Proc Natl Acad Sci USA* 97:13003-13008). The (D-Arg)$_9$-p19ARF 26-44 peptide was tagged with a fluorescent Lissamine (TRITC) on the N-terminus and acetylated at the C-terminus and was purified by high-pressure liquid chromatography (Sigma-Genosys). Cotransfection assays were also performed with 500 ng of CMV FoxM1B 1-688, 6X FoxM1B TATA-Luciferase reporter and 10 ng of CMV-Renilla internal control. The transfected U2OS cells were treated with 12 μM of the p19$^{ARF}$ rrrrrrrrrKFVRSRRPRTASCALAFVN (SEQ ID NO: 10) peptide for 24 hours and then harvested for dual luciferase assays (Promega) as described above.

U2OS cells were transiently transfected in 2 well chamber slides (Nunc) with CMV GFP-FoxM1B expression constructs in the presence or absence of either CMV WT T7-p19$^{ARF}$, CMV HA-p19$^{ARF}$, or CMV expression constructs containing either N-terminal mutant T7-p19$^{ARF}$ proteins (Δ1-14, Δ15-25, or Δ26-37) or V5-TAT-p19$^{ARF}$ proteins (26-44; SEQ ID NO: 11, or 26-55; SEQ ID NO: 12). U2OS cells were transiently transfected with CMV EGFP expression vector containing the TAT-p19$^{ARF}$ proteins (26-44; SEQ ID NO: 11, or 26-55; SEQ ID NO: 12). Forty-eight hours post transfection, cells were fixed in 4% Para-formaldehyde for 20 minutes at room temperature. GFP fluorescence or immunofluorescence with anti-HA antibody following TRITC conjugated secondary antibody was detected using a Zeiss microscope. U2OS cells were treated with 12 μM of the arrrarrKFVRSRRPRTASCALAFVN (SEQ ID NO: 10) peptide for 24 hours and then analyzed for TRITC fluorescence as described above.

Example 17

Creation of Doxycycline Inducible CMV-TETO GFP-FoxM1B U2OS Cell Line and Soft Agar Assays The T-REx™-U2OS cells were purchased from Invitrogen Life Technologies (Catalog No. R712-07). The T-REx™-U2OS cells express the Tet repressor from pCEP4/tetR that was episomally maintained in tissue culture medium containing 10% fetal calf serum and drug selection with 50 μg/ml of Hygromycin B. Tetracycline regulation in the T-REx System was based on the binding of tetracycline to the TET repressor and de-repressing of the CMV-TETO promoter controlling expression of the gene of interest (Yao et al., 1998, *Hum Gene Ther* 9:1939-1950). The pCDNA4-TO GFP-FoxM1B expression plasmid provided in the T-REx™ system was generated as described previously (Major et al., 2004, *Mol.*

Cell. Biol. 24:2649-2661) and transfected T-REx™-U2OS cells with linearized pCDNA4-TO GFP-Foxm1b expression plasmid to select clonal Doxycycline inducible GFP-Foxm1b U2OS cell lines. CMV-TETO GFP-FoxM1B U2OS clones were isolated by selection for three weeks with tissue culture medium containing 50 µg/ml of Hygromycin B and 250 µg/ml of Zeocin. The CMV-TETO GFP-Foxm1b U2OS clone C3 cell line was selected for the soft agar assays because it exhibited intermediate expression of the GFP-Foxm1b fusion protein in response to 1 µg/ml of Doxycycline (Sigma D-9891) as determined by Western blot analysis with GFP monoclonal antibody. Wild type U2OS cells or CMV-TETO GFP-Foxm1b U2OS clone C3 cells were grown in medium with or without 1 µg/ml of Doxycycline for 2 days prior to either adding the (D-Arg)$_9$-p19$^{ARF}$ 26-44 peptide or left untreated. A concentration of 12 µM of p19$^{ARF}$ peptide (rrrrrrrrrKFVRSRRPRTASCALAFVN; SEQ ID NO: 10) was added to the cells for 24 hours prior to splitting the cells for the soft agar assays using procedures described previously (Conzen et al. 2000, Mol Cell Biol 20:6008-6018). U2OS cells (10$^5$) were plated subconfluently in a 6 well plates in 0.7% agarose on a 1.4% agarose bed in the presence or absence of 12 µM of the (D-Arg)$_9$-p19$^{ARF}$ 26-44 peptide and 1 µg/ml of Doxycycline. Every 4 days the tissue culture medium containing 10% fetal calf serum, 12 µM of the (D-Arg)$_9$-p19$^{ARF}$ 26-44 peptide and 1 µg/ml of Doxycycline was replaced. Controls included growth in medium containing 10% fetal calf serum with or without 1 µg/ml of Doxycycline. U2OS cell colonies that were larger than 1 mm in size were scored after two weeks of growth on the soft agar.

Example 18

The p19$^{ARF}$ 26 to 44 Sequences are Sufficient to Associate with and Inhibit FoxM1B Transcriptional Activity To identify p19$^{ARF}$ protein sequences essential for association with FoxM1B protein, Co-IP assays were performed with protein extracts prepared from transiently transfected U2OS cells, which lack endogenous expression of the p19$^{ARF}$ tumor suppressor protein (Martelli et al., 2001, Proc Natl Acad Sci USA 98:4455-4460). U2OS cells were co-transfected with CMV Green Fluorescent Protein (GFP)-FoxM1B expression vector and CMV expression plasmids containing either WT p19$^{ARF}$ protein or N-terminal deletion mutants of the p19$^{ARF}$ protein (Δ1-14, Δ15-25, Δ26-37, or Δ26-37+Δ1-14) that were fused to the HA epitope tag (Weber et al., 2000, Mol Cell Biol 20:2517-2528). Protein extracts were incubated with HA antibody to immunoprecipitate (IP) the HA-p19$^{ARF}$ protein followed by Western blot analysis with a monoclonal antibody specific to GFP protein to detect the GFP-FoxM1B fusion protein. These Co-IP experiments demonstrated that the N-terminal 25 amino acid residues of the p19ARF (p19) protein were dispensable for association with the GFP-FoxM1B protein (FIG. 15C-D). In contrast, the p19 amino acid residues 26 to 37 were essential for association with the GFP-Foxm1b fusion protein (FIG. 15C-D). Furthermore, retention of the C-terminal 60 amino acids from the FoxM1B protein (688-748) was required for p19 protein binding (FIG. 15C-D).

To identify p19 protein sequences that are sufficient for association with FoxM1B protein, Co-IP assays were performed with protein extracts prepared from U2OS cells that were transiently transfected with CMV GFP-FoxM1B expression plasmid and the CMV expression vector containing the V5 epitope tagged p19$^{ARF}$ 26-44 or p19$^{ARF}$ 26-55 sequences. At the amino terminus of either the p19$^{ARF}$ sequences 26 to 44 or 26 to 55, we placed the protein transduction/nuclear localization domain (MGYGRKKRRQRRR; SEQ ID NO: 13) from the HIV-TAT protein (Becker-Hapak et al., 2001, Methods 24:247-256). Protein extracts were incubated with the V5 epitope tag antibody to IP the p19 protein followed by Western blot analysis with GFP monoclonal antibody to detect the GFP-FoxM1B fusion protein. These Co-IP experiments demonstrated that p19 amino acid residues 26-44 were sufficient to associate with the FoxM1B protein (FIG. 15E).

To determine whether formation of the p19-FoxM1B protein complex could effectively inhibit FoxM1B transcriptional activity, U2OS cells were transiently transfected with the 6X Foxm1b-TATA-luciferase reporter plasmid (Rausa et al., 2003, Mol. Cell. Biol. 23:437-449; Major et al., 2004, Mol. Cell. Biol. 24:2649-2661) and the CMV WT FoxM1B and p19 expression vectors (FIG. 15F). These cotransfection assays demonstrated that both WT p19 and mutant T7-p19$^{ARF}$Δ1-14, T7-p19$^{ARF}$Δ15-25, V5-TAT-p19$^{ARF}$ 26-44 and V5-TAT-p19$^{ARF}$ 26-55 proteins that retained their ability to associate with FoxM1B protein (FIG. 15D-E) were able to significantly decrease FoxM1B transcriptional activity (FIG. 15F). In contrast, the T7-p19$^{ARF}$Δ26-37 proteins, which no longer associated with the FoxM1B protein (FIG. 15D) were unable to significantly reduce FoxM1B transcriptional activity in these cotransfection assays (FIG. 15F). Interestingly, deletion of the FoxM1B C-terminal sequences required for association with p19 protein (FIG. 15D; Foxm1b 1-688) was also found to be essential for FoxM1B transcriptional activity (FIG. 15F). These studies demonstrated that FoxM1B transcription factor was a novel inhibitory target for the p19$^{ARF}$ tumor suppressor, a finding consistent with the important role of FoxM1B in proliferative expansion during liver tumor progression.

Example 19

The p19$^{ARF}$ Tumor Suppressor Targets FoxM1B Protein to the Nucleolus

U2OS cell cotransfection studies demonstrated that HA tagged p19 was able to target GFP-FoxM1B fusion protein to the nucleolus (FIG. 16A-C). While GFP-FoxM1B 1-748 full-length protein exhibited nuclear staining (FIG. 16D), nucleolar targeting of GFP-FoxM1B fusion protein was found in cotransfections with expression vectors containing either WT p19 or mutant p19 proteins that were still able to associate with FoxM1B protein (FIG. 16E-F). The GFP-FoxM1B protein was targeted to the nucleolus by expression vectors containing either the V5-TAT-p19$^{ARF}$ 26-44 or V5-TAT-p19$^{ARF}$ 26-55 sequences (FIG. 16G-H) and these p19 sequences were also localized to the nucleolus (FIG. 16I). In contrast, nuclear fluorescence was found with the GFP-FoxM1B WT protein that was transfected with the CMV p19$^{ARF}$Δ26-37 mutant that failed to associate with FoxM1B protein (FIG. 16J). Likewise, cotransfection assays with the CMV WT p19 and CMV GFP-FoxM1B 1-688 expression vectors showed nuclear fluorescence of the mutant GFP-Foxm1b 1-688 protein, a finding consistent with this FoxM1B mutant's inability to associate with the p19 protein (FIGS. 16K and 15B). These studies suggested that association between the p19 tumor suppressor and FoxM1B resulted in targeting FoxM1B to the nucleolus and FoxM1B transcriptional inhibition.

Example 20

(D-Arg)$_9$ p19$^{ARF}$ 26 to 44 Peptide Significantly Reduces Both FoxM1B Transcriptional Activity and Foxm1b Induced Cell Colony Formation on Soft Agar The p19$^{ARF}$ 26-44 peptide containing nine D-Arg residues (SEQ ID NO: 14) at the N-terminus was fluorescently tagged with Lissamine (TRITC) on the N-terminus and acetylated at the C-terminus as described above. Treatment of U2OS cells with 12 μM of the (D-Arg)$_9$-p19$^{ARF}$ 26-44 peptide (rrrrrrrrrK-FVRSRRPRTASCALAFVN; SEQ ID NO: 10) for three days demonstrated that this (D-Arg)$_9$-p19$^{ARF}$ 26-44 peptide was efficiently transduced into all of the cells and that its fluorescence localized to the nucleolus (FIG. 16L). Furthermore, exposure of U2OS cells with 12 μM of the (D-Arg)$_9$-p19$^{ARF}$ 26-44 peptide for five days caused neither toxicity nor any increases in apoptosis. Furthermore, treatment of U2OS cells with 12 μM of the (D-Arg)$_9$-p19$^{ARF}$ 26-44 peptide that were transfected with CMV-FoxM1B expression vector and the 6X FoxM1B-TATA-luciferase plasmid resulted in significant reduction in FoxM1B transcriptional activity (FIG. 17A), suggesting that this p19$^{ARF}$ peptide was an effective inhibitor of FoxM1B transcriptional activity.

In addition, the tetracycline (TET) regulated T-REx™ System described above was used to conditionally express the GFP-FoxM1B protein in U2OS cells to determine whether conditional overexpression of FoxM1B protein could enhance anchorage-independent growth of U2OS cells. The CMV-TETO GFP-FoxM1B expression plasmid was transfected into T-REx™-U2OS cells (containing TET repressor) and clonal U2OS cell lines were selected that were Doxycycline-inducible for GFP-FoxM1B expression. In response to Doxycycline treatment, the CMV-TETO GFP-FoxM1B U2OS clone C3 cell line displayed inducible intermediate levels of the GFP-FoxM1B fusion protein (FIG. 17B). The U2OS clone C3 cell line was selected to examine whether doxycycline induced FoxM1B-GFP expression enhanced anchorage-independent growth as assessed by propagation for two weeks on soft agar (Conzen et al., 2000, *Mol Cell Biol* 20:6008-6018). The soft agar experiments demonstrated that induced expression of GFP-FoxM1B protein caused a significant increase in anchorage-independent growth as evidenced by increasing the number and size of U2OS cell colonies on soft agar (FIGS. 17G and I) compared to uninduced controls (FIG. 17F) or the WT U2OS cells (FIG. 17C-D).

The results suggested that the FoxM1B protein displayed oncogenic properties by stimulating anchorage-independent growth of U2OS cell colonies on soft agar. In order to determine whether the (D-Arg)$_9$-p19$^{ARF}$ 26-44 peptide inhibited FoxM1B induced colony formation of U2OS cells on soft agar, the Doxycycline induced U2OS clone 3 cells were treated with 12 μM of the (D-Arg)$_9$-p19$^{ARF}$ 26-44 peptide one day prior to plating and was added at this concentration of (D-Arg)$_9$-p19$^{ARF}$ 26-44 peptide in the soft agar and growth medium throughout the duration of the experiment as described above. The results of these soft agar studies demonstrated that the (D-Arg)$_9$-p 19$^{ARF}$ 26-44 peptide significantly diminished the ability of induced GFP-FoxM1B to stimulate colony formation of the U2OS clone C3 cells on soft agar (FIGS. 17H and I). Furthermore, the (D-Arg)$_9$-p19$^{ARF}$ 26-44 peptide significantly diminished the ability of the parental U2OS cells to form colonies on soft agar (FIGS. 17E and I). Taken together these studies suggested that the (D-Arg)$_9$-p19$^{ARF}$ 26-44 peptide is an effective inhibitor of both FoxM1B mediated transcriptional activation and FoxM1B induced stimulation in anchorage-independent growth that is required for cellular transformation.

It should be understood that the foregoing disclosure emphasizes certain specific embodiments of the invention and that all modifications or alternatives equivalent thereto are within the spirit and scope of the invention as set forth in the appended claims.

---

We claim:

1. A method of inhibiting proliferation of a prostate tumor cell comprising the step of inhibiting FoxM1B activity in the prostate tumor cell by contacting the cell with a p19$^{ARF}$ protein fragment that can inhibit FoxM1B activity in the prostate tumor cell, wherein the p19$^{ARF}$ protein fragment comprises (1) a first peptide consisting of SEQ ID NO:11, and (2) a second peptide covalently linked to the amino terminus of the first peptide, wherein the second peptide enhances cellular uptake of the p19$^{ARF}$ protein fragment.

2. The method of claim 1, wherein the second peptide is an HIV TAT peptide of SEQ ID NO:13.

3. The method of claim 1, wherein the second peptide is a nine D-Arg peptide of SEQ ID NO:14.

4. The method of claim 1, wherein the p19' protein fragment comprises a fusion protein of SEQ ID NO:11 and a nine D-Arg peptide of SEQ ID NO:14.

5. The method of claim 1, wherein the p19$^{ARF}$ protein fragment consists of a fusion protein of SEQ ID NO:11 and a nine D-Arg peptide of SEQ ID NO:14.

6. The method of claim 1, wherein the prostate tumor cell is a malignant prostate tumor cell.

7. The method of claim 1, wherein the prostate tumor cell is of epithelial cell origin.

8. A method of inhibiting growth of a prostate tumor cell in an animal, by administering a pharmaceutical composition comprising a P19$^{ARF}$ protein fragment that can inhibit FoxM1B activity in the prostate tumor cell, wherein the p19$^{ARF}$ protein fragment comprises (1) a first peptide consisting of SEQ ID NO:11, and (2) a second peptide covalently linked to the amino terminus of the first peptide, wherein the second peptide enhances cellular uptake of the p19$^{ARF}$ protein fragment.

9. The method of claim 8, wherein the pharmaceutical composition further comprises at least one pharmaceutically acceptable carrier, diluent or excipient.

10. The method of claim 8, wherein the pharmaceutical composition is administered to the animal parenterally.

11. The method of claim 8, wherein the pharmaceutical composition is administered to the animal by intraperitoneal injection.

12. The method of claim 8, wherein the animal is human.

13. A method of inhibiting proliferation of a prostate tumor cell comprising the step of inhibiting FoxM1B activity in the prostate tumor cell by contacting the cell with a p19$^{ARF}$ protein fragment that can inhibit FoxM1B activity in the prostate tumor cell, wherein the p19$^{ARF}$ protein fragment comprises (1) a first peptide from p19$^{ARF}$ polypeptide and consisting of SEQ ID NO:12, and (2) a second peptide covalently linked to the amino terminus of the first peptide at p19$^{ARF}$ amino acid residue position 26 of the first peptide, wherein the second peptide enhances cellular uptake of the p19$^{ARF}$ protein fragment.

14. The method of claim 13, wherein the second peptide is an HIV TAT peptide of SEQ ID NO:13.

15. The method of claim 13, wherein the second peptide is a nine D-Arg peptide of SEQ ID NO:14.

16. The method of claim 13, wherein the p19$^{ARF}$ protein fragment comprises a fusion protein of SEQ ID NO:12 and a nine D-Arg peptide of SEQ ID NO:14.

17. The method of claim 13, wherein the p19$^{ARF}$ protein fragment consists of a fusion protein of SEQ ID NO:12 and a nine D-Arg peptide of SEQ ID NO:14.

18. The method of claim 13, wherein the prostate tumor cell is a malignant prostate tumor cell.

19. The method of claim 13, wherein the prostate tumor cell is of epithelial cell origin.

20. A method of inhibiting growth of a prostate tumor cell in an animal, by administering a pharmaceutical composition comprising a P19$^{ARF}$ protein fragment that can inhibit FoxM1B activity in the prostate tumor cell, wherein the p19$^{ARF}$ protein fragment comprises (1) a first peptide from p19$^{ARF}$ polypeptide and consisting of SEQ ID NO:12, and (2) a second peptide covalently linked to the amino terminus of the first peptide at p19$^{ARF}$ amino acid residue position 26 of the first peptide, wherein the second peptide enhances cellular uptake of the $p19^{ARF}$ protein fragment.

21. The method of claim 20, wherein the pharmaceutical composition further comprises at least one pharmaceutically acceptable carrier, diluent or excipient.

22. The method of claim 20, wherein the pharmaceutical composition is administered to the animal parenterally.

23. The method of claim 20, wherein the pharmaceutical composition is administered to the animal by intraperitoneal injection.

24. The method of claim 20, wherein the animal is a human.

* * * * *